(12) United States Patent
Ding et al.

(10) Patent No.: US 7,678,791 B2
(45) Date of Patent: Mar. 16, 2010

(54) NITROHETEROARYL-CONTAINING RIFAMYCIN DERIVATIVES

(75) Inventors: Charles Z. Ding, Plano, TX (US); In Ho Kim, Dublin, OH (US); Jiancheng Wang, Addison, TX (US); Zhenkun Ma, Westfield, NJ (US); Yafei Jin, Ann Arbor, MI (US); Keith D. Combrink, Arlington, TX (US); Genliang Lu, Plano, TX (US); A. Simon Lynch, Dallas, TX (US)

(73) Assignee: Cumbre IP Ventures, L.P., Dallas, TX (US)

( * ) Notice: Subject to any disclaimer, the term of this patent is extended or adjusted under 35 U.S.C. 154(b) by 193 days.

(21) Appl. No.: 11/827,467

(22) Filed: Jul. 12, 2007

(65) Prior Publication Data

US 2008/0139577 A1 Jun. 12, 2008

Related U.S. Application Data

(60) Provisional application No. 60/830,245, filed on Jul. 12, 2006.

(51) Int. Cl.
*C07D 498/22* (2006.01)
*A61K 31/535* (2006.01)
*A61P 31/00* (2006.01)

(52) U.S. Cl. ............ 514/230.5; 514/232.8; 514/252.11; 514/254.02; 514/254.06; 514/254.07; 540/453; 540/456; 540/457; 540/458

(58) Field of Classification Search ................ 540/453, 540/456, 457, 458; 514/230.5, 232.8, 252.11, 514/254.02, 254.06, 254.07
See application file for complete search history.

(56) References Cited

U.S. PATENT DOCUMENTS

| | | | |
|---|---|---|---|
| 2,610,181 A | 9/1952 | Hayes | |
| 2,944,061 A | 7/1960 | Robert et al. | |
| 3,342,810 A | 9/1967 | Maggi et al. | |
| 3,950,351 A | 4/1976 | Rossignol et al. | |
| 4,165,317 A | 8/1979 | Rossetti et al. | |
| 4,219,478 A | 8/1980 | Marsili et al. | |
| 4,983,602 A | 1/1991 | Yamane et al. | |
| 6,087,358 A | 7/2000 | Baker et al. | |

FOREIGN PATENT DOCUMENTS

| | | |
|---|---|---|
| EP | 0333176 A2 | 9/1989 |
| GB | 1603127 | 11/1981 |
| WO | WO 03/045319 | 6/2003 |
| WO | WO 2005/042542 A1 | 5/2005 |

OTHER PUBLICATIONS

Dahlig, Halina et al., Preparation of 3-(4-Acyl-1-piperazinoiminomethyl) rifamycin SV . . . , Chemical Abstracts, vol. 105, No. 23, Dec. 8, 1986.
International Search Report and Written Opinion, International Application No. PCT/US2007/015970, Cumbre Pharmaceuticals, Dec. 20, 2007.
Kump, Wilhelm, Bickel, Hans, Helv. Chim. Acta., 1973, 56, p. 2369.
Chaisson, R.E. "Treatment of chronic infections with rifamycins: is resistance likely to follow?", Antimicrob. Agents & Chemother. 47(10): p. 3037-39 (2003).
Farr, B. M. Rifamycins, in Principles and Practice of Infectious Diseases; Mandell, G. L., Bennett, J. E., Dolin, R., Eds.; Churchhill Livingstone: Philadelphia; p. 348-361.

*Primary Examiner*—Bruck Kifle
(74) *Attorney, Agent, or Firm*—Jackson Walker L.L.P.

(57) ABSTRACT

Substituted rifamycin derivatives in which a nitroimidazole, nitrothiazole or nitrofuran pharmacophore is covalently bonded to a rifamycin, methods of using the rifamycin derivatives, and pharmaceutical compositions containing the rifamycin derivatives are disclosed. Methods of synthesizing these substituted rifamycin derivatives are also disclosed. The rifamycin derivatives possess antibacterial activity, and are effective against a number of human and veterinary pathogens in the treatment of bacterial diseases.

7 Claims, 4 Drawing Sheets

NITROHETEROARYL-CONTAINING RIFAMYCIN DERIVATIVES

This application claims priority to U.S. Provisional Patent Application Ser. No. 60/830,245, entitled "Nitroheteroaryl-Containing Rifamycin Derivatives" filed on Jul. 12, 2006, the entire content of which is hereby incorporated by reference.

BACKGROUND

The present invention relates to nitroheteroaryl-substituted rifamycin derivatives wherein a nitroimidazole, nitrothiazole or nitrofuran pharmacophore is chemically combined with a rifamycin. The present invention also relates to a method of preparing pharmacologically active rifamycin derivatives and various intermediates used in the method. The inventive rifamycin derivatives are useful as antimicrobial agents effective against a number of human and veterinary aerobic and anaerobic Gram positive, Gram negative pathogens, including the *Staphylococci*, for example *S. aureus; Enterococci*, for example *E. faecalis; Streptococci*, for example *S. pneumoniae; Haemophilus*, for example *H. influenza; Moraxella*, for example *M. catarrhalis*; and *Escherichia* for example *E. coli; Mycobacteria*, for example *M. tuberculosis; Helicobacter*, for example *H. pylori; Clostridium*, for example *C. difficile; Bacteroides* for example, *B. fragilis, B. vulgates*; intercellular microbes, for example *Chlamydia* and *Rickettsiae*; and *Mycoplasma*, for example *M. pneumoniae*, amongst others.

The rifamycin derivatives may be used as agents effective against GI disorders including travelers' and infectious diarrhea (*E. coli, Salmonella* and *Shigella*), hepatic encephalopathy, Crohn's disease, ulcerative colitis, irritable bowel syndrome, pouchitis, small-bowel bacterial overgrowth, peptic ulcer disease due to *H. pylori*, and diverticular disease. The present compounds also are cytotoxic anticancer agents, antifungal agents, and antiprotozoal agents (against, for example, *entamoeba histolyica*, and *Neglaria* sps). The present invention also relates to pharmaceutical compositions containing the inventive rifamycin derivatives, to methods of treating a bacterial infection using the rifamycin derivatives.

The increase in bacterial resistance to existing antibacterial agents is a major clinical problem. Accordingly, there is a need in the art for compounds, compositions, and methods of treating warm-blooded animals that suffer from a bacterial infection and are resistant to conventional antibacterial treatments. Rifamycin class of natural product derived antibiotics, like rifampin, rifabutin and rifapetine are currently used for the treatment of tuberculosis and other microbial infections (Farr, B. M. Rifamycins, in *Principles and Practice of Infectious Diseases*; Mandell, G. L., Bennett, J. E., Dolin, R., Eds.; Churchhill Livingstone: Philadelphia; p. 348-361). At present, one of the major problems associated with the rifamycin class of antimicrobial agents is the rapid development of bacterial resistance. Mutations in rifamycin's antibacterial target RNA polymerase are mainly responsible for the high frequency of development of resistance. Consequently, rifamycins are currently used only in combination therapies to minimize the development of resistance to this class of drug. Unfortunately, even with co-administration of other antibiotics, resistance development to rifamycins is frequent in the clinic (Chaisson, R. E. "Treatment of chronic infections with rifamycins: is resistance likely to follow?", *Antimicrob. Agents & Chemother.* 47(10): p. 3037-39 (2003)).

Nitroimidazoles, nitrothiazoles and nitrofurans classes of antibiotics are well-known antibacterials against anaerobic bacteria. A member of nitroimidazole class is metronidazole (U.S. Pat. No. 2,944,061), which is presently prescribed as antiprotozoal (for treatment of Trichomonas infections). Metronidazole is also clinical used for treatment of anaerobic bacterial infections due to *Clostridium* and *Bacteroides* species. Nitazoxanide (U.S. Pat. No. 3,950,351) is a nitrothiazole compound is being used for treatment of diarrhea caused by *Cryptosporidium parvum*. Nitrofurantoin (U.S. Pat. No. 2,610,181) is a member of nitrofuran class, which is being used for treatment of acute urinary tract infections. Recently a new member of nitroimidazole class of compounds 2-nitro-6,7-dihydro-5H-imidazo[2,1-b][1,3]oxazines (U.S. Pat. No. 6,087,358) described in structure (1) below were disclosed as antibacterials, wherein $R_1$ and $R_2$ are substituted or unsubstituted alkyls, aryls, alkyloxy or aryloxy; X is O, S, $NR_2$ etc.; Y, Z are $CH_2$, $CHR_2$ and heteroatoms etc. In addition, new nitroimidazole derivatives 6-nitro-2,3-dihydroimidazo[2,1-b]oxazoles (WO 2005/042542 A1) described in structure (2) below were disclosed as agents for the treatment of tuberculosis, wherein $R_1$ represents H, alkyls etc.; $R_2$ is alkoxy, aryloxy, substituted aryloxy etc.

(1)

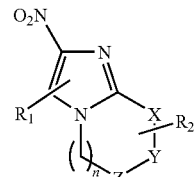

(2)

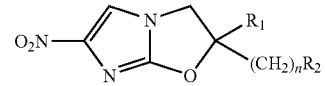

Although rifamycins, nitroimidazoles, nitrothiazoles, and nitrofurans are known, there is no reference that discloses covalently bonding a rifamycin to a nitroimidazole, a nitrothiazole or a nitrofuran and using the resulting rifamycin derivatives as anti-bacterial agents against both aerobic and anaerobic Gram-positive and negative bacteria, and defeat resistance to rifamycin.

Syntheses of simple rifamycin derivatives is well known in the art, for example, the synthesis of rifampin (U.S. Pat. No. 3,342,810), rifabutin (U.S. Pat. No. 4,219,478), and rifalazil (U.S. Pat. No. 4,983,602) are known in the art and disclosed. However, the synthesis of a rifamycin covalently linked to a nitroimidazole, a nitrothiazole or a nitrofuran is not straightforward. Thus, a method of synthesizing compounds of the present invention has not been publicized.

SUMMARY

The present invention is directed to structurally novel compounds produced by covalently bonding an antibacterial pharmacophore from nitroimidazole, nitrothiazole, or nitrofuran class of compounds to a rifamycin compound. The inventive hybrid compounds are active against bacteria where rifamycin is no longer effective. The advantage of the inventive compounds is that both the rifamycin and nitroimidazole, nitrothiazole or nitrofuran antibacterial pharmacophores are co-delivered with matched pharmacokinetics to the targeted pathogens of interests. Delivery of multiple antibacterial pharmacophores simultaneously to the targeted pathogens has the maximum chance of achieving synergy and minimizing the resistance development to the antibiotics given. The current inventive compounds have broader spectrum of antibacterial activity than either rifamycin and nitroheteroaryl class antibiotics alone. The compounds are effective against rifamycin-resistant strains of bacteria. In addition to the matched pharmacokinetics, the current inventive compounds are surprisingly more potent than what normally are expected by simple combination of two antibacterial agents. This unexpected activity in the targeted pathogen may be a result of synergistic effects of covalently linking the antibacterial pharmacophores together in the current invention.

The present compounds are active against both aerobic and anaerobic bacteria, and accordingly are useful as broad spectrum antibacterial agents. The present compounds are surprisingly effective against a number of human and veterinary aerobic and anaerobic Gram positive, Gram negative pathogens, including the *Staphylococci*, for example *S. aureus*; *Enterococci*, for example *E. faecalis*; *Streptococci*, for example *S. pneumoniae*; *Haemophilus*, for example *H. influenza*; *Moraxella*, for example *M. catarrhalis*; and *Escherichia* for example *E. coli*; *Mycobacteria*, for example *M. tuberculosis*; *Helicobacter*, for example *H. pylori*; *Clostridium*, for example *C. difficile*; *Bacteroides* for example, *B. fragilis*, B. vulgates; intercellular microbes, for example *Chlamydia* and *Rickettsiae*; and *Mycoplasma*, for example *M. pneumoniae*, amongst others. The rifamycin derivatives may be used as agents effective against GI disorders including travelers' and infectious diarrhea (*E. coli, Salmonella* and *Shigella*), hepatic encephalopathy, Crohn's disease, ulcerative colitis, irritable bowel syndrome, pouchitis, small-bowel bacterial overgrowth, peptic ulcer disease due to *H. pylori*, and diverticular disease. The present compounds also are envisioned as cytotoxic anticancer agents, antifungal agents, and antiprotozoal agents (against, for example, *entamoeba* histolyica, and *Neglaria* sps).

In a preferred embodiment, the current invention provides a series of nitroheteroaryl-substituted rifamycin derivatives represented by general formula I:

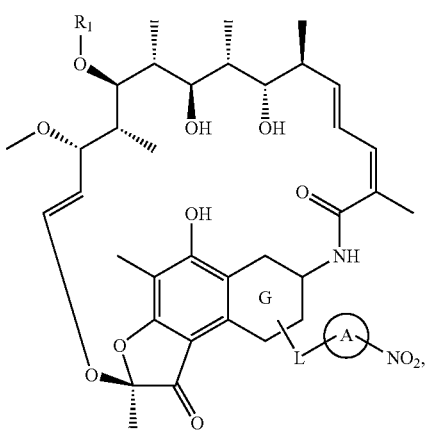

I or their pharmaceutically acceptable salt thereof, wherein $R_1$ is a hydrogen or acetyl group, G is a structure of formula II, III, IV or V:

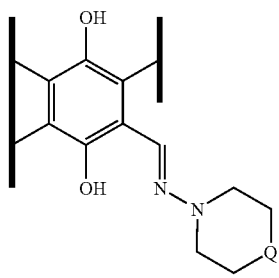

II

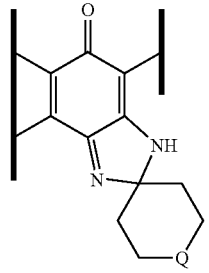

III

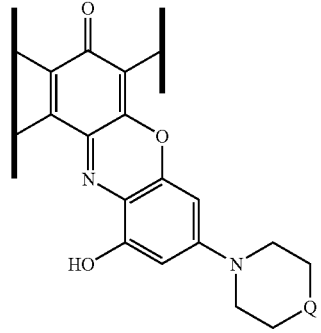

IV

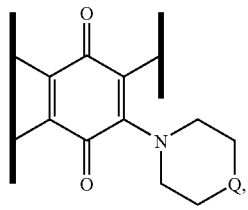

V wherein, in formula II, III, IV or V, Q is N— or $CR_2$—, which is bonded to a linkage group "L", which in turn is bonded to a structure

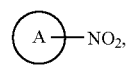

and $R_2$ is a group selected from hydrogen, substituted or unsubstituted ($C_1$-$C_6$)alkyl, aryl, heteroaryl, or heterocycloalkyl group;

L is a bond, or a linker group selected from one or a combination of two to five of the following groups:
1) ($C_1$-$C_6$)alkylene,
2) ($C_3$-$C_8$)cycloalkylene,
3) arylene,
4) heteroarylene,
5) heterocycloalkylene containing 1 to 3 heteroatoms,
6) —C(=O)—,
7) —C(=N—O—$R_3$)—,
8) —C=N—,
9) —O—,
10) —S(O)$_n$—, wherein n is number between 0 and 2,
11) —N($R_4$)—,
wherein the carbon or nitrogen atoms of the linker group are optionally substituted by 1 to 3 substituents selected from ($C_1$-$C_6$)alkyl, substituted ($C_1$-$C_6$)alkyl, amino, ($C_1$-$C_6$)alkylamino, di($C_1$-$C_6$)alkylamino, hydroxyl, ($C_1$-$C_6$)alkoxy or heterocycloalkyl group; $R_3$ and $R_4$ are independently a group selected from hydrogen, substituted or unsubstituted (C$_1$-C$_6$)alkyl, aryl, heteroaryl or heterocycloalkyl group; and structure

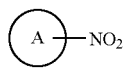

is a structural formula VI, VII, VIII or IX:

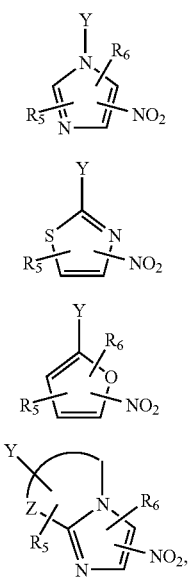

wherein Y is a bond which is bonded to linkage group "L", defined as above; and Z is a carbon (—CR$_7$R$_8$—), carbonyl (—C(O)—), amide (—C(O)N—), sulfonamide (—S(O$_2$)N—), or a heteroatom selected from N, O, S, SO or SO$_2$; wherein R$_5$, R$_6$, R$_7$, and R$_8$ are independently a group selected from hydrogen, substituted or unsubstituted (C$_1$-C$_6$)alkyl, aryl, heteroaryl, or heterocycloalkyl group; R$_5$ and R$_6$, R$_7$ and R$_8$ can join together to form a five to seven-member ring system optionally containing one to three heteroatoms.

Another aspect of the present invention is to provide a pharmaceutical composition containing a compound of formula (I) and a pharmaceutical acceptable salt, carrier, diluent, or excipient.

One other aspect of the present invention is to provide a method of treating bacterial infections in a mammal comprising administering to the mammal a pharmaceutically effective amount of a compound of formula (I).

DETAILED DESCRIPTION OF THE PREFERRED EMBODIMENTS

Figure 1:
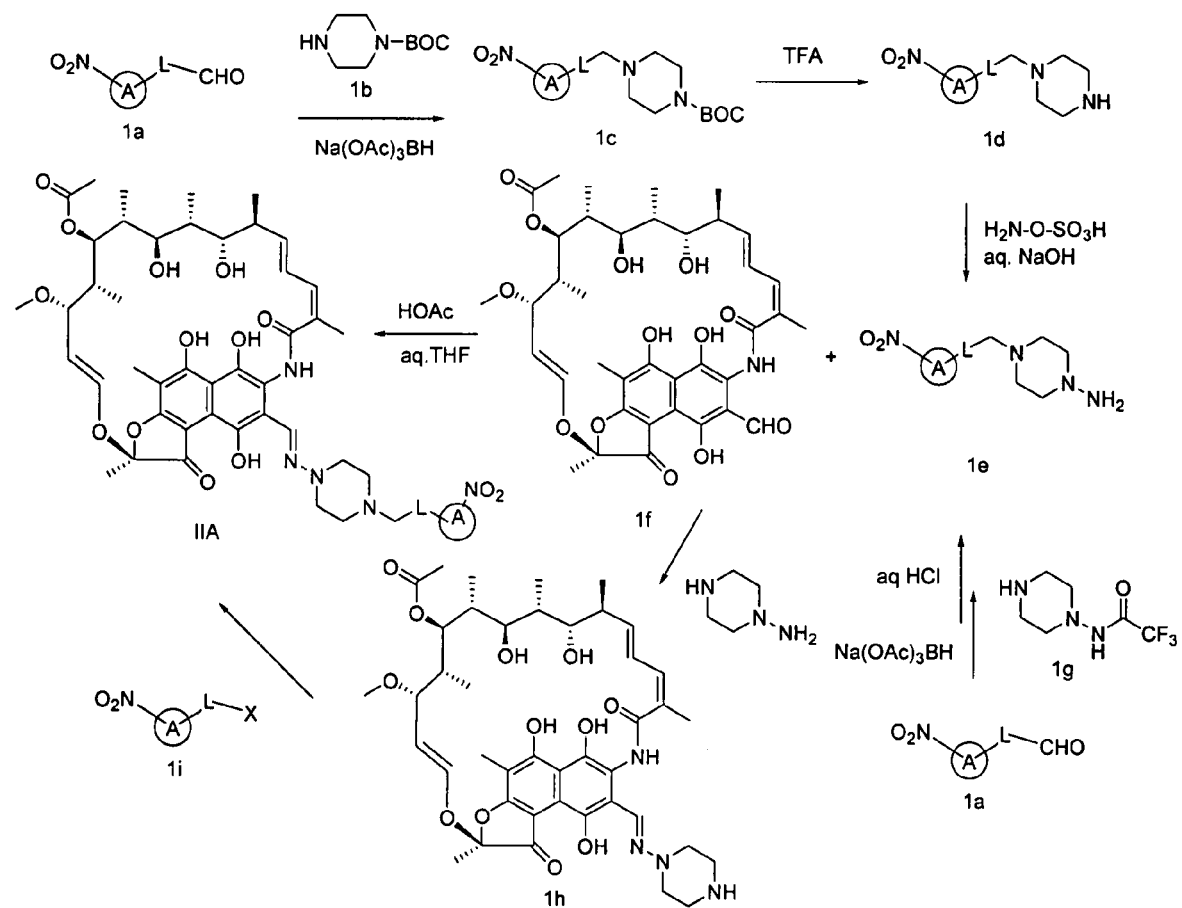
FIG. 1 shows Scheme 1, a general method for synthesizing nitroimidazole-, nitrothiazole-, or nitrofuran-substituted 3-hydrazono-rifamycin.

As used herein, the terms and phrases have the meanings and definitions known in the art. Some of the more commonly used phrases are described in more detail below.

The term "alkyl," as used herein, refers to a monovalent, saturated, straight or branched chain hydrocarbon group. Examples of alkyl groups include methyl, ethyl, propyl, iso-propyl, n-butyl, iso-butyl, tert-butyl, neo-pentyl, and n-hexyl. The alkyl groups of this invention can be optionally substituted.

The term "alkylene," as used herein, refers to bivalent saturated, straight or branched chain hydrocarbon structures. Examples of alkylene groups include methylene, ethylene, propylene, iso-propylene, n-butylene, isobutylene, and n-hexylene. The alkylene groups of this invention can be optionally substituted.

The term "alkylamino," as used herein, refers to an amino group (—NH$_2$), wherein one hydrogen atom is replaced by an alkyl group. Examples of alkylamino groups include methylamino, ethylamino, propylamino, and isopropylamino.

The term "alkylthio," as used herein, refers to an alkyl group, as defined herein, attached to the parent molecular group through a sulfur atom. Examples of alkylthio groups include methylthio, ethylthio, propylthio, and isopropylthio.

The term "alkoxy," as used herein, refers to an alkyl group, as previously defined, attached to the parent molecular group through an oxygen atom. Examples of alkoxy groups include methoxy, ethoxy, propoxy, iso-propoxy, n-butoxy, tert-butoxy, neo-pentoxy and n-hexoxy. The alkoxy groups of this invention can be optionally substituted.

The term "aryl" as used herein refers to a monovalent carbocyclic aromatic group including phenyl, naphthyl, and anthracenyl.

The term "arylene" as used herein refers to bivalent carbocyclic aromatic groups which can be optionally substituted.

The term "cycloalkyl," as used herein, refers to a monovalent saturated carbocyclic group having three to eight carbons such as cyclopropyl, cyclobutyl, cyclopentyl, cyclohexyl, cycloheptyl and cyclooctyl.

The term "cycloalkylene," as used herein, refers to bivalent saturated carbocyclic groups having three to eight carbons. The cycloalkylene groups can be optionally substituted.

The term "halogen," as used herein, refers to fluorine, chlorine, bromine and iodine atoms and the term "halo" refers to —F, —Cl, —Br, and —I as substituents.

The term "heteroaryl," as used herein, refers to a cyclic aromatic group having five or six ring atoms wherein at least one ring atom is selected from the group consisting of oxygen, sulfur, and nitrogen, and the remaining ring atoms are carbon. Heteroaryl groups of this invention include those derived from furan, imidazole, isothiazole, isoxazole, oxazole, pyrazine, pyrazole, pyridazine, pyridine, pyrimidine, pyrrole, quinoline, thiazole, 1,3,4-thiadiazole, triazole, and tetrazole.

The term "heteroarylene," as used herein, refers to a bivalent cyclic aromatic group having five or six ring atoms wherein at least one ring atom is selected from the group consisting of oxygen, sulfur, and nitrogen, and the remaining ring atoms are carbon. The heteroarylene group can be optionally substituted.

The term "heteroatom," as used herein, refers to an oxygen, nitrogen or sulfur atom.

The term "heterocycloalkyl" as used herein, refers to a non-aromatic five-, six- or seven-membered ring or a bi- or tri-cyclic group having one or more heteroatoms independently selected from oxygen, sulfur and nitrogen wherein each 5-membered ring has zero to one double bonds and each six-membered ring has zero to 2 double bonds. The nitrogen and sulfur heteroatoms can optionally be oxidized, the nitrogen heteroatom can optionally be quaternized, and any of the above heterocyclic rings can be fused to an aryl or heteroaryl ring. Representative heterocycles include, but are not limited to: pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, morpholinyl, isothiazolidinyl, and tetrahydrofurranyl. The heterocycloalkyl groups of this invention can be optionally substituted with one, two, or three substituents independently selected from —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, -cycloalkyl, -cycloheteroalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

The term "heterocycloalkylene" as used herein, refers to a bivalent non-aromatic five-, six- or seven-membered ring having one or more heteroatoms independently selected from oxygen, sulfur and nitrogen wherein each 5-membered ring has zero to one double bonds and each six-membered ring has zero to 2 double bonds. The heterocycloalkylene groups of this invention can be optionally substituted.

The term "hydroxyl," as used herein, refers to —OH.

The term "nitroheteroaryl," as used herein, refers to a cyclic aromatic, or a fused bicyclic aromatic group having five to ten ring atoms wherein at least one ring atom is selected from the group consisting of oxygen, sulfur, and nitrogen, and the remaining ring atoms are carbon. Nitroheteroaryl group of this invention is optionally substituted with one to three substituents in addition to the nitro group (—NO$_2$). The examples of nitroheteroaryl include those derived from nitrofuran, nitroimidazole, nitroisothiazole, nitroisoxazole, nitrooxazole, nitropyrazine, nitropyrazole, nitropyridazine, nitropyridine, nitropyrimidine, nitropyrrole, nitroquinoline, nitrothiazole, nitroimidazooxazole, nitroimidazooxazine.

The term "protecting group", as used herein, refers to an easily removable group which are known in the art to protect a functional group, such as hydroxyl and amino, against undesirable reaction during synthetic procedures and to be selectively removable. The use of protecting groups is well-known in the art for protecting groups against undesirable reactions during a synthetic procedure and many such protecting groups are known (T. H. Greene and P. G. M. Wuts, *Protective Groups in Organic Synthesis*, 2nd edition, John Wiley & Sons, New York, 1991).

The term "substituted aryl," as used herein, refers to an aryl group, as defined herein, substituted by independent replacement of one, two or three of the hydrogen atoms with —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, -cycloalkyl, -heterocycloalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

The term "substituted heteroaryl" as used herein refers to a heteroaryl group as defined herein substituted by independent replacement of one, two or three of the hydrogen atoms with —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, -cycloalkyl, -heterocycloalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

The term "substituted heterocycloalkyl," as used herein, refers to a heterocycloalkyl group, as defined above, substituted by independent replacement of one, two or three of the hydrogen atoms with —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, -cycloalkyl, -heterocycloalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

The term "substituent," as used herein, refers to —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$- aryl, —NHCO₂-heteroaryl, —NHC(O)NH₂, —NHC(O)NH-alkyl, —NHC(O)NH-aryl, —NHC(O)NH-heteroaryl, —SO₂-alkyl, —SO₂-aryl, —SO₂-heteroaryl, —SO₂NH₂, —SO₂NH-alkyl, —SO₂NH-aryl, —SO₂NH-heteroaryl, -alkyl, -cycloalkyl, -heterocycloalkyl, —CF₃, —CH₂OH, —CH₂NH₂, -aryl, -heteroaryl, -benzyl, -benzyloxy, -aryloxy, -heteroaryloxy, -alkoxy, -methoxymethoxy, -methoxyethoxy, -amino, -benzylamino, -arylamino, heteroarylamino, -alkylamino, -thio, -arylthio, -heteroarylthio, -benzylthio, -alkylthio, or -methylthiomethyl.

The present invention is directed to rifamycin-nitroheteroaryl hybrids of structural formula (I) as defined below:

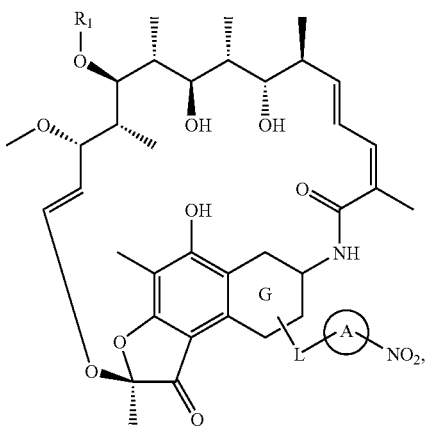

I or their pharmaceutically acceptable salt thereof, wherein R₁ is a hydrogen or acetyl group, G is a structure of formula II, III, IV or V:

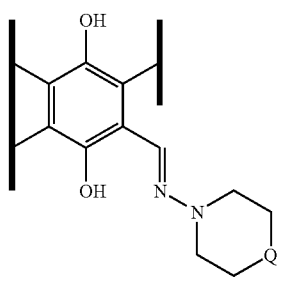

II

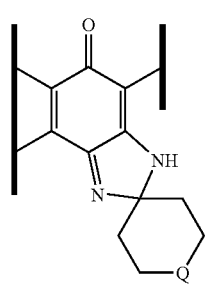

III

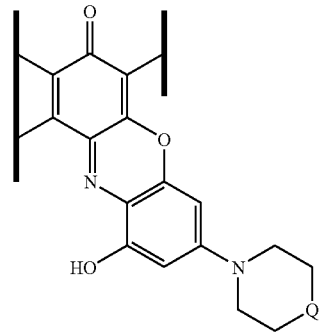

IV

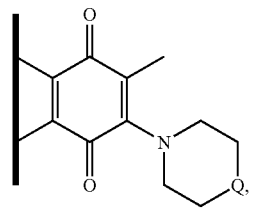

V wherein, in formula II, III, IV or V, Q is N— or CR₂—, which is bonded to a linkage group "L", which in turn is bonded to a structure

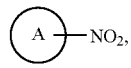

and R₂ is a group selected from hydrogen, substituted or unsubstituted (C₁-C₆)alkyl, aryl, heteroaryl, or heterocycloalkyl group;

L is a bond, or a linker group selected from one or a combination of two to five of the following groups:
1) (C₁-C₆)alkylene,
2) (C₃-C₈)cycloalkylene,
3) arylene,
4) heteroarylene,
5) heterocycloalkylene containing 1 to 3 heteroatoms,
6) —C(=O)—,
7) —C(=N—O—R₃)—,
8) —C=N—,
9) —O—,
10) —S(O)ₙ—, wherein n is number between 0 and 2,
11) —N(R₄)—,
wherein the carbon or nitrogen atoms of the linker group are optionally substituted by 1 to 3 substituents selected from (C₁-C₆)alkyl, substituted (C₁-C₆)alkyl, amino, (C₁-C₆)alkylamino, di(C₁-C₆)alkylamino, hydroxyl, (C₁-C₆)alkoxy or heterocycloalkyl group; R₃ and R₄ are independently a group selected from hydrogen, substituted or unsubstituted (C₁-C₆)alkyl, aryl, heteroaryl or heterocycloalkyl group; and structure

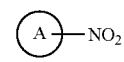

is a structural formula VI, VII, VIII or IX:

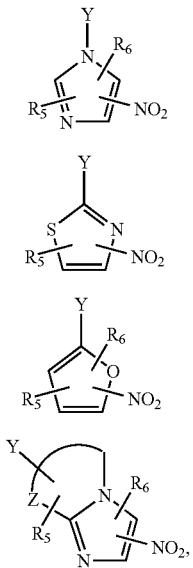

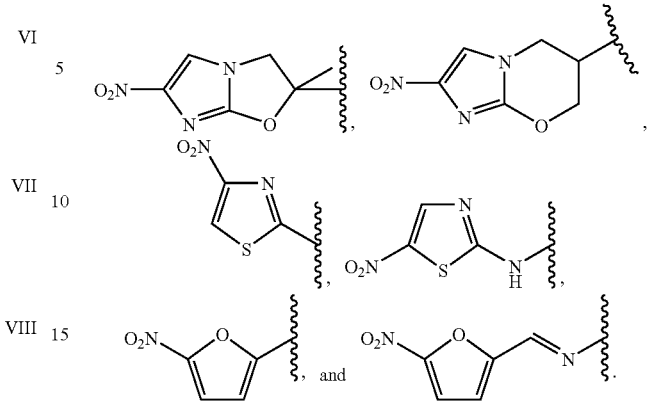

wherein Y is a bond which is bonded to linkage group "L", defined as above; and Z is a carbon (—CR$_7$R$_8$—), carbonyl (—C(O)—), amide (—C(O)N—), sulfonamide (—S(O$_2$)N—), or a heteroatom selected from N, O, S, SO or SO$_2$; wherein R$_5$, R$_6$, R$_7$, and R$_8$ are independently a group selected from hydrogen, substituted or unsubstituted (C$_1$-C$_6$)alkyl, aryl, heteroaryl, or heterocycloalkyl group; R$_5$ and R$_6$, R$_7$ and R$_8$ can join together to form a five to seven-member ring system optionally containing one to three heteroatoms.

Preferred compounds of the invention of formula (I) are those wherein:

L is a bond or a group selected from one or a combination of two to three groups of:
1) (C$_1$-C$_6$)alkylene,
2) (C$_3$-C$_8$)cycloalkylene,
3) heterocycloalkylene containing 1 to 3 heteroatoms,
4) —C(=O)—,
5) —O—, and
6) —N(R$_4$)—, wherein R$_4$ is selected from hydrogen, substituted or unsubstituted (C$_1$-C$_6$)alkyl, aryl, heteroaryl, and heterocycloalkyl group.

More preferred compounds of the invention are those wherein L is as stated above, and the structure

is selected from the group:

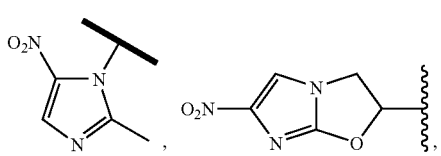

Most preferred compounds of the present invention include: 4-Deoxy-3,4-[2-spiro-[1-[2-(2-methyl-5-nitro-imidazol-1-yl)ethyl]-piperidin-4-yl]]-(1H)-imidazo-(2,5-dihydro) rifamycin S; 4-Deoxy-3,4-[2-spiro-[1-[(5-nitro-thiazol-2-ylcarbamoyl)-methyl]-piperidin-4-yl]]-(1H)-imidazo-(2, 5-dihydro)rifamycin S; 3'-Hydroxy-5'-[4-[2-(2-methyl-5-nitro-imidazol-1-yl)ethyl]-1-piperazinyl]benzoxazinorifamycin; 3-[[[4-[2-(2-methyl-5-nitro-imidazol-1-yl)ethyl]-1-piperazinyl]imino]methyl]rifamycin SV; 4-Deoxy-3,4-[2-spiro-[1-(2-methyl-6-nitro-2,3-dihydro-imidazo[2,1-b]oxazol-2-ylmethyl)-piperidin-4-yl]]-(1H)-imidazo-(2,5-dihydro)rifamycin S; 3-{4-[4-(6-Nitro-2,3-dihydro-imidazo[2,1-b]oxazol-2-ylmethoxy)-benzyl]-piperazin-1-yl}rifamycin S; 4-Deoxy-3,4-[2-[4-(6-nitro-2,3-dihydro-imidazo[2,1-b]oxazol-2-ylmethoxy)-phenyl]]-(1H)-imidazo-rifamycin SV; 3-{4-[4-(2-Methyl-6-nitro-2,3-dihydro-imidazo[2,1-b]oxazol-2-ylmethoxy)-benzoyl]-piperazin-1-yl}rifamycin S; 4-Deoxy-3,4-[2-spiro-[1-[4-[6S-(2-nitro-6,7-dihydro-5H-imidazo[2,1-b][1,3]oxazin-6-yloxymethyl)]-benzyl]-piperidin-4-yl]]-(1H)-imidazo-(2,5-dihydro) rifamycin S; 3-{4-[4-[(6S)-(2-Nitro-6,7-dihydro-5H-imidazo[2,1-b][1,3]oxazin-6-yloxymethyl)]-benzyl]-piperazin-1-yl}rifamycin S; 3-{4-[4-(2-Methyl-6-nitro-2,3-dihydro-imidazo[2,1-b]oxazol-2-ylmethoxy)-benzyl]-piperazin-1-yl}rifamycin S; 3'-Hydroxy-5'-[4-[4-(6S-2-nitro-6,7-dihydro-5H-imidazo[2,1-b][1,3]oxazin-6-yloxymethyl)-benzyl]-1-piperazinyl]benzoxazinorifamycin; 4-Deoxy-3,4-[2-spiro-[1-[3-(6S-2-nitro-6,7-dihydro-5H-imidazo[2,1-b][1,3]oxazin-6-yloxymethyl)]-benzyl]-piperidin-4-yl]]-(1H)-imidazo-(2,5-dihydro)rifamycin S; 3-{4-[3-(6S-(2-Nitro-6,7-dihydro-5H-imidazo[2,1-b][1,3]oxazin-6-yloxymethyl)]-benzyl]-piperazin-1-yl}rifamycin S; 3'-Hydroxy-5'-[4-[3-(6S-2-nitro-6,7-dihydro-5H-imidazo[2, 1-b][1,3]oxazin-6-yloxymethyl)-benzyl]-1-piperazinyl]benzoxazinorifamycin; 3-[[[4-[4-(6S-2-Nitro-6,7-dihydro-5H-imidazo[2,1-b][1,3]oxazin-6-yloxymethyl)-benzyl]-piperazin-1-yl]imino]methyl]rifamycin SV; 4-Deoxy-3,4-[2-spiro-[1-[[4-(6S-2-nitro-6,7-dihydro-5H-imidazo[2,1-b][1,3]oxazin-6-yloxymethyl)-phenoxy]-acetyl]-piperidin-4-yl]-(1H)-imidazo-(2,5-dihydro)rifamycin S; 3-[4-[1-[4-(6S-2-Nitro-6,7-dihydro-5H-imidazo[2,1-b][1,3]oxazin-6-yloxymethyl)-benzyl]-1H-[1,2,3]triazol-4-ylmethyl]-piperazin-1-yl]-rifamycin S; 3'-Hydroxy-5'-[4-[1-[4-(6S-2-nitro-6,7-dihydro-5H-imidazo[2,1-b][1,3]oxazin-6-yloxymethyl)-benzyl]-1H-[1,2,3]triazol-4-ylmethyl]-piperazin-1-yl]-benzoxazinorifamycin; 3'-Hydroxy-5'-{4-[4-(2-methyl-6-nitro-2,3-dihydro-imidazo[2,1-b]oxazol-2-ylmethoxy)-phenyl]-piperazin-1-yl}-benzoxazinorifamycin;

3-(2-{4-[4-(2-Methyl-6-nitro-2,3-dihydro-imidazo[2,1-b] oxazol-2-ylmethoxy)-phenyl]-piperazin-1-yl}) Rifamycin S; 3-[4-(2-{4-[4-(2-methyl-6-nitro-2,3-dihydro-imidazo[2,1-b] oxazol-2-ylmethoxy)-phenyl]-piperazin-1-yl}-acetyl)-piperazin-1-yl]-rifamycin S; 4-Deoxy-3,4-[2-spiro-[1-[2-(2-nitro-6,7-dihydro-5H-imidazo[2,1-b][1,3]oxazin-6-yloxy)-acetyl]-piperidin-4-yl]]-(1H)-imidazo-(2,5-dihydro) rifamycin S; 2-[4-(2-Bromo-4-nitro-imidazol-1-ylmethyl)-4-hydroxy-piperidin-1-yl]-rifamycin S; 3-{4-[2-(6S-2-Nitro-6,7-dihydro-5H-imidazo[2,1-b][1,3]oxazin-6-yloxy)-acetyl]-piperazin-1-yl}-rifamycin S; and 3-[4-(2-Methyl-6-nitro-2,3-dihydro-imidazo[2,1-b]oxazol-2-ylmethyl)-piperazin-1-yl]rifamycin S.

The substituted rifamycin derivatives of the present invention can be prepared by the following general synthetic schemes.

Scheme 1, shown in FIG. 1, illustrates a general method of synthesizing nitroimidazole-, nitrothiazole-, or nitrofuran-substituted 3-hydrazono-rifamycin (IIA). Nitroimidazole-, nitrothiazole-, or nitrofuran-substituted carboxaldehyde (1a) is reductively aminated using a reducing agent, such as sodium triacetoxyborohydride, in organic solvent, such as dichloromethane in the presence of acetic acid, with a protected piperazine (1b), such as 1-BOC-piperazine, to give compound (1c). The protecting group is removed under deprotection conditions, such as TFA, to give compound (1d). Compound (1d) is treated with an aminating agent, such as hydroxylamine-O-sulfuric acid in aqueous sodium hydroxide, to give hydrazine compound (1e). Coupling of compound (1e) with 3-formylrifamycin (1f) in organic solvent under mild acidic conditions, such as THF or methanol or a mixture of them, in the presence of acetic acid, produces 3-hydrazono-rifamycin (IIA). Alternative method of generating compound (1e) is by reductive amination of compound (1g) as described before, followed by acid mediated hydrolysis of trifluoro-acetyl group. Alternative method of generating 3-hydrazono-rifamycin (IIA) is going through intermediate (1h), which is prepared by coupling of the piperazine monohydrazine and 3-formylrifamycin (1f). The compound (1h) is alkylated with a nitroimidazole-, nitrothiazole-, or nitrofuran-substituted halide or other leaving groups (1i) to produce compounds of the invention (IIA).

Figure 2:
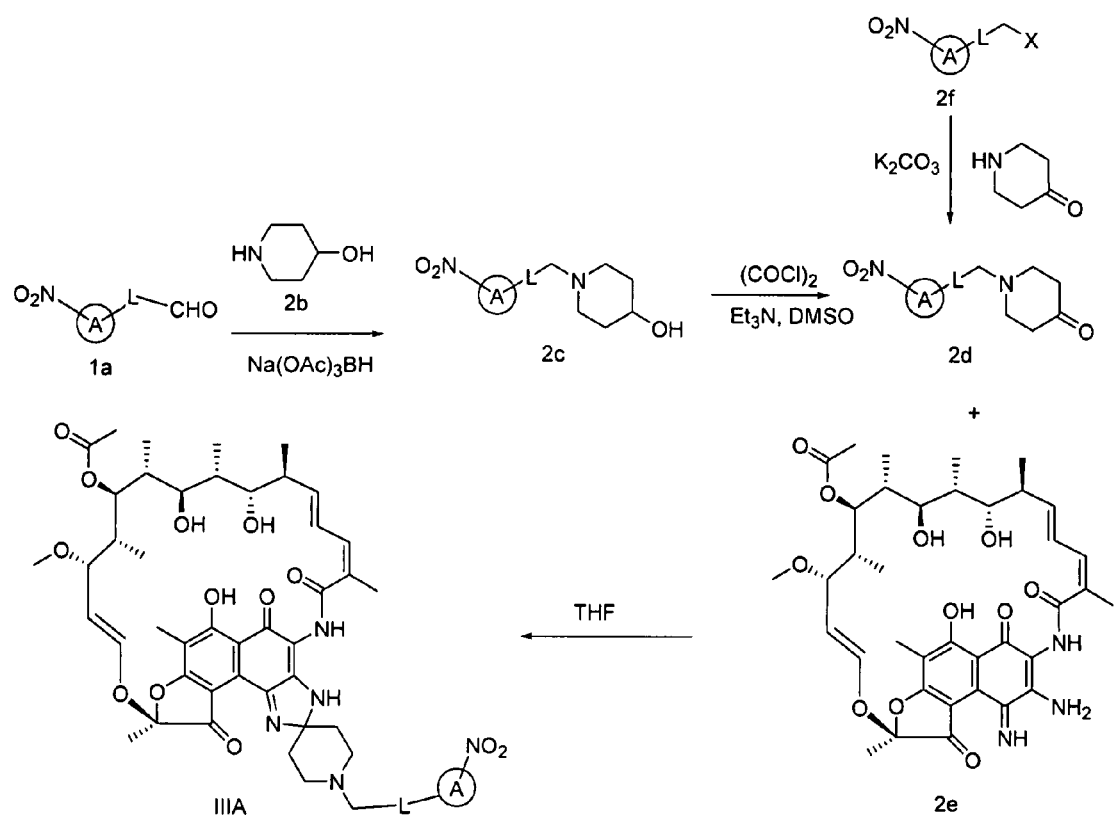
FIG. 2 shows Scheme 2, a general method of synthesizing nitroimidazole-, nitrothiazole-, or nitrofuran-substituted 3,4-hydroazono-rifamycin.

Scheme 2, shown in FIG. 2, illustrates a general method of synthesizing nitroimidazole-, nitrothiazole-, or nitrofuran-substituted 3,4-hydrazono-rifamycin (IIIA). Nitroimidazole-, nitrothiazole-, or nitrofuran-substituted carboxaldehyde (1a) is reductively aminated using a reducing agent, such as sodium triacetoxyborohydride, in organic solvent, such as dichloromethane in the presence of acetic acid, with 4-hydroxypiperidine (2b), to give compound (2c). Compound (2c) is oxidized by an oxidant, such as oxalyl chloride, triethylamine in DMSO and dichloromethane, to give 4-piperidone compound (2d). This compound (2d) is coupled with 3-amino-4-deoxy-4-imino-rifamycin, which is prepared by a known procedure, in organic solvent, such as THF, to give 3,4-hydrazono-rifamycin (IIIA). Alternative method of producing substituted 4-piperidone (2d) is going through displacement reaction of 4-piperidone with a nitroimidazole-, nitrothiazole-, or nitrofuran-substituted halide or other leaving groups (1f), which is carried out in organic solvent, such as THF or DMF, in the presence of a base, such as potassium carbonate.

Figure 3:
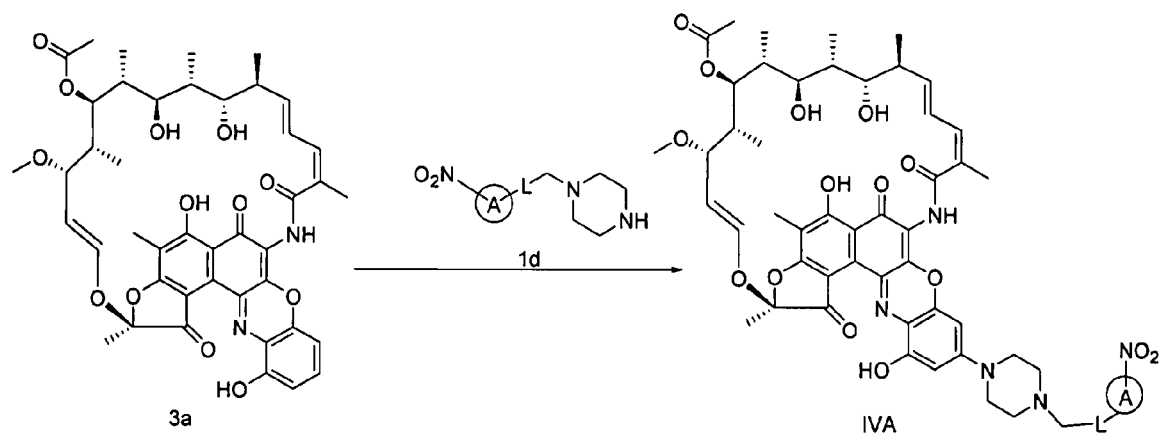
FIG. 3 shows Scheme 3, a general method of synthesizing nitroimidazole-, nitrothiazole-, or nitrofuran-substituted 3,4-benzooxazino-rifamycin.

Scheme 3, shown in FIG. 3, illustrates a general method of synthesizing nitroimidazole-, nitrothiazole-, or nitrofuran-substituted 3,4-benzooxazino-rifamycin (IVA). Compound (1d) prepared as illustrated in scheme 1 is reacted with 3,4-benzooxazino-rifamycin, prepared by a known procedure, in a organic solvent, such as DMSO, in the presence of an oxidant, such as $MnO_2$ to give 3,4-benzooxazino-rifamycin (IVA). Compound (1d) may also be prepared by other known methods by the one who is skilled in the art.

Figure 4:
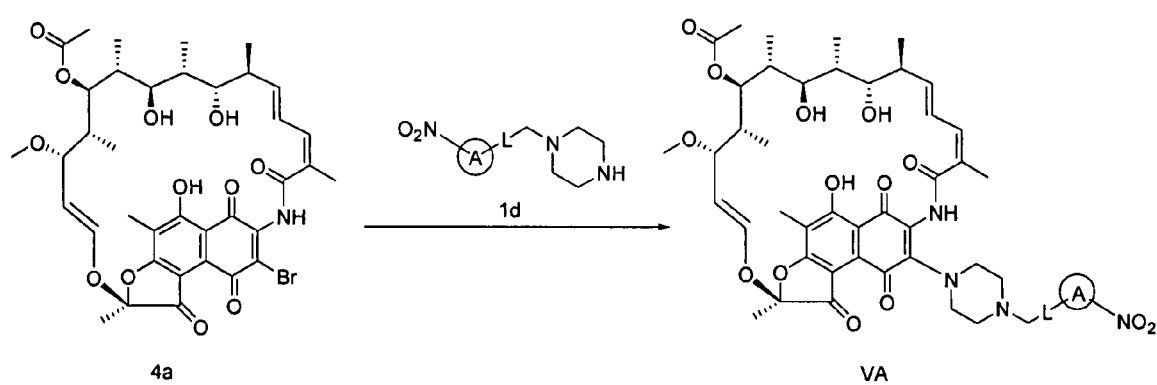
FIG. 4 shows Scheme 4, a general method of synthesizing nitroimidazole-, nitrothiazole-, or nitrofuran-substituted rifamycin S.

Scheme 4, shown in FIG. 4, illustrates a general method of synthesizing nitroimidazole-, nitrothiazole-, or nitrofuran-substituted rifamycin S (VA). Compound (1d) prepared as illustrated in scheme 1 is reacted with 3-bromo-rifamycin, prepared by a known procedure, in a organic solvent, such as THF, in the presence of a base, like sodium bicarbonate, or organic base, like triethylamine to give the inventive compounds (VA).

Nitroimidazole-, nitrothiazole-, or nitrofuran-substituted carboxaldehyde (1a) or their ketones can be prepared through variety of syntheses. The preferred route is through oxidation of their alcohols using an oxidant, such as oxalyl chloride in DMSO in the presence of triethylamine.

The above syntheses schemes are preferred schemes for the synthesis of nitroimidazole-, nitrothiazole-, or nitrofuran-substituted rifamycin derivatives of formula (I). It is apparent to one skilled in art that other sequence of the reaction, and alternative reagents can be used for the synthesis of the inventive rifamycin derivative. These alternatives for the synthesis of the inventive rifamycin derivatives are within the scope of this invention.

The nitroimidazole-, nitrothiazole-, or nitrofuran-substituted rifamycin derivatives of formula (I) of the present invention contain chiral centers. The rifamycin portion of the inventive compounds are derived from the natural product rifamycin, and therefore inherit chirality. The linkage group "L" and nitroheteroaryl pharmacophore may contain one or more chiral centers. It is apparent to one skilled in the art that when one chiral center is present in either "L" or nitroheteroaryl pharmacophore, the chiral center can exist as one of two possible optical configurations ((R) and (S)). The resulting rifamycin derivative of the formula (I) can exist as one of the two possible diastereomers resulting from the two possible optical configurations, or a diastereomeric mixture of both. When two chiral centers are present, four possible diastereomers are possible, and so on and so forth. Both individual diastereomers and as well as mixtures thereof, are within the scope of the nitroimidazole-, nitrothiazole-, or nitrofuran-substituted rifamycin derivatives of formula (I) of the invention. In the event a second chiral center is present, the resultant diastereomers, in racemic and enantiomerically enriched forms, also are within the scope of the compounds of the invention.

The preferred compounds of the present invention are optically pure diastereomers having the (S) or (R)-configuration in either the "L" or nitroheteroaryl pharmacophore. It is known in the art that one diastereomer is superior to the other in activity. However, the racemic mixture also is useful, but a greater amount of the racemic material may be required to produce the same effect as the pure diastereomer.

If desired, the mixture of pure diastereomer is resolved by means known to those skilled in the art. Single pure material can be obtained by resolution of the diastereomeric mixture by HPLC. Alternatively, resolution of the racemic mixture can be accomplished by selective crystallization of a salt form using methods known to those skilled in the art.

A compound of formula (I), or a prodrug or a physiologically acceptable salt or solvate thereof, can be administered as the neat compound or as a pharmaceutical composition containing either entity.

The pharmaceutical compositions of the present invention can be prepared by admixing a compound of formula (I) with a solid or liquid pharmaceutically acceptable carrier, and, optionally, with pharmaceutically acceptable adjuvants and excipients employing standard and conventional techniques. Solid form compositions include powders, tablets, dispersible granules, capsules, cachets and suppositories. A solid carrier can be at least one substance, which also can function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, a low melting wax, cocoa butter, and the like. Liquid form compositions include solutions, suspensions, and emulsions. For example, compounds of the present invention can be dissolved in water, water-propylene glycol, or water-polyethylene glycol, optionally containing suitable conventional coloring agents, flavoring agents, stabilizers and thickening agents. The inventive rifamycin derivatives of formula (I) can be used alone, or in conjunction with other antibacterial agents and/or non-antibacterial agents, as known to those skilled in the art.

"Pharmaceutically acceptable" refers to those properties and/or substances which are acceptable from a pharmacological or toxicological point of view and from a physical or chemical point of view regarding composition, formulation, stability, patient acceptance, and bioavailability. Pharmaceutically acceptable hydrate means hydrates useful for administering the compounds of this invention, and suitable hydrates include the compounds complexed with at least one water molecule.

Pharmaceutically acceptable salts means salts useful for administering compounds of the present invention. Suitable salts include acid addition salts when a basic group is present, such as occurs with a piperazinyl, or piperidinyl, or pyrrolidinyl group and the like, heteroaryls, such as imidazolyl, pyridinyl. Acid addition salts include those made from mineral acids, for example, hydrochloric, hydrobromic, hydroiodic, sulfuric, phosphoric, and the like, organic sulfonic acids, e.g., methanesulfonic, 2-hydroxyethyl sulfonates, organic carboxylic acids, e.g., amino and carbohydrate acids, e.g., gluconic, galacturonic, acetates, propionates, lactates, maleates, malates, succinates, tartrates, citric acid, fumarates, and the like. These salts can be in a hydrated form.

Pharmaceutically acceptable prodrugs means prodrugs useful for administering the compounds of this invention, and metabolized in vivo to give pharmaceutically active forms of the inventive compounds of formula (I). Suitable prodrugs include acid derivatives, for example, amides, esters, for example, methyl esters, ethyl esters, and the like. These prodrugs also can be in a hydrated form.

Compounds and pharmaceutical compositions suitable for use in the present invention include those wherein the active ingredient is administered in an effective amount to achieve its intended purpose. More specifically, a "therapeutically effective amount" means an amount effective to prevent development of, or to alleviate the existing symptoms of, the subject being treated. Determination of the effective amounts is well within the capability of those skilled in the art, especially in light of the detailed disclosure provided herein.

A "therapeutically effective dose" refers to that amount of the compound that results in achieving the desired effect. Toxicity and therapeutic efficacy of such compounds can be determined by standard pharmaceutical procedures in cell cultures or experimental animals, e.g., for determining the $LD_{50}$ (the does lethal to 50% of the population) and the $ED_{50}$ (the dose pharmacologically effective to 50% of the population). The dose ratio between toxic and therapeutic effects is the therapeutic index, which is expressed as the ratio between $LD_{50}$ and $ED_{50}$. Compounds exhibiting high therapeutic indices are preferred. The data obtained can be used in formulating a dosage range for use in humans. The dosage of such compounds preferably lies within a range of circulating concentrations that include the $ED_{50}$ with little or no toxicity. The dosage can vary within this range depending upon the dosage form employed, and the route of administration utilized.

Humans and other mammals, for example, cattle, horses, sheep, hogs, dogs, and cats, can be treated with the inventive rifamycin derivatives of the present invention. The rifamycin derivatives of the present invention can be administered in a manner and in dosage forms similar to those of the known anti-bacterial agents described above. In therapeutic use for treating, or combating, bacterial infections in humans and warm-blooded animals, the compounds of formula (I), or pharmaceutical compositions thereof, are administered by conventional techniques, such as orally in solid and liquid dosage forms and/or parenterally (IV, IM, SC), at a unit dosage form to obtain and maintain a concentration, that is, an amount, or blood-level of active component in the animal undergoing treatment which is antibacterially effective or appropriate.

Generally, the amount of the compounds of formula (I) in a pharmaceutical composition is about 0.5% to about 90% by weight. An antibacterially effective dosage of the compounds of formula (I) is about 0.1 to about 100 mg/kg of body weight/day, more preferably about 3 to about 50 mg/kg of body weight/day. The quantity of the rifamycin derivatives of formula (I) in the pharmaceutical composition, the exact unit dosage form thereof to be administered, the frequency of administration, and the route of administration will vary, and can be adjusted widely depending upon a number of factors known to those skilled in the art including the particular mode of administration, the particular compound being used, the potency of the particular compound, the desired concentration, the age, weight, sex, and general physical condition and requirements of the patient, the nature and severity of the bacterial infection being treated, and the like, as is well known to the physician treating infectious diseases. Also, it is to be understood that the initial dosage administered can be increased beyond the above upper level in order to rapidly achieve the desired blood-level or the initial dosage can be smaller than the optimum and the daily dosage can be progressively increased during the course of treatment depending on the particular situation. The usual pharmaceutical dosage forms appropriate for parenteral (mixture, suspension in oil) and oral (tablet, capsule, syrup, suspension, etc) administration are known to those skilled in the art.

Compounds of the present invention can be administered by any suitable route, for example by oral, topical, buccal, inhalation, sublingual, rectal, vaginal, transurethral, nasal, topical, percutaneous, i.e., transdermal, or parenteral (including intravenous, intramuscular, subcutaneous, and intracoronary) administration. Parenteral administration can be accomplished using a needle and syringe, or infused together with an IV fluid, like 5% dextrose or normal saline.

If the compounds or pharmaceutical compositions of the present invention are administered parenterally, i.e., by injection, for example, by intravenous injection or by other parenteral routes of administration, it generally is as a soluble salt (acid addition salt or base salt) of the compound according to formula (I) in a pharmaceutically acceptable amount dissolved in a pharmaceutically acceptable liquid carrier such as, for example, water-for-injection, and a buffer to provide a suitable buffered isotonic solution, for example, having a pH of about 3.5 to about 10.

Suitable-buffering agents include, for example, trisodium orthophosphate, sodium bicarbonate, sodium citrate, N-methylglucamine, L(+)-lysine, and L(+)-arginine. A compound of formula (I) generally is dissolved in the carrier in an amount sufficient to provide a pharmaceutically acceptable injectable concentration in the range of about 1 to about 400 mg/ml of solution. The resulting liquid pharmaceutical composition is administered so as to obtain the above-mentioned antibacterially effective amount of dosage.

For human use, a compound of the formula (I) can be administered alone, but generally is administered in admixture with a pharmaceutical carrier selected with regard to the intended route of administration and standard pharmaceutical practice. Pharmaceutical compositions for use in accordance with the present invention can be formulated in a conventional manner using one or more physiologically acceptable carriers comprising excipients and auxiliaries that facilitate processing of compounds of formula (I) into preparations which can be used pharmaceutically.

These pharmaceutical compositions can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen. When a therapeutically effective amount of a compound of the present invention is administered orally, the composition typically is in the form of a tablet, capsule, powder, solution, or elixir. When administered in tablet form, the composition can additionally contain a solid carrier, such as a gelatin or an adjuvant. The tablet, capsule, and powder contain about 5 to about 95% compound of the present invention, and preferably from about 25 to about 90% compound of the present invention. When administered in liquid form, a liquid carrier such as water, petroleum, or oils of animal or plant origin can be added. The liquid form of the composition can further contain physiological saline solution, dextrose or other saccharide solutions, or glycols. When administered in liquid form, the composition contains about 0.5 to about 90% by weight of a compound of the present invention, and preferably about 1 to about 50% of a compound of the present invention.

For oral administration, the compounds can be formulated readily by combining a compound of formula (I) with pharmaceutically acceptable carriers well known in the art. Such carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound of formula (I) with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added.

For administration by inhalation, compounds of the present invention can be delivered in the form of an aerosol spray presentation from pressurized packs or a nebulizer, with the use of a suitable propellant. In the case of a pressurized aerosol, the dosage unit can be determined by providing a valve to deliver a metered amount. Capsules and cartridges, e.g., gelatin capsules, for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils or synthetic fatty acid esters. Aqueous injection suspensions can contain substances, which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the present invention also can be formulated in rectal compositions, such as suppositories or retention enemas, e.g., containing conventional suppository bases. In addition to the formulations described previously, the compounds also can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

For topical administration, the present compounds can be applied in neat form, e.g., when the compound is a liquid. However, it is desirable to administer the compounds to the skin as compositions in combination with a dermatologically acceptable carrier, which can be a solid, semi-solid, or a liquid. Useful solid carriers include, but are not limited to, finely divided solids such as talc, clay, microcrystalline cellulose, silica, alumina, and the like. Useful liquid carriers include, but are not limited to, water, alcohols, glycols, and water-alcohol/glycol blends in which the present compounds can be dissolved or dispersed at effective levels, optionally with the aid of a surfactant. Adjuvants, such as fragrances and additional antimicrobial agents, can be added to optimize the properties for a given use. The resultant liquid compositions can be applied topically by absorbent pads, used to impregnate bandages and other dressings, or sprayed onto the affected area using pump-type or aerosol sprayers. For veterinary use, a compound of formula (I) or a nontoxic salt thereof, is administered as a suitably acceptable formulation in accordance with normal veterinary practice. The veterinarian can readily determine the dosing regimen and route of administration that is most appropriate for a particular animal.

GENERAL METHODS AND DEFINITIONS

All starting material used in these examples are either purchased from commercial sources or prepared according to published procedures. Reagents were purchased from commercial sources and used without further purification. All temperatures are in degrees Centigrade. When solvent pairs are used, the ratios of solvents used are volume/volume (v/v). When the solubility of a solid in a solvent is used the ratio of the solid to the solvent is weight/volume (wt/v). Reactions with moisture-sensitive reagents were performed under a nitrogen atmosphere. Concentration of solutions was performed by reduced pressure (in vacuo) rotary evaporation. Flash chromatography is performed using silica gel 60 as normal phase adsorbent or C18 silica gel as reverse phase adsorbent. Thin layer chromatography ("TLC") is performed using pre-coated plates purchased from E. Merck and spots are visualized with long-wave ultraviolet light followed by an appropriate staining reagent. Preparative thin-layer chromatography (TLC) was performed using EM silica gel (SG) 60 $F_{254}$ plates (20×20 cm, thickness 2 mm), bands are visualized with long-wave ultraviolet light lamp. Nuclear magnetic resonance ("NMR") spectra are recorded on a Varian 400 MHz magnetic resonance spectrometer. $^1$H NMR refers to proton nuclear magnetic resonance spectroscopy with chemical shifts reported in ppm downfield from tetramethylsilane or using the residual solvent signal (CHCl$_3$=δ 7.27, CH$_3$OH=δ 3.31) as internal standard. $^1$H NMR information is tabulated in the following format: number of protons, multiplicity (s, singlet; d, doublet; t, triplet; q, quartet; m, multiplet; td, triplet of doublet; dt, doublet of triplet), coupling constant (s) (j) in hertz. The prefix app is occasionally applied in cases where the true signal multiplicity is unresolved and prefix br indicates a broad signal. Electrospray ionization mass spectra are recorded on a Finnegan LCQ advantage spectrometer and reported as M+H or M+Na, referring to protonated molecular ion or its sodium complex.

ABBREVIATIONS

Abbreviations as used herein have the meanings known by one skilled in the art. Specifically, Ac represents acetyl group, BOC represents t-butoxycarbonyl group, Bn represents benzyl group, Bu represents butyl group, Bz represents benzoyl group, Cbz represents benzyloxycarbonyl group, DCM represents dichloromethane, DMAP represents 4-N,N-dimethylaminopyridine, DMF represents N,N-dimethylformamide, DMSO represents dimethyl sulfoxide, Et represents ethyl group, EtOAc represents ethyl acetate, Me represents methyl group, Ph represents phenyl group, Pr represents propyl group, TEA represents triethylamine, TFA represents trifluoroacetic acid, THF represents tetrahydrofuran, and TMS is trimethylsilyl group. The following abbreviations are also used: millimole (mmol), milliliter (mL), milligram (mg), microliter (μL).

EXAMPLES

The following examples describe how to prepare the various compounds and/or perform the various processes of the invention, and are to be construed as merely illustrative, and not limitations of the preceding disclosure in any way whatsoever. Those skilled in the art will recognize appropriate variations from the procedures both as to reagents and as to reaction conditions and techniques.

Example 1

4-Deoxy-3,4-[2-spiro-[1-[2-(2-methyl-5-nitro-imidazol-1-yl)ethyl]-piperidin-4-yl]]-(1H)-imidazo-(2,5-dihydro)rifamycin S

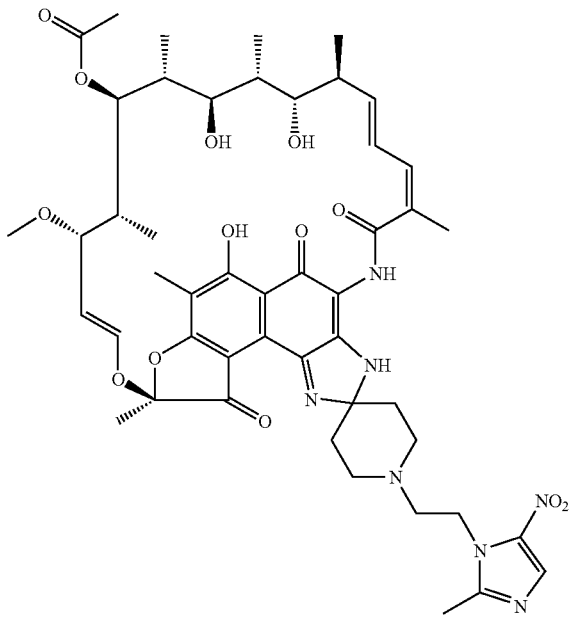

Step 1. (2-Methyl-5-nitro-imidazol-1-yl)-acetaldehyde (hydrate). To a stirred solution of anhydrous DMSO (51 mL, 719 mmol) in CH$_2$Cl$_2$ (350 mL) at −78° C. is added slowly 2 M oxalyl chloride in CH$_2$Cl$_2$ (35 mL) at −78° C. and allowed to stir for 20 min. A solution of 1-hydroxyethyl-2-methyl-5-nitroimidazole (metronidazole, 10 g, 58 mmol) in DMSO (50 mL) and CH$_2$Cl$_2$ (100 mL) is added to the reaction mixture and allowed to stir for 1 h at −78° C. Triethylamine (100 mL, 719 mmol) is added and allowed to stir for 1 h at −78° C. and the temperature was allowed to rise to room temperature. To the reaction mixture is mixed with water (200 mL) and mixture is extracted with CH$_2$Cl$_2$ (3×300 mL). The combined organic layer is dried over anhydrous Na$_2$SO$_4$, filtered and evaporated in vacuo. The residue is purified by silica gel column chromatography (3% MeOH in CH$_2$Cl$_2$) to give the crude title compound (10.5 g). $^1$H NMR (400 MHz, CDCl$_3$) δ 9.75 (s, 1H), 7.98 (s, 1H), 5.22 (s, 2H), 2.51 (s, 3H).

Step 2. 1-[2-(2-Methyl-5-nitro-imidazol-1-yl)-ethyl]-piperidin-4-ol. To a stirred solution of (2-methyl-5-nitro-imidazol-1-yl)-acetaldehyde (5.1 g) in CH$_2$Cl$_2$ are added 4-hydroxypiperidine (6.1 g, 60.4 mmol) and acetic acid (3.5 mL, 61 mmol) and allowed to stir for 1 h at room temperature. The reaction mixture is diluted with CH$_2$Cl$_2$ (20 mL) and methanol (10 mL), followed by the addition of NaBH(OAc)$_3$ (12.8 g, 60.4 mmol) and allowed to stir overnight at room temperature. To the mixture is added water (100 mL) and cooled to 0° C. and basified with the pellet of NaOH to pH>12. The mixture is extracted with 20% isopropyl alcohol in CH$_2$Cl$_2$ (200 mL). The combined organic layer is dried over anhydrous Na$_2$SO$_4$, filtered and evaporated. The residue is purified by silica gel column chromatography (10% MeOH in CH$_2$Cl$_2$) to give the title product (3.2 g, 42%). $^1$H NMR (400 MHz, CDCl$_3$) δ 7.93 (s, 1H), 4.38 (t, J=6.4 Hz, 2H), 3.70 (m, 1H), 2.75-2.70 (m, 4H), 2.65 (t, J=6.4 Hz, 2H), 2.51 (s, 3H), 2.25 (br t, J=10.0 Hz, 4H).

Step 3. 1-[2-(2-Methyl-5-nitro-imidazol-1-yl)-ethyl]-piperidin-4-one. To a stirred solution of anhydrous DMSO (0.85 mL, 12 mmol) in CH$_2$Cl$_2$ (15 mL) was added 2 M oxalyl chloride in CH$_2$Cl$_2$ (3 mL) at −78° C. and allowed to stir for 20 min. 1-[2-(2-Methyl-5-nitro-imidazol-1-yl)-ethyl]-piperidin-4-ol (1 g, 4 mmol) in CH$_2$Cl$_2$ (15 mL) is added and allowed to stir for 1 h at −78° C. Triethylamine (5.6 mL, 40 mmol) is added and allowed to stir for 1 h at −78° C. and warmed to room temperature. To the reaction mixture was added water (20 mL) and extracted with CH$_2$Cl$_2$ (3×100 mL). The combined organic layer is dried over anhydrous Na$_2$SO$_4$, filtered and evaporated. The residue was purified by silica gel column chromatography (6% MeOH in CH$_2$Cl$_2$) to give the title compound (481 mg, 48%). $^1$H NMR (400 MHz, CDCl$_3$) δ 7.95 (s, 1H), 4.46 (t, J=6.4 Hz, 2H), 2.81-2.77 (m, 6H), 2.54 (s, 3H), 2.41 (t, J=6.4 Hz, 4H).

Step 4. 4-Deoxy-3,4-[2-spiro-[1-[2-(2-methyl-5-nitro-imidazol-1-yl)ethyl]-piperidin-4-yl]]-(1H)-imidazo-(2,5-dihydro)rifamycin S. To a stirred solution of 1-[2-(2-methyl-5-nitro-imidazol-1-yl)-ethyl]-piperidin-4-one (2.7 g, 10.7 mmol) in THF (70 mL) is added 3-amino-4-deoxy-4-imino-rifamycin S (14 g, 19.7 mmol) prepared by following a literature report (U.S. Pat. No. 4,017,481) and allowed to stir for 2 min, then added ammonium acetate (3 g, 39 mmol) and allowed to stir for 4 h at room temperature. The mixture is diluted with ethyl acetate and washed with water and saturated brine. The organic layer is dried over anhydrous Na$_2$SO$_4$, filtered and evaporated. The residue is purified by silica gel column chromatography (7% MeOH in CH$_2$Cl$_2$) to give the title product (1.2 g, 12%) as dark purple solid. ESI MS m/z 944 (M+H$^+$); $^1$H NMR (400 MHz, CDCl$_3$) δ 14.64 (s, 1H), 8.89 (s, 1H), 8.24 (s, 1H), 7.97 (s, 1H), 6.37 (dd, J=10.4 Hz and 15.6 Hz, 1H), 6.27 (d, J=10.4 Hz, 1H), 6.16 (d, J=12.8 Hz, 1H), 6.01 (dd, J=15.6 Hz and 6.4 Hz, 1H), 5.12 (dd, J=12.4 Hz and 7.2 Hz, 1H), 4.75 (d, J=9.2 Hz, 1H), 4.51 (br s, 1H), 4.06 (t, J=6.8 Hz, 1H), 3.68-3.62 (m, 3H), 3.48 (s, 1H), 3.35-3.32 (m, 1H), 3.08 (s, 3H), 3.08-2.91 (m, 5H), 2.57 (s, 3H), 2.41-2.33 (m, 1H), 2.33 (s, 3H), 2.09-1.53 (m, 6H), 2.04 (s, 3H), 2.01 (s, 3H), 1.74 (s, 3H), 1.45-1.35 (m, 2H), 1.03 (d, J=6.8 Hz, 3H), 0.84 (d, J=7.2 Hz, 3H), 0.60 (d, J=6.4 Hz, 3H), −0.09 (d, J=6.8 Hz, 3H).

Example 2

4-Deoxy-3,4-[2-spiro-[1-[(5-nitro-thiazol-2-ylcarbamoyl)-methyl]-piperidin-4-yl]]-(1H)-imidazo-(2,5-dihydro)rifamycin S

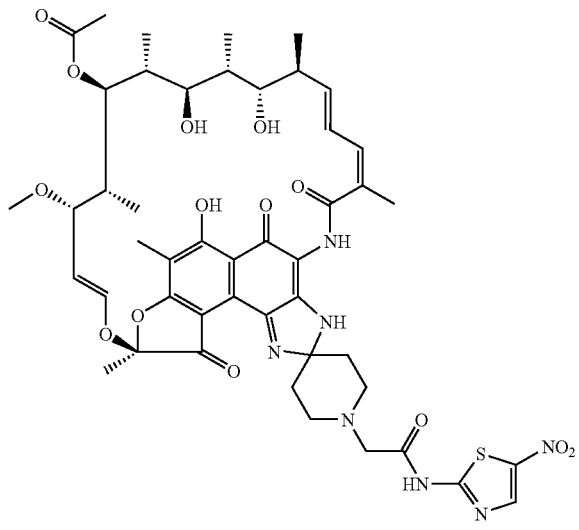

Step 1: Preparation of 2-Bromo-N-(5-nitro-thiazol-2-yl)-acetamide. To a stirred solution of 2-amino-5-nitrothiazole (725.7 mg) in ethyl acetate (50 mL) in the presence of saturated sodium carbonate (10 mL) at 0° C., is added bromoacetyl bromide (434.3 uL), and additional bromoacetyl bromide is added to complete the reaction. The organic layer is separated, washed with 3 N HCl solution, followed by brine and dried over sodium sulfate and concentrated in vacuo to give a brown oil. The crude product is purified by silica gel column chromatography (40% ethyl acetate/hexanes) to give a solid (950 mg). ESI MS m/z 266 (M+H$^+$); $^1$H NMR (400 MHz, CDCl$_3$) δ 8.26 (s, 1H), 3.98 (s, 2H).

Step 2. 1-[2-(2-Methyl-5-nitro-imidazol-1-yl)-ethyl]-piperidin-4-ol. To a stirred solution of 2-bromo-N-(5-nitro-thiazol-2-yl)-acetamide (100 mg) in THF in the presence of diisopropylethylamine (DIEA, 72 mg) is added 4-hydroxypiperidine (40 mg). The reaction mixture was allowed to stir at room temperature for 18 h. Water is added to the reaction mixture, and extracted with ethyl acetate. The organic extract is dried and concentrated to give a solid (60 mg). ESI MS m/z 287 (M+H$^+$); $^1$H NMR (400 MHz, CDCl$_3$) δ 8.27 (s, 1H), 3.28 (s, 2H), 2.80 (br s, 2H), 2.43 (br s, 2H), 1.88 (br s, 2H), 1.63 (br s, 2H).

Step 3. 1-[2-(2-Methyl-5-nitro-imidazol-1-yl)-ethyl]-piperidin-4-one. To a stirred solution of DMSO (87 mg) in dichloromethane at −78° C. under nitrogen is added oxalyl chloride (2 M, 0.28 mL). The resultant solution is allowed to stir at −78° C. for 20 min, a solution of 1-[2-(2-methyl-5-nitro-imidazol-1-yl)-ethyl]-piperidin-4-ol (107 mg) in dichloromethane is added, and allowed to stir for 1 h, triethylamine (520 uL) was added and allowed to stir for 1 h. The reaction mixture was allowed to warm up to room temperature, water is added, and portioned between water and dichloromethane. The organic layer is separated, dried over sodium sulfate and concentrated in vacuo to give a yellow solid (90 mg). ESI MS m/z 285 (M+H$^+$).

Step 4. 4-Deoxy-3,4-[2-spiro-[1-[(5-nitro-thiazol-2-ylcarbamoyl)-methyl]-piperidin-4-yl]]-(1H)-imidazo-(2,5-dihydro)rifamycin S. To a stirred solution of 1-[2-(2-Methyl-5-nitro-imidazol-1-yl)-ethyl]-piperidin-4-one (90 mg) and 3-amino-4-deoxy-4-imino-rifamycin S (112 mg) in THF is added Zinc (14.5 mg) and ammonium acetate (14.6 mg). The resultant mixture is allowed to stir at room temperature for 18 h. The mixture was partitioned between water and dichloromethane, and organic layer was separated, dried over sodium sulfate, and concentrated in vacuo to give a solid (130 mg). A portion of this is purified by Preparative TLC (10% methanol/dichloromethane) to give the title compound as a dark-red film (1.7 mg). ESI MS m/z 976 (M+H$^+$); $^1$H NMR (400 MHz, CDCl$_3$) δ 8.89 (s, 1H), 8.33 (s, 1H), 8.17 (s, 1H), 7.41 (br s, 1H), 6.35 (dd, J=7.9 Hz and 4.5 Hz, 1H), 6.25 (br s, 1H), 6.16 (d, J=8.5 Hz, 1H), 5.97 (d, J=12.5 Hz, 1H), 5.09 (d, J=8.8 Hz, 1H), 4.70 (s, 1H), 4.64 (s, 1H), 4.17 (d, J=3.2 Hz, 1H), 3.62-3.25 (complex pattern), 3.06 (s, 3H), 3.00 (br s, 1H), 2.40 (br s, 1H), 2.32 (s, 3H), 2.04 (br s, 2H), 2.02 (s, 3H), 1.98 (s, 3H), 1.75-1.22 (complex pattern), 1.02 (d, J=7.1 Hz, 3H), 0.91 (br s, 2H), 0.81 (d, J=6.9 Hz, 3H), 0.57 (d, J=7.3 Hz, 3H), −0.09 (d, J=6.3 Hz, 3H).

Example 3

3-[[[4-[2-(2-methyl-5-nitro-imidazol-1-yl)ethyl]-1-piperazinyl]imino]methyl]rifamycin SV

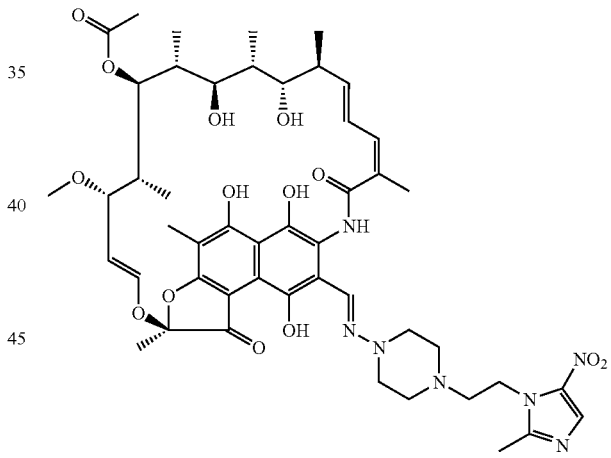

Step 1. 4-[2-(2-Methyl-5-nitro-imidazol-1-yl)-ethyl]-piperazine-1-carboxylic acid tert-butyl ester. To a stirred solution of (2-methyl-5-nitro-imidazol-1-yl)-acetaldehyde (2.2 g, 13 mmol) in THF (10 mL) are added N-Boc-piperazine (3.6 g, 19.4 mmol) and acetic acid (2.2 mL, 39 mmol) and allowed to stir for 1 h at room temperature, then added NaBH(OAc)$_3$ (7.2 g, 26 mmol) in THF (30 mL). The resulting reaction mixture is stirred overnight at room temperature. The mixture is diluted with ethyl acetate and washed with water and saturated brine. The organic layer is dried over anhydrous Na$_2$SO$_4$, filtered and evaporated. The residue was purified by silica gel column chromatography (3% MeOH in CH$_2$Cl$_2$) to give the title product (2.5 g, 59%). $^1$H NMR (400 MHz, CDCl$_3$) δ 7.93 (s, 1H), 4.42 (t, J=6.4 Hz, 2H), 3.39 (m, 4H), 2.68 (t, J=6.4 Hz, 2H), 2.51 (s, 3H), 2.46 (m, 4H), 1.44 (s, 9H).

Step 2. 1-[2-(2-Methyl-5-nitro-imidazol-1-yl)-ethyl]-piperazine. To a stirred solution of 4-[2-(2-methyl-5-nitro-imidazol-1-yl)-ethyl]-piperazine-1-carboxylic acid tert-butyl ester (2.5 g, 7.4 mmol) in CH$_2$Cl$_2$ (10 mL) is added trifluoroacetic acid (5 mL, 65 mmol) at room temperature and allowed to stir for 3 h. The reaction mixture is evaporated under the reduced pressure. To the residue is added 1 N HCl (30 mL) and washed with ethyl acetate and the aqueous layer is basified with the pellet of NaOH (3 g, 75 mmol) and extracted with 20% isopropyl alcohol in CH$_2$Cl$_2$ (100 mL). The combined organic layer is dried over anhydrous Na$_2$SO$_4$, filtered and evaporated to give the title product (550 mg, 31%). This is used for the next step without further purification. $^1$H NMR (400 MHz, CD$_3$OD) δ 7.90 (s, 1H), 4.47 (t, J=6.0 Hz, 2H), 2.77 (t, J=4.8 Hz, 4H), 2.65 (t, J=6.0 Hz, 2H), 2.51 (s, 3H), 2.47 (m, 4H).

Step 3. 3-[[[4-[2-(2-methyl-5-nitro-imidazol-1-yl)ethyl]-1-piperazinyl]imino]methyl]rifamycin SV. To a stirred solution of 1-[2-(2-methyl-5-nitro-imidazol-1-yl)-ethyl]-piperazine (762 mg) in 1 N NaOH solution, is added acetone (2 mL) at 0° C., followed by hydroxylamine-O-sulfuric acid (431 mg). This is allowed to stir at 0° C. for 2 h and warmed up to room temperature. Acetic acid (2 mL) is added, followed by methanol, and 3-formylrifamycin (461 mg). The mixture was allowed to stir for 3 days. The mixture was partitioned between water and dichloromethane, and organic layer was separated, dried over sodium sulfate, and concentrated in vacuo. The residue was purified by preparative TLC plates (10% methanol in dichloromethane) to give orange solid (40 mg). ESI MS m/z 962 (M+H$^+$); $^1$H NMR (400 MHz, CDCl$_3$) δ 13.47 (s, 1H), 13.21 (s, 1H), 13.14 (s, 1H), 12.00 (s, 1H), 8.24 (s, 1H), 7.91 (s, 1H), 6.55 (dd, J=11.2 Hz and 15.2 Hz, 1H), 6.36 (d, J=11.2 Hz, 1H), 6.19 (d, J=12.4 Hz, 1H), 5.90 (dd, J=15.2 Hz and 4.8 Hz, 1H), 5.08 (dd, J=12.4 Hz and 6.8 Hz, 1H), 4.93 (d, J=10.8 Hz, 1H), 4.45-4.39 (m, 2H), 4.19 (t, J=5.2 Hz, 1H), 3.78-3.70 (m, 2H), 3.52 (s, 1H), 3.45 (d, J=6.8 Hz, 1H), 3.03 (s, 3H), 2.71-2.56 (m, 8H), 2.51 (s, 3H), 2.45 (t, J=6.4 Hz, 2H), 2.39-2.34 (m, 1H), 2.21 (s, 3H), 2.06 (s, 3H), 2.05 (s, 3H), 1.79 (s, 3H), 1.70-1.68 (m, 1H), 1.54-1.47 (m, 1H), 1.39-1.29 (m, 1H), 1.00 (d, J=6.4 Hz, 3H), 0.84 (d, J=6.8 Hz, 3H), 0.58 (d, J=6.4 Hz, 3H), −0.33 (d, J=6.8 Hz, 3H).

Example 4

3'-Hydroxy-5'-[4-[2-(2-methyl-5-nitro-imidazol-1-yl)ethyl]-1-piperazinyl]benzoxazinorifamycin

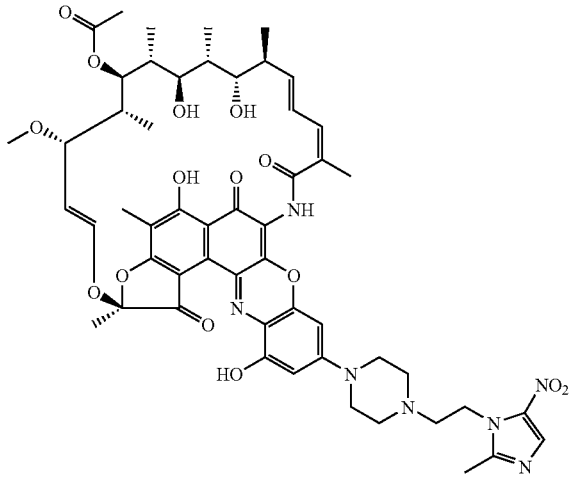

Step 1: 3'-Hydroxybenzoxazinorifamycin. This compound is prepared according to the procedure described in Helv. Chim. Acta., 1973, 56, p. 2369.

Step 2: 3'-Hydroxy-5'-[4-[2-(2-methyl-5-nitro-imidazol-1-yl)ethyl]-1-piperazinyl]benzoxazinorifamycin. To a stirred solution of 3'-hydroxybenzoxazinorifamycin (83 mg) in DMSO is added 1-[2-(2-methyl-5-nitro-imidazol-1-yl)-ethyl]-piperazine (50 mg) prepared as described above in example 3 and MnO$_2$ (82 mg). The mixture is allowed to stir at room temperature for 18 h. The mixture was partitioned between water and ethyl acetate. The organic layer is separated, dried over sodium sulfate, concentrated in vacuo. The residue is purified by preparative TLC plates (ethyl acetate then 10% methanol in dichloromethane) to give dark-blue solid (40 mg). ESI MS m/z 1038 (M+H$^+$); $^1$H NMR (400 MHz, CDCl$_3$) δ 9.98 (s, 1H), 7.92 (br s, 1H), 6.42 (s, 1H), 6.28 (s, 1H), 4.98 (dd, 1H), 4.44 (br s, 3H), 3.74-2.84 (complex pattern), 3.44 (br s, 2H), 3.04 (br s, 2H), 2.70 (br s, 2H), 2.61 (br s, 2H), 2.52 (s, 3H), 2.27 (s, 3H), 2.09 (s, 2H), 2.01 (s, 2H), 1.80-1.22 (complex pattern), 0.92 (d, 3H), 0.78 (m, 3H), 0.78 (d, 3H), 0.16 (d, 3H).

Example 5

4-Deoxy-3,4-[2-spiro-[1-(2-methyl-6-nitro-2,3-dihydro-imidazo[2,1-b]oxazol-2-ylmethyl)-piperidin-4-yl]]-(1H)-imidazo-(2,5-dihydro)rifamycin S

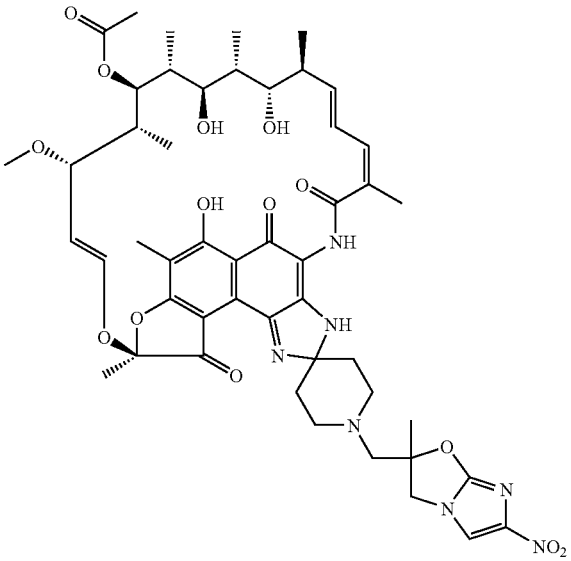

Step 1. 2-Bromo-1-(2-methyl-allyl)-4-nitro-1H-imidazole: A mixture of 2-bromo-4-nitro-1H-imidazole (10 g, 52 mmol), 3-chloro-2-methyl-propene (10.2 mL, 104 mmol) and K$_2$CO$_3$ (21.6 g, 156 mmol) in DMF (100 mL) was heated for 1d at 65° C. The resulting heterogeneous reaction mixture was diluted with ethyl acetate and washed with saturated brine. The combined organic layer was dried over anhydrous Na$_2$SO$_4$, filtered and evaporated to give the desired product (12.5 g, 98%). This product was used for the next step without further purification. $^1$H NMR (400 MHz, CDCl$_3$) δ 7.78 (s, 1H), 5.10 (d, J=0.8 Hz, 1H), 4.81 (d, J=0.8 Hz, 1H), 4.53 (s, 2H), 1.76 (s, 3H).

Step 2. 2-Bromo-1-(2-methyl-oxiranylmethyl)-4-nitro-1H-imidazole: To a solution of 2-bromo-1-(2-methyl-allyl)-4-nitro-1H-imidazole (5.08 g, 20.7 mmol) in CH$_2$Cl$_2$ was added mCPBA (5.5 g, 24.8 mmol) and heated for 3 days at 40° C. The additional mCPBA (2.8 g, 12 mmol) was added in order to complete the reaction and heated for another 3 days at 40° C. The reaction mixture was cooled to the room temperature, filtered, washed with CH$_2$Cl$_2$. Filtrate was transferred into the separatory funnel, washed with 0.5 N NaOH three times and followed by brine. The organic layer was dried over anhydrous Na$_2$SO$_4$, filtered and evaporated to give the desired product (4.63 g, 85%). This product was used for the next step without further purification. ESI MS m/z 262, 264 (M+H+); 1H NMR (400 MHz, CDCl3) δ 7.90 (s, 1H), 4.36 (d, J=14.8 Hz, 1H), 3.97 (d, J=14.8 Hz, 1H), 2.76 (d, J=4.0 Hz, 1H), 2.58 (d, J=4.0 Hz, 1H) 1.36 (s, 3H).

Step 3. 1-[3-(2-Bromo-4-nitro-imidazol-1-yl)-2-hydroxy-2-methyl-propyl]-piperidin-4-ol: A mixture of 2-bromo-1-(2-methyl-oxiranylmethyl)-4-nitro-1H-imidazole (1.57 g, 6.0 mmol) and hydroxypiperidine (0.607 g, 6 mmol) in isopropyl alcohol (30 mL) was heated for 3 h at 65° C. The solvent was removed under the reduced pressure and the resulting residue was purified by silica gel column chromatography (5% methanol in CH2Cl2) to give the inseparable mixture (1.27 g, 55%) of the desired alkylated product (1-[3-(2-bromo-4-nitro-imidazol-1-yl)-2-hydroxy-2-methyl-propyl]-piperidin-4-ol) and the cyclized product (1-(2-methyl-6-nitro-2,3-dihydro-imidazo[2,1-b]oxazol-2-ylmethyl)-piperidin-4-ol). This mixture was used for the next step without further separation.

Step 4. 1-(2-Methyl-6-nitro-2,3-dihydro-imidazo[2,1-b]oxazol-2-ylmethyl)-piperidin-4-ol: To a cold (0° C.) solution of the mixture (1.27 g) obtained from step 3 in anhydrous DMF (8 mL) was added NaH (274 mg, 6.85 mmol) and stirred for 1 h at 0° C. The reaction mixture was quenched with saturated NH4Cl and diluted with a small volume of water and extracted with 20% isopropyl alcohol in CH2Cl2 and the organic layer was dried over anhydrous Na2SO4, filtered and evaporated. The resulting residue (1.066 g) was used for the next step without further purification. ESI MS m/z 283 (M+H+); 1H NMR (400 MHz, CD3OD) δ 7.86 (s, 1H), 4.31 (d, J=10.4 Hz, 1H), 4.05 (d, J=10.4 Hz, 1H), 3.52-3.45 (m, 1H), 2.91-2.88 (m, 1H), 2.86-2.77 (m, 1H), 2.79 (d, J=14.8 Hz, 1H), 2.66 (d, J=14.8 Hz, 1H), 2.42 (td, J=10.4 Hz and 2.4 Hz, 1H), 2.31 (td, J=10.4 Hz and 2.4 Hz, 1H), 1.72-1.69 (m, 2H), 1.58 (s, 3H), 1.45-1.35 (m, 1H), 1.28-1.19 (m, 1H).

Step 5. 1-(2-Methyl-6-nitro-2,3-dihydro-imidazo[2,1-b]oxazol-2-ylmethyl)-piperidin-4-one: To a stirred solution of anhydrous DMSO (2.4 mL, 33.7 mmol) in CH2Cl2 (12 mL) at −78° C. was added slowly 2 M oxalyl chloride in CH2Cl2 (8.0 mL, 16 mmol) at −78° C. and allowed to stir for 20 min. A solution of 1-(2-methyl-6-nitro-2,3-dihydro-imidazo[2,1-b]oxazol-2-ylmethyl)-piperidin-4-ol (1.066 g, 3.78 mmol) in DMSO (3.3 mL) and CH2Cl2 (10 mL) was added to the reaction mixture and allowed to stir for 1 h at −78° C. Triethylamine (8.7 mL) was added and allowed to stir for 20 min at −78° C. and the temperature was allowed to rise to room temperature and stirred for 1 h at the room temperature. To the reaction mixture was added water and extracted with 20% isopropyl alcohol in CH2Cl2. The combined organic layer was dried over anhydrous Na2SO4, filtered and evaporated in vacuo. The resulting residue was purified by silica gel column chromatography (7% Methanol in CH2Cl2) to give the desired product (1.439 g, contains a small amount of DMSO). ESI MS m/z 281 (M+H+); 1H NMR (400 MHz, CD3OD) δ 7.87 (s, 1H), 4.43 (d, J=10.4 Hz, 1H), 4.13 (d, J=10.4 Hz, 1H), 3.01-2.89 (m, 4H), 2.99 (d, J=14.4 Hz, 1H), 2.87 (d, J=14.4 Hz, 1H), 2.37-2.30 (m, 2H), 2.26-2.20 (m, 2H), 1.64 (s, 3H).

Step 6. 4-Deoxy-3,4-[2-spiro-[1-(2-methyl-6-nitro-2,3-dihydro-imidazo[2,1-b]oxazol-2-ylmethyl)-piperidin-4-yl]]-(1H)-imidazo-(2,5-dihydro)rifamycin S: The solution of 1-(2-methyl-6-nitro-2,3-dihydro-imidazo[2,1-b]oxazol-2-ylmethyl)-piperidin-4-one (391 mg, 1.40 mmol) and NH4OAc (1.076 g, 14.0 mmol) in THF (12 mL) was heated briefly and stirred for 15 min at the room temperature. To this, Zinc (91 mg, 1.40 mmol) and 3-amino-4-deoxy-4-imino-rifamycin S (0.700 g, 0.99 mmol) were added and allowed to stir for 3 h. The mixture was diluted with ethyl acetate and washed with water and saturated brine. The organic layer was dried over anhydrous Na2SO4, filtered and evaporated. The residue is purified by preparative thin layer chromatography (5% MeOH in CH2Cl2) to give the title compound as an inseparable diastereomeric mixture (364 mg, 38%). ESI MS m/z 973 (M+H+); 1H NMR (400 MHz, CDCl3) δ 14.67 (s, ½H), 14.62 (s, ½H), 9.03 (s, ½H), 8.81 (s, ½H), 8.19 (s, 1H), 7.60 (s, ½H), 7.59 (s, ½H), 6.40-6.24 (m, 2H), 6.16 (dd, J=12.4 Hz and 6.0 Hz, 1H), 6.03-5.95 (m, 1H), 5.16-5.08 (m, 1H), 4.74-4.70 (m, 1H), 4.39 (dd, J=9.2 Hz and 7.2 Hz, 1H), 3.96 (dd, J=9.2 Hz and 1.2 Hz, 1H), 3.67-3.57 (m, 2H), 3.49-3.43 (m, 2H), 3.34-3.28 (m, 2H), 3.16-2.98 (m, 3H), 3.08 (s, 3/2H), 3.075 (s, 3/2H), 2.84-2.69 (m, 2H), 2.39-2.28 (m, 1H), 2.33 (s, 3H), 2.04 (s, 3/2H), 2.02 (s, 3/2H), 1.81-1.57 (m, 6H), 1.75 (s, 3/2H), 1.74 (s, 3/2H), 1.69 (s, 3/2H), 1.66 (s, 3/2H), 1.63 (s, 3H), 1.40 (m, 1H), 1.03 (d, J=6.8 Hz, 3/2H), 1.02 (d, J=6.8 Hz, 3/2H), 0.83 (d, J=6.4 Hz, 3/2H), 0.82 (d, J=6.4 Hz, 3/2H), 0.60 (d, J=6.8 Hz, 3H), −0.09 (d, J=7.2 Hz, 3/2H), −0.10 (d, J=6.8 Hz, 3/2H).

Example 6

3-{4-[4-(6-Nitro-2,3-dihydro-imidazo[2,1-b]oxazol-2-ylmethoxy)-benzyl]-piperazin-1-yl}rifamycin S

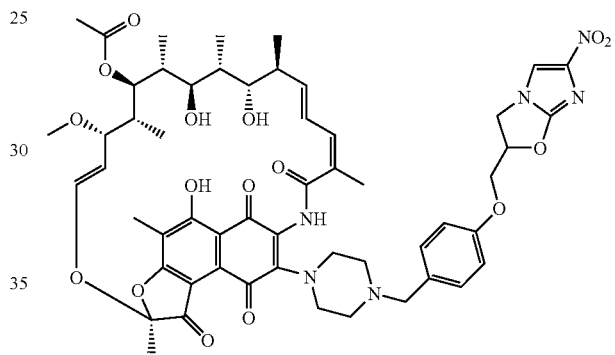

Step 1. 4-[3-(2-Bromo-4-nitro-imidazol-1-yl)-2-hydroxy-propoxy]-benzaldehyde. A mixture of 2-bromo-4-nitro-1H-imidazole (2.2 g, 11.2 mmol), 4-Oxiranylmethoxy-benzaldehyde (2.0 g, 11.2 mmol), and sodium acetate (1.8 g, 22.4 mmol) in ethanol was stirred overnight at 40° C. The mixture was cooled to room temperature and solvent was evaporated. The resulting residue was purified by silica gel column chromatography (1:1 ethyl acetate and hexanes) to give the title compound as oil (1.8 g, 44%). ESI MS m/z 370 (M+H+); 1H NMR (400 MHz, CDCl3) δ 9.84 (s, 1H), 8.47 (s, 1H), 7.83 (d, J=22.0 Hz, 2H), 7.09 (d, J=22.0 Hz, 2H), 5.71 (d, J=13.0 Hz, 1H), 4.29-4.07 (m, 4H), 2.48 (d, J=4.0 Hz, 1H).

Step 2. 4-(6-Nitro-2,3-dihydro-imidazo[2,1-b]oxazol-2-ylmethoxy)-benzaldehyde. To a stirred solution of 4-[3-(2-bromo-4-nitro-imidazol-1-yl)-2-hydroxy-propoxy]-benzaldehyde (0.5 g, 1.4 mmol) in anhydrous DMF (5 mL) was added NaH (60% dispersion in oil, 108.0 mg, 2.7 mmol) and stirred for 1 h at 0° C., then stirred the reaction mixture for 2 hrs at 50° C. The reaction mixture was diluted with ethyl acetate and washed with water and saturated brine. The organic layer was dried over anhydrous Na2SO4, filtered and evaporated. The residue was recrystallized with 9:1 IPA and EtOAc to give the title compound as solid (160 mg, 41%). ESI MS m/z 290 (M+H+); 1H NMR (400 MHz, CDCl3) δ 9.84 (s, 1H), 7.79 (d, J=17.0 Hz, 2H), 7.54 (s, 1H), 6.94 (d, J=22.0 Hz, 2H), 5.62 (m, 1H), 4.47-4.31 (m, 4H).

Step 3. 4-[4-(6-Nitro-2,3-dihydro-imidazo[2,1-b]oxazol-2-ylmethoxy)-benzyl]-piperazine-1-carboxylic acid tert-butyl ester. To a stirred solution of 4-(6-nitro-2,3-dihydro-imidazo[2,1-b]oxazol-2-ylmethoxy)-benzaldehyde (148 mg, 0.5 mmol) in THF (3 mL) was added N-boc-piperazine (143 mg, 0.8 mmol) and a drop of acetic acid. The reaction mixture was allowed to stir at room temperature for 1 h, then NaBH(OAc)$_3$ (217.0 mg, 1.0 mmol) in THF (2 mL) was added and stirred overnight. To the reaction mixture was added water, cooled to 0° C. and the pH was adjusted to greater than 12 with NaOH pellet. The reaction mixture was extracted with 20% isopropyl alcohol in $CH_2Cl_2$. The combined organic layer was dried over anhydrous $Na_2SO_4$, filtered and evaporated. The residue was purified by preparative TLC (5% MeOH in $CH_2Cl_2$) to give the title product as solid (36 mg, 16%). $^1$H NMR (400 MHz, CDCl$_3$) δ 7.59 (s, 1H), 7.22 (d, J=6.0 Hz, 2H), 6.81 (d, J=6.0 Hz, 2H), 5.61 (m, 1H), 4.46-4.28 (m, 4H), 3.40 (m, 6H), 2.34 (bs, 4H), 1.44 (s, 9H).

Step 4. 3-{4-[4-(6-Nitro-2,3-dihydro-imidazo[2,1-b]oxazol-2-ylmethoxy)-benzyl]-piperazin-1-yl}rifamycin S. To a stirred solution of 4-[4-(6-Nitro-2,3-dihydro-imidazo[2,1-b]oxazol-2-ylmethoxy)-benzyl]-piperazine-1-carboxylic acid tert-butyl ester (36 mg, 0.08 mmol) was added trifluoroacetic acid (0.5 mL) at room temperature and allowed to stir for 30 min. The trifluoroacetic acid was evaporated under the reduced pressure, residue was dissolved in THF, added 3-bromorifamycin (77 mg, 0.1 mmol) and triethylamine (35 mg, 0.35 mmol), and the reaction mixture was allowed to stir for 30 min at room temperature. The reaction mixture was diluted with ethyl acetate and washed with water and saturated brine. The combined organic layer was dried over anhydrous $Na_2SO_4$, filtered and evaporated. The residue was purified by preparative TLC (5% MeOH in $CH_2Cl_2$) to give the title product as red solid (14.6 mg, 14%). ESI MS m/z 1053 (M+H$^+$); $^1$H NMR (400 MHz, CDCl$_3$) δ 12.58 (s, 1H), 7.42 (s, 1H), 7.29 (s, 1H), 7.09 (s, 1H), 7.06 (d, J=22.0 Hz, 2H), 6.65 (d, J=22.0 Hz, 2H), 6.16 (d, J=27.0 Hz, 1H), 5.93 (m, 1H), 5.89 (dd, J=2.0, 30.0 Hz, 1H), 5.46 (m, 1H), 4.95-4.90 (m, 2H), 4.32-4.19 (m, 3H), 4.12 (dd, J=8.0, 26.0 Hz, 1H), 3.77 (d, J=30.0 Hz, 1H), 3.35-3.15 (m, 10H), 2.93 (s, 3H), 2.88 (m, 1H). 2.49 (bs, 2H), 2.30 (bs, 2H), 2.19 (m, 1H), 2.09 (s, 3H), 1.92 (s, 3H), 1.91 (s, 3H), 1.67-1.61 (m, 3H), 1.51 (s, 1H), 1.08 (s, 1H), 0.86 (d, J=17 Hz, 3H), 0.71 (d, J=18.0 Hz, 3H), 0.52 (d, J=17.0 Hz, 3H), 0 (d, J=16.0 Hz, 3H).

Example 7

4-Deoxy-3,4-[2-[4-(6-nitro-2,3-dihydro-imidazo[2,1-b]oxazol-2-ylmethoxy)-phenyl]]-(1H)-imidazo-rifamycin SV

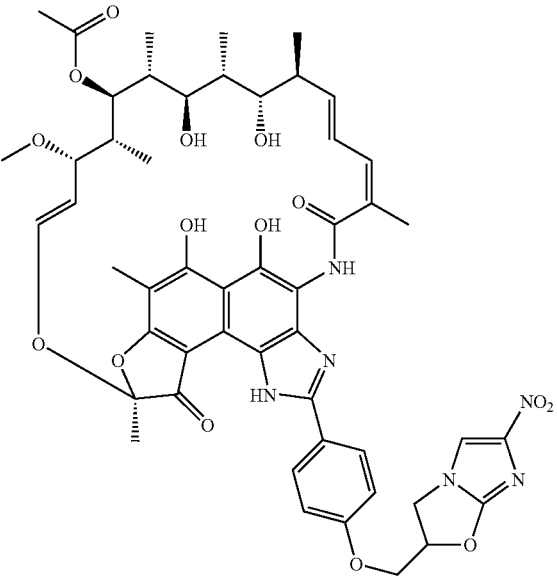

The title compound was prepared by following the same procedure as described for the preparation of Example 1, except 4-(6-nitro-2,3-dihydro-imidazo[2,1-b]oxazol-2-ylmethoxy)-benzaldehyde was used in place of 1-[2-(2-methyl-5-nitro-imidazol-1-yl)-ethyl]-piperidin-4-one. The title product was isolated as solid. ESI MS m/z 981 (M+H$^+$); $^1$H NMR (400 MHz, CDCl$_3$) δ 13.20 (bs, 1H), 12.90 (bs, 1H), 9.20 (bs, 2H), 8.20 (bs, 2H), 7.96 (d, J=23 Hz, 2H), 7.56 (d, J=23 Hz, 1H), 7.20 (s, 2H), 7.02 (s, 1H), 6.76 (s, 1H), 6.48 (bs, 2H), 6.01 (s, 1H), 5.30 (s, 1H), 4.98-4.63 (m, 5H), 3.90 (s, 3H), 3.58 (bs, 1H), 3.27 (d, J=24 Hz, 3H), 3.14 (bs, 1H), 2.68-2.21 (m, 12H), 1.88 (bs, 1H), 1.54 (d, J=23 Hz, 1H), 1.35-1.17 (m, 6H), 0.28 (bs, 3H), −0.35 (bs, 3H).

Example 8

3-{4-[4-(2-Methyl-6-nitro-2,3-dihydro-imidazo[2,1-b]oxazol-2-ylmethoxy)-benzoyl]-piperazin-1-yl}rifamycin S

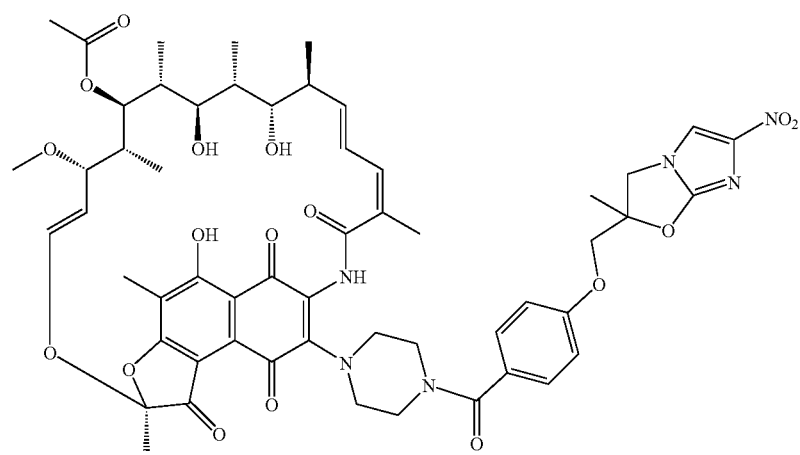

The title compound was prepared by following the same procedure as described for the preparation of Example 6, except [4-(2-methyl-6-nitro-2,3-dihydro-imidazo[2,1-b]oxazol-2-ylmethoxy)-phenyl]-piperazin-1-yl-methanone was used in place of 6-nitro-2-(4-piperazin-1-ylmethyl-phenoxymethyl)-2,3-dihydro-imidazo[2,1-b]oxazole. The title product was isolated as solid. 3-{4-[4-(6-nitro-2,3-dihydro-imidazo[2,1-b]oxazol-2-ylmethoxy)-benzyl]-piperazin-1-yl}rifamycin S. ESI MS m/z 1081 (M+H⁺); ¹H NMR (400 MHz, CDCl₃) δ 8.02 (s, 1H), 751 (s, 1H), 7.33 (d, J=21 Hz, 2H), 7.24 (d, J=3 Hz, 1H), 7.20 (m, 2H), 6.80 (m, 2H), 6.31 (d, J=27.0 Hz, 1H), 6.15 (dd, J=17.32 Hz, 1H), 5.98 (d, J=32.0 Hz, 1H), 5.47 (bs, 1H), 5.00-5.05 (m, 2H), 4.44 (d, J=27 Hz, 1H), 4.28-4.20 (m, 2H), 4.06-3.94 (m, 3H), 3.87-3.79 (m, 1H), 3.66 (m, 1H), 3.54 (bs, 1H). 3.41 (bs, 2H), 3.03 (s, 3H), 2.20 (s, 3H), 2.01 (s, 3H), 1.84 (d, J=16 Hz, 6H), 1.74 (s, 3H), 1.67 (s, 1H), 1.54 (bs, 3H), 1.18-1.14 (m, 4H), 0.96 (d, J=18.0 Hz, 3H), 0.82 (d, J=17.0 Hz, 3H), 0.63 (d, J=17.0 Hz, 3H), 0.08 (d, J=17.0 Hz, 3H).

Example 9

4-Deoxy-3,4-[2-spiro-[1-[4-[6S-(2-nitro-6,7-dihydro-5H-imidazo[2,1-b][1,3]oxazin-6-yloxymethyl)]-benzyl]-piperidin-4-yl]]-(1H)-imidazo-(2,5-dihydro) rifamycin S

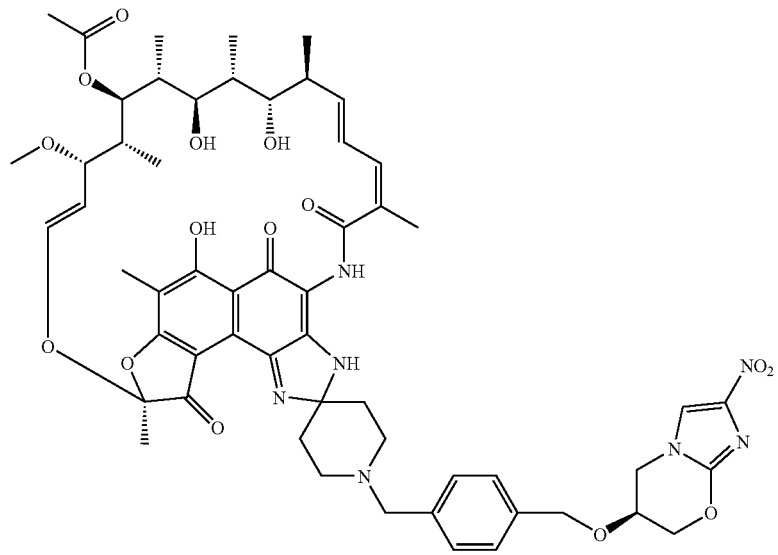

Step 1. 6-(4-Chloromethyl-benzyloxy)-2-nitro-6,7-dihydro-5H-imidazo[2,1-b][1,3]oxazine. To a stirred solution of 2-nitro-6,7-dihydro-5H-imidazo[2,1-b][1,3]oxazin-6-ol (0.1 g, 0.54 mmol) in anhydrous DMF (1 mL) was added NaH (60% dispersion in oil, 26.0 mg, 0.65 mmol) and stirred at 0° C. for 30 min. 1,4-Bis-chloromethyl-benzene (472 mg, 2.7 mmol) in anhydrous DMF (0.5 mL) was added to the reaction mixture and stirred at 0° C. for 30 min, and the reaction mixture was stirred at room temperature for additional 3 hr. The reaction mixture was diluted with ethyl acetate and washed with water and saturated brine. The organic layer was dried over anhydrous Na₂SO₄, filtered and evaporated. The residue was washed with hexanes and gave the title compound as solid (65 mg, 37%). ESI MS m/z 324 (M+H⁺); ¹H NMR (400 MHz, CDCl₃) δ 7.39-7.24 (m, 5H), 4.72 (d, J=30.0 Hz, 1H), 4.59 (m, 2H), 4.32 (d, J=30.0 Hz, 1H), 4.16 (m, 1H), 1.60 (s, 4H).

Step 2. 1-[4-(2-Nitro-6,7-dihydro-5H-imidazo[2,1-b][1,3]oxazin-6-yloxymethyl)-benzyl]-piperidin-4-one. A suspension of 6-(4-chloromethyl-benzyloxy)-2-nitro-6,7-dihydro-5H-imidazo[2,1-b][1,3]oxazine (1.0 g, 3.0 mmol), 4-piperidone hydrochloride monohydrate (2.4 g, 15 mmol), and K₂CO₃ (2.1 g, 15 mmol) in IPA was stirred at 50° C. overnight. The reaction was cooled to room temperature and diluted with DCM, then washed with water and saturated brine. The organic layer was dried over anhydrous Na₂SO₄, filtered and evaporated. The residue was purified by silica gel column chromatography (5% MeOH in CH₂Cl₂) to give the title product as solid (1.1 g, 92%). ESI MS m/z 387 (M+H⁺); ¹H NMR (400 MHz, CDCl₃) δ 7.39-7.24 (m, 5H), 4.74 (d, J=30.0 Hz, 1H), 4.61 (m, 1H), 4.34 (d, J=30.0 Hz, 1H), 4.16 (m, 2H), 3.61 (s, 2H), 2.74 (t, J=12 Hz, 4H), 2.45 (t, J=13 Hz, 4H), 1.23 (s, 2H).

Step 3. 2-Nitro-6-[4-(1,4,8-triaza-spiro[4.5]dec-8-ylmethyl)-benzyloxy]-6,7-dihydro-5H-imidazo[2,1-b][1,3]oxazine rifamycin S. The title compound is prepared by following the same procedure as described for the preparation of Example 1 except 1-[4-(2-Nitro-6,7-dihydro-5H-imidazo[2,1-b][1,3]oxazin-6-yloxymethyl)-benzyl]-piperidin-4-one was used in place of 1-[2-(2-methyl-5-nitro-imidazol-1-yl)-ethyl]-piperidin-4-one. The title product was isolated as solid. ESI MS m/z 1078 (M+H⁺); ¹H NMR (400 MHz, CDCl₃) δ 9.08 (bs, 1H), 8.34 (s, 1H), 7.51 (m, 2H), 7.38 (m, 2H), 6.46 (m, 1H), 6.36 (d, J=25 Hz, 1H), 6.25 (d, J=30.5 Hz, 1H), 6.12 (dd, J=13.36 Hz, 1H), 5.23 (m, 1H), 4.86 (t, J=26 Hz, 2H), 4.73 (t, J=30 Hz, 2H), 4.45 (d, J=30 Hz, 1H), 4.26 (bs, 4H), 3.9 (bs, 2H), 3.77 (d, J=23 Hz, 2H), 3.44 (d, J=16 Hz, 2H), 3.18 (m, 10H), 2.43 (s, 4H). 2.27 (m, 1H), 2.12 (m, 8H), 1.86 (s, 4H), 1.54 (m, 1H), 1.36 (m, 1H), 1.12 (d, J=12.0 Hz, 3H), 0.93 (d, J=12.0 Hz, 3H), 0.67 (d, J=12.0 Hz, 3H), 0.06 (d, J=13.0 Hz, 3H).

Example 10

3-{4-[4-(6S-(2-Nitro-6,7-dihydro-5H-imidazo[2,1-b][1,3]oxazin-6-yloxymethyl)-benzyl]-piperazin-1-yl}rifamycin S

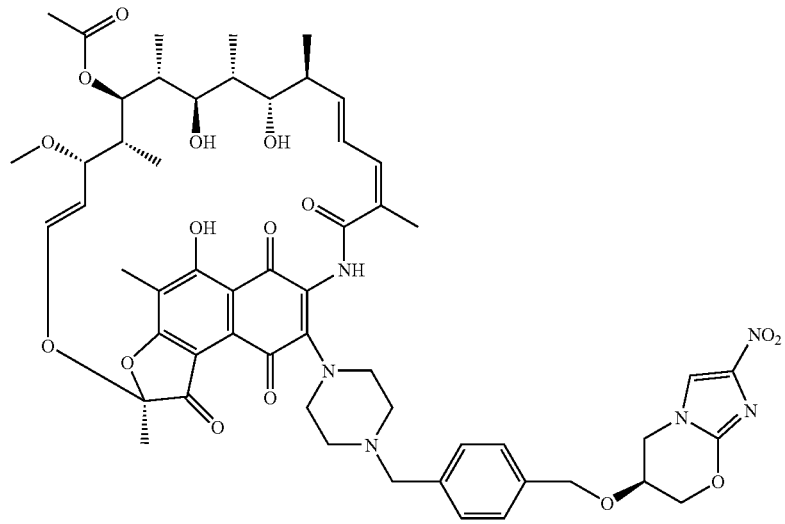

Step 1. 4-[4-(2-Nitro-6,7-dihydro-5H-imidazo[2,1-b][1,3]oxazin-6-yloxymethyl)-benzyl]-piperazine-1-carboxylic acid tert-butyl ester. A suspension of 6-(4-chloromethyl-benzyloxy)-2-nitro-6,7-dihydro-5H-imidazo[2,1-b][1,3]oxazine (0.2 g, 0.62 mmol), piperazine-1-carboxylic acid tert-butyl ester (0.17 g, 0.93 mmol), and $K_2CO_3$ (0.13 g, 0.93 mmol) in IPA was stirred at 50° C. overnight. The reaction mixture was cooled to room temperature and diluted with DCM, then washed with water and saturated brine. The organic layer is dried over anhydrous $Na_2SO_4$, filtered and evaporated. The residue was purified by silica gel column chromatography (5% MeOH in $CH_2Cl_2$) to give the title product as solid. ESI MS m/z 473 (M+H$^+$); $^1$H NMR (400 MHz, CDCl$_3$) δ 7.38 (s, 1H), 7.30 (d, J=20.0 Hz, 2H), 7.25 (d, J=20.0 Hz, 2H), 4.70 (d, J=31 Hz, 1H), 4.61 (m, 2H), 4.34 (d, J=31.0 Hz, 1H), 4.15 (m, 3H), 3.45 (s, 2H), 3.40 (t, J=11.0 Hz, 4H), 2.45 (t, J=12 Hz, 4H), 1.44 (s, 9H).

Step 2. 3-[4-(2-Nitro-6,7-dihydro-5H-imidazo[2,1-b][1,3]oxazin-6-yloxymethyl)-benzyl]-piperazine rifamycin S. The title compound is prepared by following the same procedure as described for the preparation of Example 6 except 4-[4-(2-nitro-6,7-dihydro-5H-imidazo[2,1-b][1,3]oxazin-6-yloxymethyl)-benzyl]-piperazine was used in place of 6-nitro-2-(4-piperazin-1-ylmethyl-phenoxymethyl)-2,3-dihydro-imidazo[2,1-b]oxazole. The title product was isolated as solid. ESI MS m/z 1068 (M+H$^+$); $^1$H NMR (400 MHz, CDCl$_3$) δ 13.14 (s, 1H), 7.31 (s, 1H), 7.22 (s, 1H), 7.10 (m, 5H), 6.17 (d, J=26.0 Hz, 1H), 5.98 (d, J=26.0 Hz, 1H), 5.89 (d, J=30.0 Hz, 1H), 4.92 (m, 1H), 4.55 (d, J=30.0 Hz, 1H), 4.44 (m, 2H), 4.17 (d, J=30.0 Hz, 1H), 3.97 (m, 3H), 3.77 (m, 2H), 3.37 (m, 2H), 3.18 (bs, 1H), 2.91-2.88 (m, 2H), 2.51 (bs, 1H), 2.32 (bs, 1H), 2.17 (bs, 1H), 2.09 (s, 1H), 1.91 (d, J=14 Hz, 6H), 1.64 (m, 1H), 1.56 (s, 3H), 1.46 (bs, 8H), 1.09 (bs, 3H), 0.86 (s, 3H), 0.73-0.66 (m, 6H), 0.52 (d, J=17 Hz, 3H), 0 (bs, 3H).

Example 11

3-{4-[4-(2-Methyl-6-nitro-2,3-dihydro-imidazo[2,1-b]oxazol-2-ylmethoxy)-benzyl]-piperazin-1-yl}rifamycin S

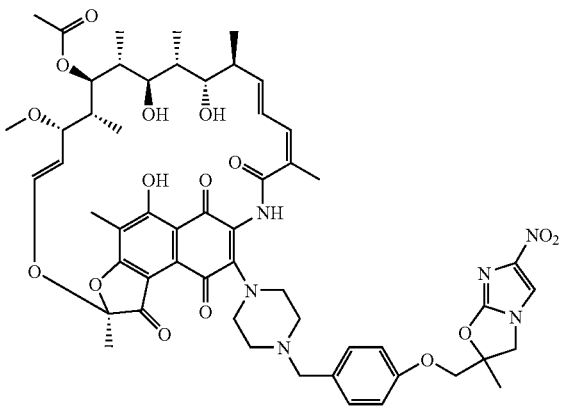

Step 1. 4-[4-(2-Methyl-6-nitro-2,3-dihydro-imidazo[2,1-b]oxazol-2-ylmethoxy)-benzyl]-piperazine-1-carboxylic acid tert-butyl ester. To a stirred solution of 4-(2-methyl-6-nitro-2,3-dihydro-imidazo[2,1-b]oxazol-2-ylmethoxy)-benzaldehyde (91 mg, 0.30 mmol) in MeOH (3 mL) was added N-boc-piperazine (84 mg, 0.45 mmol) and a drop of acetic acid. The reaction mixture was allowed to stir for 1 h at room temperature, then added NaBH$_3$CN (38.0 mg, 0.60 mmol) in MeOH (2 mL). The resulting reaction mixture was stirred for 2 hrs at room temperature. The solvent was removed, then water was added and cooled to 0° C., and the pH was adjusted to 12 with NaOH pellet. The mixture was extracted with 20% isopropyl alcohol in CH$_2$Cl$_2$. The combined organic layer was dried over anhydrous Na$_2$SO$_4$, filtered and evaporated. The residue is purified by preparative TLC (5% MeOH in CH$_2$Cl$_2$) to give the title product as solid (44 mg, 31%). $^1$H NMR (400 MHz, CDCl$_3$) δ 7.56 (s, 1H), 7.24 (d, J=20.0 Hz, 2H), 6.80 (d, J=20.0 Hz, 2H), 4.49 (d, J=26 Hz, 1H), 4.21 (d, J=26 Hz, 1H), 4.06 (t, J=24 Hz, 2H), 3.43 (m, 6H), 2.36 (s, 4H), 1.78 (s, 3H), 1.46 (s, (H).

Step 2. 3-{4-[4-(2-Methyl-6-nitro-2,3-dihydro-imidazo[2,1-b]oxazol-2-ylmethoxy)-benzyl]-piperazine}rifamycin S. The title compound is prepared by following the same procedure as described for the preparation of Example 6, except starting from 4-[4-(2-methyl-6-nitro-2,3-dihydro-imidazo[2,1-b]oxazol-2-ylmethoxy)-benzyl]-piperazine-1-carboxylic acid tert-butyl ester in place of 4-[4-(6-nitro-2,3-dihydro-imidazo[2,1-b]oxazol-2-ylmethoxy)-benzyl]-piperazine-1-carboxylic acid tert-butyl ester. The product was isolated as solid. ESI MS m/z 1068 (M+H$^+$); $^1$H NMR (400 MHz, CDCl$_3$) δ 12.58 (s, 1H), 7.40 (s, 1H), 7.30 (s, 1H), 7.09 (s, 1H), 7.09 (d, J=3.0 Hz, 1H), 7.05 (d, J=20.0 Hz, 2H), 6.63 (d, J=20.0 Hz, 2H), 6.16 (d, J=28.0 Hz, 2H), 5.98 (m, 1H), 5.90 (d, J=30.0 Hz, 1H), 5.46 (m, 1H), 4.94-4.90 (dd, J=27.0, 30.0 Hz, 1H), 4.34 (d, J=25.0 Hz, 1H), 4.06 (d, J=26.0 Hz, 1H), 3.77 (t, J=28.0 Hz, 2H), 3.78-3.75 (m, 2H), 3.36-3.18 (m, 8H), 2.92-2.85 (m, 4H), 2.48 (bs, 2H), 2.30 (bs, 2H), 2.17 (m, 1H), 2.09 (s, 3H), 1.92 (m, 6H), 1.65 (m, 5H), 1.56 (m, 8H), 0.86 (d, J=17 Hz, 3H), 0.71 (d, J=18.0 Hz, 3H), 0.52 (d, J=17.0 Hz, 3H), 0.07 (d, J=16.0 Hz, 3H).

Example 12

3'-Hydroxy-5'-[4-[4-(6S-2-nitro-6,7-dihydro-5H-imidazo[2,1-b][1,3]oxazin-6-yloxymethyl)-benzyl]-1-piperazinyl]benzoxazinorifamycin

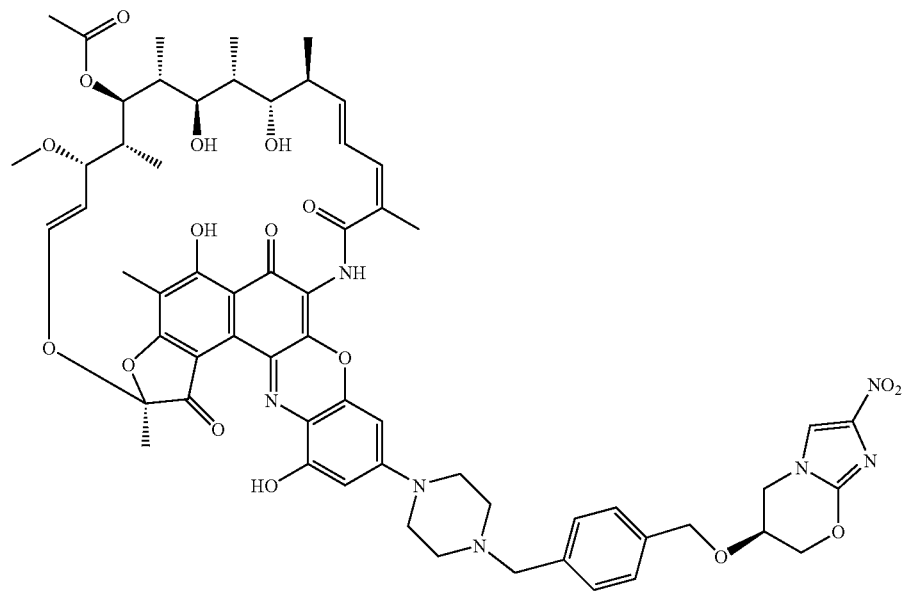

The title compound is prepared by following the same procedure as described for the preparation of Example 4 except 1-[4-(2-methyl-6-nitro-2,3-dihydro-imidazo[2,1-b]oxazol-2-ylmethoxy)-benzyl]-piperazine was used in place of 1-[2-(2-methyl-5-nitro-imidazol-1-yl)-ethyl]-piperazine. The product was isolated as blue solid. ESI MS m/z 1172 (M+H$^+$); $^1$H NMR (400 MHz, CDCl$_3$) δ 10.30 (bs, 1H), 8.12 (bs, 1H), 7.75-7.63 (m, 12H), 7.17 (d, J=21 Hz, 2H), 6.76 (s, 2H), 6.64 (s, 2H), 6.42 (bs, 4H), 5.34 (dd, J=19.0, 30 Hz, 2H), 5.10 (m, 2H), 4.99 (m, 4H), 4.71 (dd, J=11.0, 30.0 Hz, 1H), 4.56 (m, 6H), 3.92 (m, 12H), 3.41 (bs, 7H), 2.95 (bs, 6H), 2.79 (m, 3H), 2.62 (s, 4H), 2.45-2.38 (m, 16H), 1.63 (m, 3H), 1.33-1.21 (m, 10H), 1.17 (bs, 3H), 0.52 (bs, 3H), 0.00 (bs, 3H).

Example 13

4-Deoxy-3,4-[2-spiro-[1-[3-(6S-2-nitro-6,7-dihydro-5H-imidazo[2,1-b][1,3]oxazin-6-yloxymethyl)]-benzyl]-piperidin-4-yl]]-(1H)-imidazo-(2,5-dihydro) rifamycin S

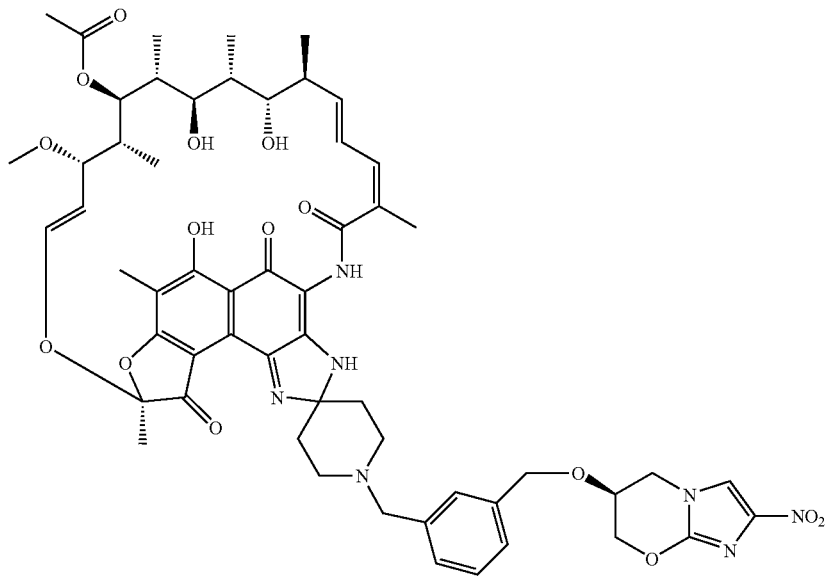

Step 1. 1-[3-(2-Nitro-6,7-dihydro-5H-imidazo[2,1-b][1,3]oxazin-6-yloxymethyl)-benzyl]-piperidin-4-one. The title compound is prepared by following the same procedure as described in the preparation of Example 9, except 1,3-bis-chloromethyl-benzene was used in place of 1,4-bis-chloromethyl-benzene. ESI MS m/z 387 (M+H$^+$); $^1$H NMR (400 MHz, CDCl$_3$) δ 7.40-7.20 (m, 5H), 4.70 (d, J=30.0 Hz, 1H), 4.61 (m, 2H), 4.34 (d, J=30.0 Hz, 1H), 4.16 (m, 3H), 3.58 (s, 2H), 2.72 (t, J=14 Hz, 4H), 2.45 (t, J=14 Hz, 4H).

Step 2. 2-Nitro-6-[3-(1,4,8-triaza-spiro[4.5]dec-8-ylmethyl)-benzyloxy]-6,7-dihydro-5H-imidazo[2,1-b][1,3]oxazine. The title compound is prepared by following the same procedure as described in the preparation of Example 9, except 1-[3-(2-nitro-6,7-dihydro-5H-imidazo[2,1-b][1,3]oxazin-6-yloxymethyl)-benzyl]-piperidin-4-one was used in place of 1-[4-(2-Nitro-6,7-dihydro-5H-imidazo[2,1-b][1,3]oxazin-6-yloxymethyl)-benzyl]-piperidin-4-one. The product was obtained as a red solid. ESI MS m/z 1078 (M+H$^+$); $^1$H NMR (400 MHz, CDCl$_3$) δ 9.15 (bs, 1H), 8.38 (s, 1H), 7.58 (s, 2H), 7.52 (m, 2H), 7.41 (m, 1H), 6.53 (dd, J=28.39 Hz, 1H), 6.41 (d, J=31 Hz, 1H), 6.16 (dd, J=16.39 Hz, 1H), 5.23 (dd, J=19.33 Hz, 1H), 4.92 (m, 2H), 4.79 (d, J=30 Hz, 2H), 4.51 (d, J=30 Hz, 2H), 4.36-4.24 (m, 4H), 3.97 (bs, 2H), 3.80 (d, J=25 Hz, 2H), 3.47 (dd, J=5.17 Hz, 2H), 3.28-3.05 (m, 6H), 2.48 (s, 4H), 2.32 (s, 1H), 2.19 (m, 9H), 1.92 (s, 6H), 1.57 (m, 1H), 1.39 (m, 1H), 1.86 (d, J=18.0 Hz, 3H), 0.97 (d, J=12.0 Hz, 3H), 0.73 (d, J=17.0 Hz, 3H), 0.06 (d, J=17.0 Hz, 3H).

Example 14

3-{4-[3-(6S-(2-Nitro-6,7-dihydro-5H-imidazo[2,1-b][1,3]oxazin-6-yloxymethyl)]-benzyl]-piperazin-1-yl}rifamycin S

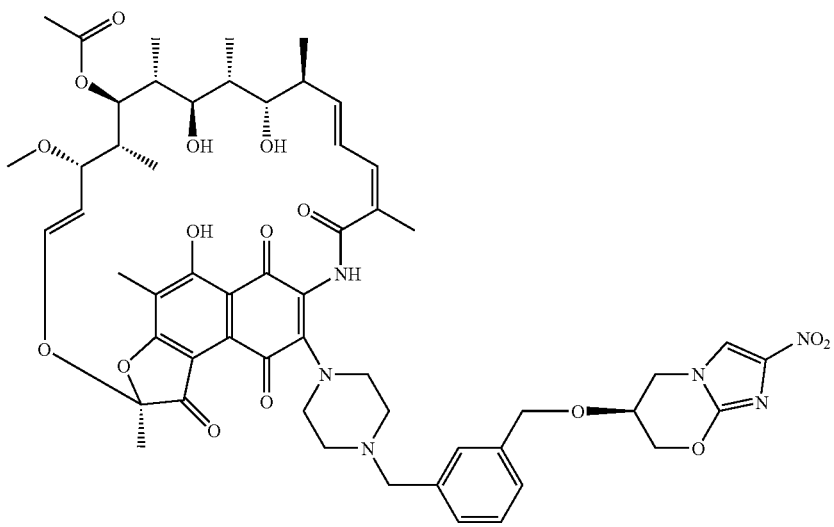

Step 1. 4-[4-(2-Nitro-6,7-dihydro-5H-imidazo[2,1-b][1,3]oxazin-6-yloxymethyl)-benzyl]-piperazine-1-carboxylic acid tert-butyl ester. The title compound is prepared by following the same procedure as described in the preparation of Example 10, except 1,3-bis-chloromethyl-benzene was used in place of 1,4-bis-chloromethyl-benzene. ESI MS m/z 473 (M+H$^+$); $^1$H NMR (400 MHz, CDCl$_3$) δ 7.38 (s, 1H), 7.32-7.19 (m, 4H), 4.71 (d, J=30 Hz, 1H), 4.60 (d, J=21 Hz, 2H), 4.33 (d, J=30.0 Hz, 1H), 4.15 (m, 3H), 3.45 (s, 2H), 3.41 (s, 4H), 2.37 (s, 4H), 1.44 (s, 9H).

Step 2. 3-{4-[3-(2-nitro-6,7-dihydro-5H-imidazo[2,1-b][1,3]oxazin-6-yloxymethyl)-benzyl]-piperazin-1-yl}rifamycin S. The title compound is prepared by following the same procedure as described for the preparation of Example 6, except starting from 4-[3-(2-nitro-6,7-dihydro-5H-imidazo[2,1-b][1,3]oxazin-6-yloxymethyl)-benzyl]-piperazine-1-carboxylic acid tert-butyl ester in place of 4-[4-(6-nitro-2,3-dihydro-imidazo[2,1-b]oxazol-2-ylmethoxy)-benzyl]-piperazine-1-carboxylic acid tert-butyl ester. The product was isolated as solid. ESI MS m/z 1068 (M+H$^+$); $^1$H NMR (400 MHz, CDCl$_3$) δ 12.90 (s, 1H), 12.19 (bs, 1H), 7.57 (s, 1H), 7.39-7.32 (m, 3H), 7.25-7.19 (m, 2H), 7.05 (m, 1H), 6.29 (d, J=27.0 Hz, 1H), 6.10 (m, 1H), 5.98 (d, J=31.0 Hz, 1H), 5.02 (m, 2H), 4.58 (m, 3H), 4.26 (d, J=30.0 Hz, 1H), 4.15-4.03 (m, 2H), 4.5 (d, J=28.0 Hz, 1H), 3.82 (d, J=23.0 Hz, 1H), 3.38 (bs, 5H), 3.10-2.96 (m, 10H), 2.26-2.21 (m, 4H), 2.01 (bs, 6H), 1.74-1.62 (m, 6H), 1.31-1.12 (m, 12H), 1.09 (d, J=10.0 Hz, 3H), 0.81 (m, 6H), 0.63 (d, J=10 Hz, 3H), 0.92 (d, J=12.0 Hz, 1H).

Example 15

3'-Hydroxy-5'-[4-[3-(6S-2-nitro-6,7-dihydro-5H-imidazo[2,1-b][1,3]oxazin-6-yloxymethyl)-benzyl]-1-piperazinyl]benzoxazinorifamycin

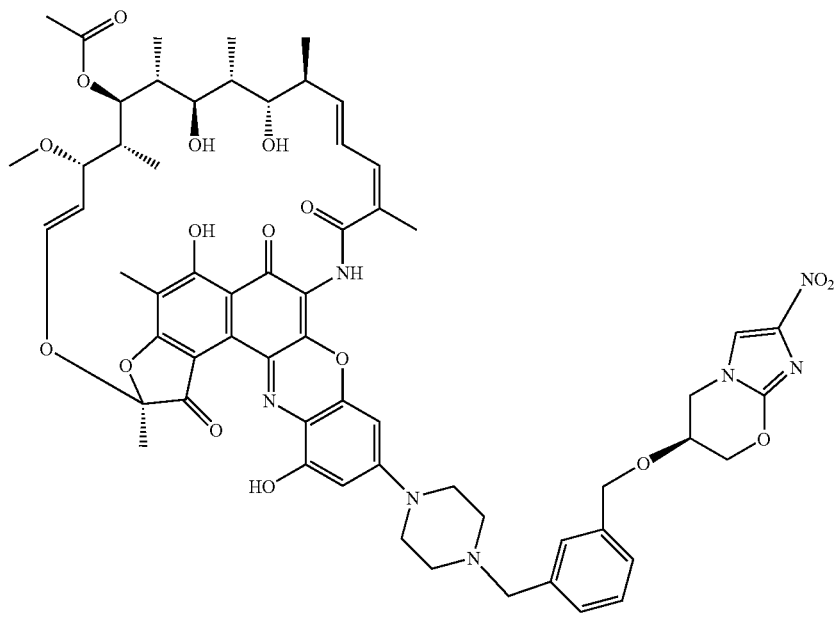

The title compound is prepared by following the same procedure as described for the preparation of Example 4, 3'-hydroxy-5'-[4-[2-(2-methyl-5-nitro-imidazol-1-yl)ethyl]-1-piperazinyl]benzoxazinorifamycin, except 1-[3-(2-methyl-6-nitro-2,3-dihydro-imidazo[2,1-b]oxazol-2-ylmethoxy)-benzyl]-piperazine was used in place of 1-[2-(2-methyl-5-nitro-imidazol-1-yl)-ethyl]-piperazine. The product was isolated as blue solid. ESI MS m/z 1172 (M+H$^+$); $^1$H NMR (400 MHz, CDCl$_3$) δ 11.39 (bs, 1H), 10.29 (bs, 1H), 9.67 (bs, 1H), 8.48 (bs, 1H), 7.82-7.63 (m, 6H), 7.3 (bs, 1H), 7.09 (bs, 1H), 6.75-5.98 (m, 4H), 5.58 (bs, 1H), 5.36 (d, J=23.0 Hz, 2H), 5.12 (d, J=28.0 Hz, 1H), 5.02 (d, J=30.0 Hz, 2H), 4.76 (d, J=29.0 Hz, 1H), 4.58 (d, J=37.0 Hz, 3H), 3.95 (m, 6H), 3.42 (bs, 5H), 3.0 (bs, 6H), 2.63 (s, 3H), 2.49-2.02 (m, 8H), 1.64 (s, 3H), 1.36-1.10 (m, 6H), 0.51 (bs, 3H), 0.00 (bs, 3H).

Example 16

3-[[[4-[4-(6S-2-Nitro-6,7-dihydro-5H-imidazo[2,1-b][1,3]oxazin-6-yloxymethyl)-benzyl]-piperazin-1-yl]imino]methyl]rifamycin SV

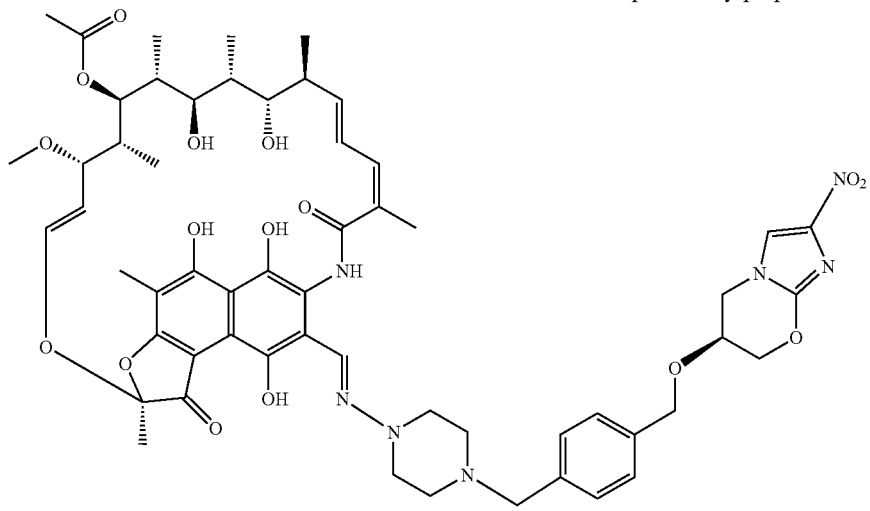

Step 1. 3-(piperazin-1-yliminomethyl)-Rifamycin SV. A suspension of 2,2,2-trifluoro-N-piperazin-1-yl-acetamide (100 mg, 0.51 mmol) and $K_2CO_3$ (350 mg, 2.5 mmol) in aqueous methanol (50:1) was refluxed over night. The reaction mixture was cooled to room temperature and the solid was filtered off. The solution was concentrated, pH was adjusted to 4-5 with HOAc and added a solution of 3-bromo-rifamycin (373.0 mg, 0.5 mmol) in THF. The reaction mixture was stirred overnight at room temperature. The reaction mixture was diluted with ethyl acetate and washed with water and saturated brine. The organic layer was dried over anhydrous $Na_2SO_4$, filtered and evaporated. The residue was purified by silica gel column chromatography (5% MeOH in $CH_2Cl_2$) to give the title product as orange solid (210.0 mg, 52%). ESI MS m/z 809 (M+H$^+$).

Step 2. 3-({4-[4-(2-Nitro-6,7-dihydro-5H-imidazo[2,1-b][1,3]oxazin-6-yloxymethyl)-benzyl]-piperazin-1-ylimino}-methyl)-rifamycin SV. A solution of 3-(piperazin-1-yliminomethyl)-rifamycin SV (210 mg, 0.22 mmol), 6-(4-chloromethyl-benzyloxy)-2-nitro-6,7-dihydro-5H-imidazo[2,1-b][1,3]oxazine (86.0 mg, 0.22 mmol) and DIPEA (99.3 mg, 0.77 mmol) in IPA was stirred at room temperature overnight. The mixture was diluted with DCM and washed with water and saturated brine. The organic layer was dried over anhydrous $Na_2SO_4$, filtered and evaporated. The residue was purified by preparative TLC (5% MeOH in $CH_2Cl_2$) to give the title product as orange solid (6 mg, 3.0%). ESI MS m/z 1096 (M+H$^+$); $^1$H NMR (400 MHz, CDCl$_3$) δ 13.8 (s, 1H), 13.56 (bs, 1H), 12.33 (s, 1H), 8.58 (s, 1H), 7.70-7.57 (m, 6H), 6.87 (m, 1H), 6.66 (d, J=27.0 Hz, 1H), 6.54 (d, J=31.0 Hz, 1H), 6.22 (dd, J=10.38 Hz, 1H), 5.42 (m, 1H), 5.25 (d, J=26 Hz, 1H), 5.03 (d, J=29 Hz, 1H), 4.94 (m, 2H), 4.65 (d, J=31.0 Hz, 1H), 4.46 (m, 3H), 4.08 (d, J=23.0 Hz, 1H), 3.94-3.86 (m, 3H), 3.78 (bs, 2H), 3.47-3.31 (m, 4H), 2.90 (bs, 3H), 2.69 (bs, 1H), 2.07 (s, 2H), 2.38 (m, 5H), 2.11 (s, 3H), 1.94 (m, 6H), 1.69-1.56 (m, 4H), 1.33 (d, J=16.0 Hz, 3H), 1.21 (d, J=17.0 Hz, 3H), 0.92 (d, J=18.0 Hz, 3H), 0.09 (d, J=18.0 Hz, 3H).

Example 17

4-Deoxy-3,4-[2-spiro-[1-[[4-(6S-2-nitro-6,7-dihydro-5H-imidazo[2,1-b][1,3]oxazin-6-yloxymethyl)-phenoxy]-acetyl]-piperidin-4-yl]-(1H)-imidazo-(2,5-dihydro)rifamycin

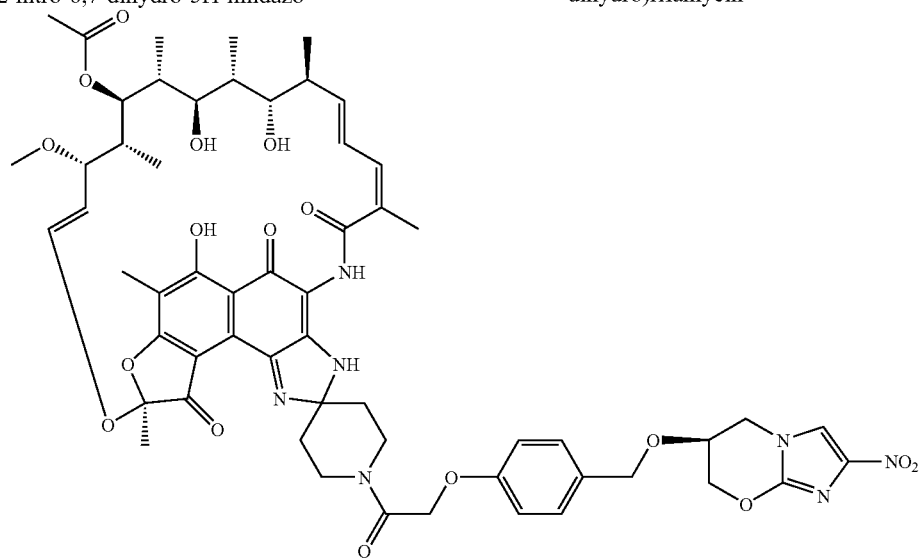

Step 1. (4-Hydroxymethyl-phenoxy)-acetic acid tert-butyl ester. A suspension of 4-hydroxymethyl-phenol (3.70 g, 30 mmol), bromo-acetic acid tert-butyl ester (6.0 mL, 40 mmol), $K_2CO_3$ (16.6 g, 120 mmol) in acetonitrile (100 mL) was stirred at 60° C. for 16 h under $N_2$. The reaction mixtures were filtered, and the solvent was removed under reduced pressure to provide the crude product that was purified by flash chromatography over silica eluting with EtOAc/hexane afforded the title product as oil (6.22 g, 87%). $^1$H NMR (400 MHz, $CDCl_3$) δ 7.29 (d, J=8.0 Hz, 2H), 6.88 (d, J=8.4 Hz, 2H), 4.62 (d, J=5.6 Hz, 2H), 4.52 (s, 2H), 1.49 (s, 9H).

Step 2. (4-Chloromethyl-phenoxy)-acetic acid tert-butyl ester. To a stirred solution of (4-hydroxymethyl-phenoxy)-acetic acid tert-butyl ester (2.38 g, 10 mmol) in methylene chloride (50 mL) at 0° C. under $N_2$ was added triethylamine (3.5 mL, 25 mmol) and MsCl (1.20 mL, 15 mmol). The mixture was stirred at 0° C. for 1 h and at room temperature for 2 h. The mixture was diluted with methylene chloride and washed with water, 5% $K_2CO_3$ solution and saturated brine. The organic layer is dried over anhydrous $Na_2SO_4$, filtered and evaporated to give the title product as oil (2.40 g, 94%). $^1$H NMR (400 MHz, $CDCl_3$) δ 7.32 (d, J=8.4 Hz, 2H), 6.87 (d, J=8.4 Hz, 2H), 4.56 (s, 2H), 4.51 (s, 2H), 1.48 (s, 9H).

Step 3. [4-(2-Nitro-6,7-dihydro-5H-imidazo[2,1-b][1,3]oxazin-6-yloxylmethyl)-phenoxy]-acetic acid tert-butyl ester. To a stirred solution of 2-nitro-6,7-dihydro-5H-imidazo[2,1-b][1,3]oxazin-6-ol (148 mg, 0.80 mmol) and (4-chloromethyl-phenoxy)-acetic acid tert-butyl ester (300 mg, 1.0 mmol) in dry DMF (8.0 mL) at −60° C. under $N_2$ was added 60% NaH (50 mg, 1.3 mmol). After addition, the solution was allowed to slowly warm to room temperature. The reaction mixture was stirred at room temperature for 1.5 h. The mixture was diluted with EtOAc, washed with water, dried over sodium sulfate, and concentrated in vacuo. The crude product was purified by preparative TLC plates (5% MeOH in dichloromethane) to give the title product (142 mg, 44%). ESI MS m/z 406 (M+H$^+$), 428 (M+Na$^+$); $^1$H NMR (400 MHz, $CDCl_3$) δ 7.38 (s, 1H), 7.23 (d, J=8.4 Hz, 2H), 6.87 (d, J=8.4 Hz, 2H), 4.67-4.53 (m, 3H), 4.52 (s, 2H), 4.31 (d, J=11.6 Hz, 1H), 4.15-4.06 (m, 3H), 1.49 (s, 9H).

Step 4. 1-{2-[4-(2-Nitro-6,7-dihydro-5H-imidazo[2,1-b][1,3]oxazin-6-yloxymethyl)-phenoxy]-acetyl}-piperidin-4-one. A solution of [4-(2-nitro-6,7-dihydro-5H-imidazo[2,1-b][1,3]oxazin-6-yloxylmethyl)-phenoxy]-acetic acid tert-butyl ester (130 mg, 0.32 mmol) in TFA (1.0 mL) and dichloromethane (2.0 mL) was stirred at room temperature for 1.5 h. Solvent was evaporated to give [4-(2-nitro-6,7-dihydro-5H-imidazo[2,1-b][1,3]oxazin-6-yloxymethyl)-phenoxy]-acetic acid. To a solution of the above acid in dichloromethane (6.0 mL) under $N_2$ was added diisopropylethylamine (0.20 mL), 4-piperidone hydrochloride monohydrate (98 mg, 0.64 mmol), 1-(3-dimethylaminopropyl)-3-ethylcarbodiimide hydrochloride (80 mg, 0.42 mmol), 1-hydrobenzotriazole (52 mg, 0.38 mmol). The mixture was stirred at room temperature for 24 h. The reaction mixture was diluted with dichloromethane, washed with saturated $NaHCO_3$ and 1 N HCl solution, dried over sodium sulfate, and concentrated in vacuo. The crude product was purified by preparative TLC plates (5% MeOH in dichloromethane) to give the title product as oil (28.0 mg, 20%). ESI MS m/z 431 (M+H$^+$); $^1$H NMR (400 MHz, $CDCl_3$) δ 7.37 (s, 1H), 7.26 (d, J=8.4 Hz, 2H), 6.94 (d, J=8.4 Hz, 2H), 4.77 (s, 2H), 4.67-4.53 (m, 3H), 4.32 (d, J=12.0 Hz, 1H), 4.15-4.07 (m, 3H), 3.91-3.85 (m, 4H), 2.50-2.45 (m, 4H).

Step 5. 4-Deoxy-3,4-[2-spiro-[1-{2-[4-(2-Nitro-6,7-dihydro-5H-imidazo[2,1-b][1,3]oxazin-6-yloxymethyl)-phenoxy]-acetyl}-piperidin-4-yl]]-(2,5-dihydro)rifamycin S. To a stirred solution of 1-{2-[4-(2-Nitro-6,7-dihydro-5H-imidazo[2,1-b][1,3]oxazin-6-yloxymethyl)-phenoxy]-acetyl}-piperidin-4-one (27 mg, 0.063 mmol) and ammonium acetate (48 mg) in THF (2.0 mL) was added 3-amino-4-deoxy-4-imino-rifamycin S (45 mg) and Zinc (4.0 mg). The reaction mixture was stir at room temperature for 2 h. The mixture was partitioned between water and ethyl acetate, and organic layer was separated, dried over sodium sulfate, and concentrated in vacuo to give a crude product which was purified by preparative TLC (10% methanol in dichloromethane) to give the title compound as a dark-purple solid (38.0 mg, 54%). ESI MS m/z 1122 (M+H$^+$); $^1$H NMR (400 MHz, $CDCl_3$) δ 8.93 (s, 1H), 8.87 (s, 1H), 8.35 (s, 1H), 7.42 (s, 1H), 7.27 (d, J=8.4 Hz, 2H), 7.00 (d, J=8.4 Hz, 2H), 6.42 (dd, J=14.8 and 10.4 Hz, 1H), 6.33 (d, J=10.0 Hz, 1H), 6.22 (dd, J=13.2 and 3.2 Hz, 1H), 6.04 (dd, J=14.8 and 6.0 Hz, 1H), 5.14 (dd, J=12.0 and 5.6 Hz, 1H), 4.84-4.59 (m, 6H), 4.39 (dd, J=12.0 and 4.4 Hz, 1H), 4.23-4.08 (m, 4H), 3.97-3.92 (m, 2H), 3.73-3.69 (m, 2H), 3.83 (t, J=8.8 Hz, 1H), 3.14 (s, 3H), 3.08-3.04 (m, 1H), 2.56-2.51 (m, 2H), 2.39 (s, 3H), 2.19-1.83 (m, 4H), 2.15 (s, 3H), 2.07 (s, 3H), 1.80 (s, 3H), 1.56-1.45 (m, 2H), 1.08 (d, J=4.8 Hz, 3H), 0.88 (d, J=5.6 Hz, 3H), 0.66 (d, J=4.8 Hz, 3H), −0.01 (d, J=4.8 Hz, 3H).

Example 18

3-[4-[1-[4-(6S-2-Nitro-6,7-dihydro-5H-imidazo[2,1-b][1,3]oxazin-6-yloxymethyl)-benzyl]-1H-[1,2,3]triazol-4-ylmethyl]-piperazin-1-yl]-rifamycin S

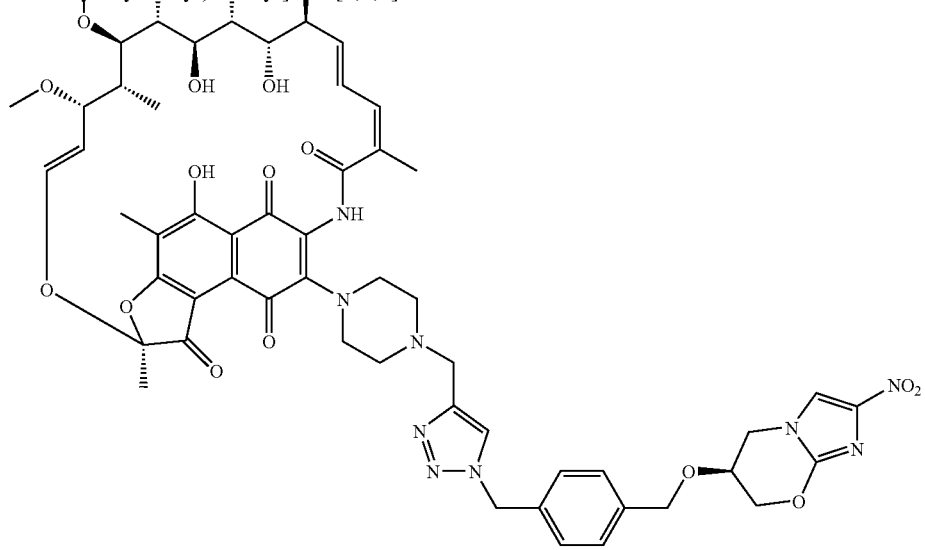

Step 1. 6-(4-Azidomethyl-benzyloxy)-2-nitro-6,7-dihydro-5H-imidazo[2,1-b][1,3]oxazine. A suspension of 6-(4-chloromethyl-benzyloxy)-2-nitro-6,7-dihydro-5H-imidazo[2,1-b][1,3]oxazine (650 mg, 2.0 mmol) and NaN$_3$ (780 mg, 12 mmol) in acetonitrile (20 mL) was stirred at 75° C. for 24 h. The reaction mixture was filtered, and solvents were removed under removed reduced pressure to give the title product as a yellowish solid (0.65 g, 98%). ESI MS m/z 331 (M+H$^+$); $^1$H NMR (400 MHz, CDCl$_3$) δ 7.37 (s, 1H), 7.33-7.32 (m, 4H), 4.74 (d, J=12.0 Hz, 1H), 4.64-4.59 (m, 2H), 4.36-4.33 (m, 3H), 4.19-4.11 (m, 3H).

Step 2. 3-(4-Prop-2-ynyl-piperazin-1-yl)-rifamycin S. A solution of 1-prop-2-ynyl-piperazine (149 mg, 1.2 mmol), 3-bromorifamycin S (775 mg, 1.0 mmol) and triethylamine (0.30 mL, 2.0 mmol) in dichloromethane (20 mL) was stirred at room temperature for 1 h. The reaction mixture were diluted with dichloromethane, washed with saturated sodium bicarbonate solution, dried over sodium sulfate, and concentrated in vacuo. The crude product was purified by flash chromatography on silica eluting with 5% MeOH in dichloromethane to give the title product as a dark purple solid (650 mg, 80%). ESI MS m/z 818.3 (M+H$^+$).

Step 3. 3-(4-{1-[4-(2-Nitro-6,7-dihydro-5H-imidazo[2,1-b][1,3]oxazin-6-yloxymethyl)-benzyl]-1H-[1,2,3]triazol-4-ylmethyl}-piperazin-1-yl)-rifamycin S. To a solution of 3-(4-prop-2-ynyl-piperazin-1-yl)-rifamycin S (50 mg, 0.061 mmol) and 6-(4-azidomethyl-benzyloxy)-2-nitro-6,7-dihydro-5H-imidazo[2,1-b][1,3]oxazine (20 mg, 0.061 mmol) in THF under nitrogen was added Cu (8 mg, 0.061 mmol), CuSO$_4$ (0.024 mL, 0.25 N in water) and water (2.5 mL). The reaction mixture was stirred at room temperature under nitrogen for 24 h. The solvent was removed under reduced pressure and the crude product was purified by preparative TLC (5% MeOH in dichloromethane) to afford the title product as dark purple solid (37.5 mg, 54%). ESI MS m/z 1148.8 (M+H$^+$).

Example 19

3'-Hydroxy-5'-[4-[1-[4-(6S-2-nitro-6,7-dihydro-5H-imidazo[2,1-b][1,3]oxazin-6-yloxymethyl)-benzyl]-1H-[1,2,3]triazol-4-ylmethyl]-piperazin-1-yl]-benzoxazinorifamycin S

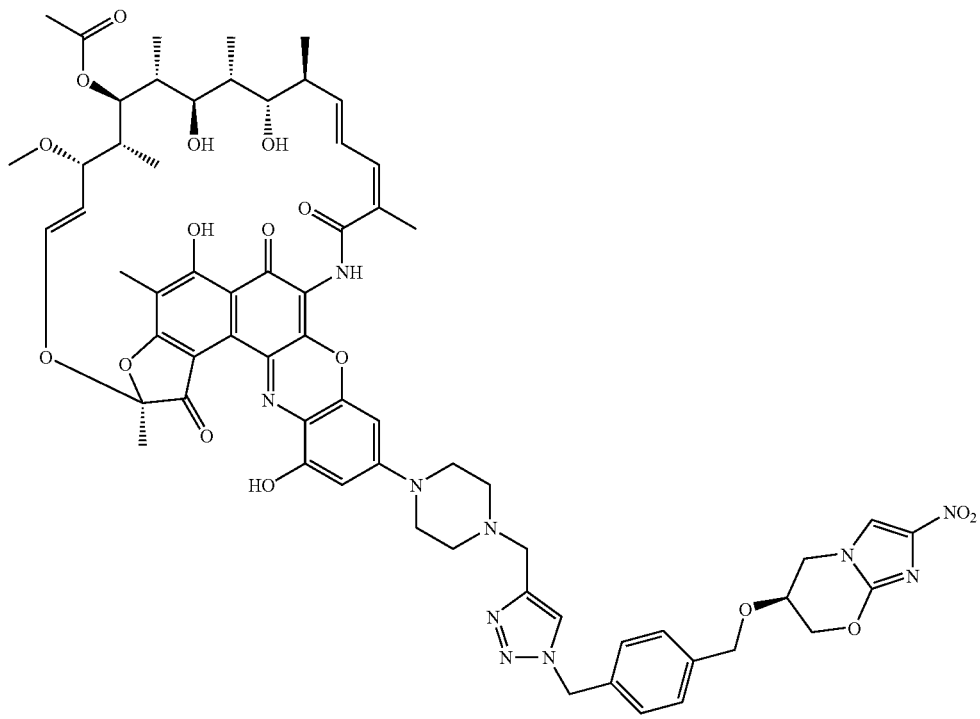

Step 1. 3'-Hydroxy-5'-(4-prop-2-ynyl-piperazin-1-yl)-benzoxazinorifamycin. To a stirred solution of 3'-hydroxy-benzoxazinorifamycin (1.77 g) in DMSO (18 mL) was added 1-prop-2-ynyl-piperazine (0.65 g, 5.2 mmol) and $MnO_2$ (1.8 g). The mixture was allowed to stir at room temperature for 3 days. The mixture was partitioned between water and ethyl acetate. The organic layer was separated, dried over sodium sulfate, concentrated in vacuo. The residue is purified by flash chromatography over silica (5% methanol in dichloromethane) to give dark-blue solid (1.50 g, 72%). ESI MS m/z 923.3 ($M+H^+$).

Step 2. 3'-Hydroxy-5'-(4-{1-[4-(2-nitro-6,7-dihydro-5H-imidazo[2,1-b][1,3]oxazin-6-yloxymethyl)-benzyl]-1H-[1,2,3]triazol-4-ylmethyl}-piperazin-1-yl)-benzoxazinorifamycin. To a solution of 3-hydroxy-5-(4-prop-2-ynyl-piperazin-1-yl)-benzoxazinorifamycin (56.3 mg, 0.061 mmol) and 6-(4-azidomethyl-benzyloxy)-2-nitro-6,7-dihydro-5H-imidazo[2,1-b][1,3]oxazine (20 mg, 0.061 mmol) in THF under nitrogen was added Cu (8 mg, 0.061 mmol), $CuSO_4$ (0.024 mL, 0.25 N in water) and water (2.5 mL). The reaction mixture were stirred at room temperature under nitrogen for 20 h. The solvents were removed under reduced pressure and the crude product was purified by preparative TLC (5% MeOH in dichloromethane) to afford the title product as dark blue solid (26.3 mg, 34%). ESI MS m/z 1253.5 ($M+H^+$).

Example 20

3'-Hydroxy-5'-{4-[4-(2-methyl-6-nitro-2,3-dihydro-imidazo[2,1-b]oxazol-2-ylmethoxy)-phenyl]-piperazin-1-yl}-benzoxazinorifamycin

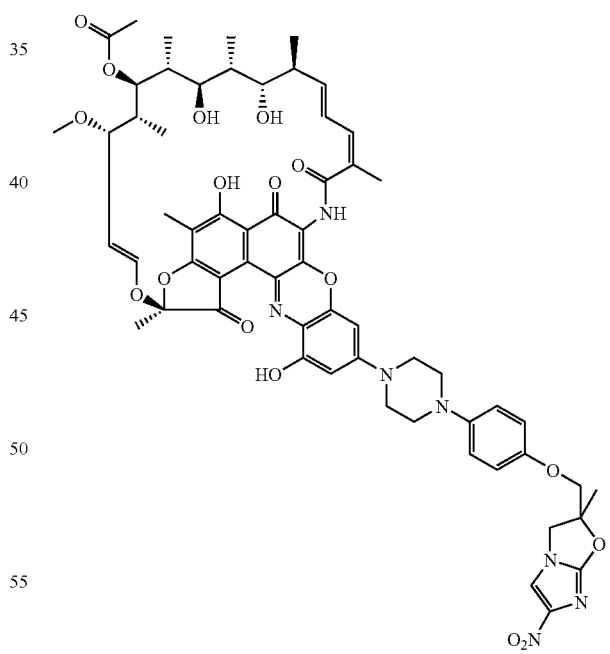

Step 1: 4-[4-(2-Methyl-6-nitro-2,3-dihydro-imidazo[2,1-b]oxazol-2-ylmethoxy)-phenyl]-piperazine-1-carboxylic acid tert-butyl ester: tert-Butyl 4-(4-hydroxyphenyl)piperazine-1-carboxylate (1.5 g, 5.4 mmol) and 2-bromo-1-(2-methyl-oxiranylmethyl)-4-nitro-1H-imidazole (1.96 g, 7.5 mmol) are dissolved in DMF (100 ml) and sodium hydride (0.39 g, 9.7 mmol, 60% in mineral oil) is added at room temperature. Once gas evolution ceases the mixture is heated to 60° C. for 1 h. The mixture is cooled, diluted with water and extracted with ethyl acetate. The combined extracts are purified by silica gel chromatography (1% methanol in methylene chloride) to give 2.2 g (88%) of the product as a tan solid. ESI MS m/z 482 (M+Na$^+$); $^1$H NMR (400 MHz, CDCl$_3$) δ 7.58 (s, 1H), 6.87 (d, J=8.8 Hz, 2H), 6.78 (d, J=8.8 Hz, 2H), 4.48 (d, 10 Hz, 1H), 4.18 (d, J=10.4 Hz, 1H), 4.02 (t, J=9.2 Hz, 1H), 4.0-3.55 (m, 4H), 3.05-2.99 (m, 4H), 1.77 (s, 2H), 1.57 (s, 9H), 1.47 (s, 3H).

Step 2: 2-Methyl-6-nitro-2-(4-piperazin-1-yl-phenoxymethyl)-2,3-dihydro-imidazo[2,1-b]oxazole. 4-[4-(2-Methyl-6-nitro-2,3-dihydro-imidazo[2,1-b]oxazol-2-ylmethoxy)-phenyl]-piperazine-1-carboxylic acid tert-butyl ester is treated with trifluoroacetic acid (5 ml) and stirred at room temperature for 1 hr. The mixture is concentrated and 2-methyl-6-nitro-2-(4-piperazin-1-yl-phenoxymethyl)-2,3-dihydro-imidazo[2,1-b]oxazole is isolated as a dark oil and used for subsequent step without further purification.

Step 3: 3'-Hydroxy-5'-{4-[4-(2-methyl-6-nitro-2,3-dihydro-imidazo[2,1-b]oxazol-2-ylmethoxy)-phenyl]-piperazin-1-yl}-benzoxazinorifamycin. The title compound was prepared as described for Example 4, 3'-hydroxy-5'-[4-[2-(2-metykl-5-nitro-imidazol-1-yl)ethyl]-1-piperazinyl] benzorifamycin using 2-methyl-6-nitro-2-(4-piperazin-1-yl-phenoxymethyl)-2,3-dihydro-imidazo[2,1-b]oxazole and 3'-hydroxybenzoxazino rifamycin. ESI MS m/z 1158 (M+H$^+$); $^1$H NMR (400 MHz, CDCl$_3$) δ 11.08-11.0 (m, 1H), 10.10-9.95 (m, 1H), 9.25-9.20 (m, 1H), 8.08 (s, 1H), 6.88-6.62 (m, 4H), 6.45-6.40 (m, 1H), 6.40-6.35 (m, 1H), 6.35-6.0 (m, 1H), 5.98-5.80 (m, 1H), 5.20-5.1 (m, 1H), 5.1-4.95 (m, 1H), 4.60-4.35 (m, 2H), 4.20-4.15 (m, 2H), 4.03-3.93 (m, 4H), 3.80-3.42 (m, 4H), 3.80-3.40 (m, 4H), 3.40-3.15 (m, 4H), 2.30-2.20 (m, 2H), 2.20-1.93 (m, 6H), 1.95-1.42 (m, 6H), 1.40-1.23 (m, 6H), 1.20-0.60 (m, 9H), 0.08-0.05 (m, 3H).

Example 21

3-(2-{4-[4-(2-Methyl-6-nitro-2,3-dihydro-imidazo[2,1-b]oxazol-2-ylmethoxy)-phenyl]-piperazin-1-yl}) Rifamycin S

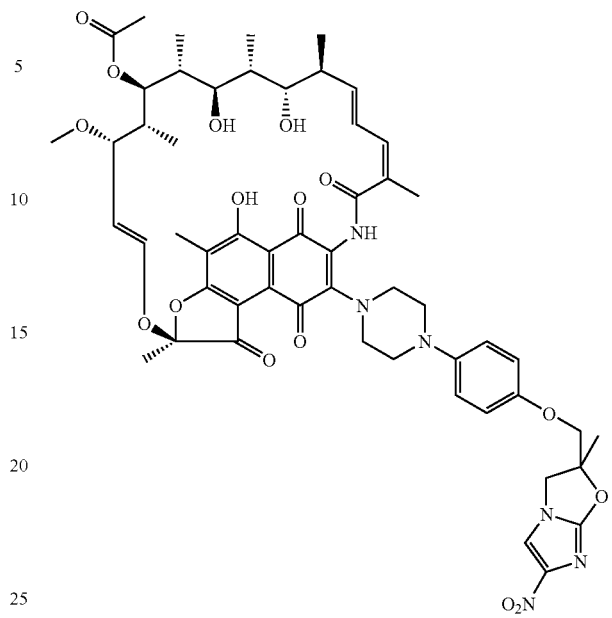

To a solution of 3-bromorifamycin (200 mg, 0.26 mmol), and 2-methyl-6-nitro-2-(4-piperazin-1-yl-phenoxymethyl)-2,3-dihydro-imidazo[2,1-b]oxazole (150 mg, 0.42 mmol) in dichloromethane (20 ml) is added triethylamine (0.12 ml, 0.50 mmol) and the mixture stirred at room temperature for 2 h. The reaction is diluted with dichloromethane (50 ml) and washed with 5% citric acid. The organic layer is separated, dried over sodium sulfate and concentrated. The purple residue is purified by preparative TLC (10% methanol in dichloromethane) to give title compound as a purple solid (115 mg, 36%). ESI MS m/z 1053.37 (M+H$^+$); $^1$H NMR (400 MHz, CDCl$_3$) δ 13.29 (s, 1H), 7.58-7.49 (m, 2H), 7.18-7.12 (m, 4H), 6.90-6.82 (m, 2H), 6.80-6.72 (m, 2H), 6.42-6.34 (m, 1H), 6.13-6.02 (m, 2H), 5.18-5.06 (m, 2H), 4.57-4.42 (m, 1H), 4.21-4.12 (m, 1H), 4.10-4.00 (m, 4H), 3.72-3.60 (m, 2H), 3.57-3.40 (m, 2H), 3.10-3.00 (m, 3H), 2.20-2.01 (m, 7H), 1.91-1.64 (m, 6H), 1.60-1.44 (m, 10H), 1.38-1.20 (m, 1H), 1.05-0.95 (m, 3H), 291-2.78 (m, 3H), 2.71-2.64 (m, 3H), 0.24-0.20 (m, 3H).

Example 22

3-[4-(2-{4-[4-(2-methyl-6-nitro-2,3-dihydro-imidazo[2,1-b]oxazol-2-ylmethoxy)-phenyl]-piperazin-1-yl}-acetyl)-piperazin-1-yl]-rifamycin S

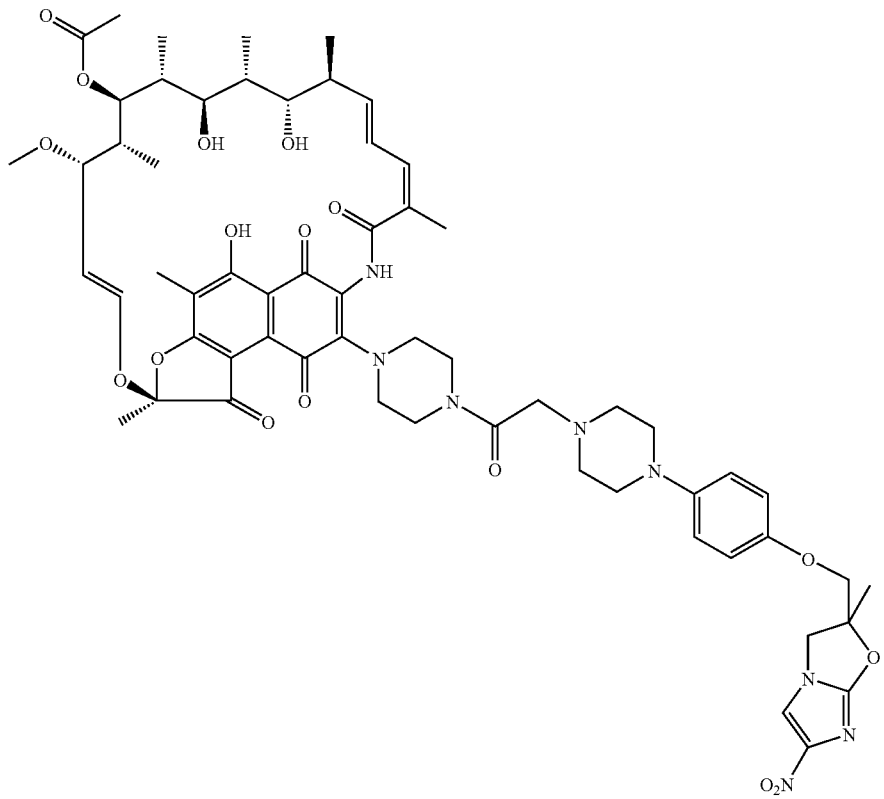

Step 1: 4-Carboxymethyl-piperazine-1-carboxylic acid tert-butyl ester: A solution of 4-ethoxycarbonylmethyl-piperazine-1-carboxylic acid tert-butyl ester (1.3 g, 4.78 mmol) in methanol (50 ml) was treated with NaOH (1N, 10 ml, 10 mmol) and stirred for 4 h. The mixture is concentrated and the residue is adjusted to pH 6 with 5% citric acid solution. The mixture is extracted with ethyl acetate, dried over sodium sulfate and concentrated to give 4-carboxymethyl-piperazine-1-carboxylic acid tert-butyl ester, 445 mg (38%) as a white solid. ESI MS m/z 1179 (M+H$^+$); $^1$H NMR (400 MHz, CDCl$_3$) δ 3.80-3.60 (m, 4H), 3.42 (s, 2H), 3.10-2.84 (m, 4H), 1.24 (s, 9H).

Step 2: 4-(2-{4-[4-(2-Methyl-6-nitro-2,3-dihydro-imidazo[2,1-b]oxazol-2-ylmethoxy)-phenyl]-piperazin-1-yl}-2-oxo-ethyl)-piperazine-1-carboxylic acid tert-butyl ester. A solution of 2-methyl-6-nitro-2-(4-piperazin-1-yl-phenoxymethyl)-2,3-dihydro-imidazo[2,1-b]oxazole (200 mg, 0.34 mmol) and 4-carboxymethyl-piperazine-1-carboxylic acid tert-butyl ester (136 mg, 0.55 mmol) in DMF is treated with TBTU (179.8 mg, 0.55 mmol), triethyl amine (0.23 ml, 1.65 mmol) and stirred for 2 h. The mixture is diluted with water and extracted with ethyl acetate. The organic layer is dried over sodium sulfate and concentrated. The residue is purified by preparative TLC (10% methanol in dichloromethane to give 4-(2-{4-[4-(2-methyl-6-nitro-2,3-dihydro-imidazo[2,1-b]oxazol-2-ylmethoxy)-phenyl]-piperazin-1-yl}-2-oxo-ethyl)-piperazine-1-carboxylic acid tert-butyl ester as yellow oil (152 mg, 78%). ESI MS m/z 585 (M+H); $^1$H NMR (400 MHz, CDCl$_3$) δ 8.01 (s, 1H), 6.83 (d, J=8.4 Hz, 2H), 6.78 (d, J=8.4 Hz, 2H), 4.48 (d, J=Hz), 4.18 (d, J=Hz, 1H), 4.14-4.02 (m, 2H), 3.82-3.71 (m, 4H), 3.56-3.38 (m, 4H), 2.91 (s, 2H), 2.52-2.42 (m, 4H), 1.75-1.62 (m, 4H), 1.42 (s, 9H).

Step 3: 1-{4-[4-(2-Methyl-6-nitro-2,3-dihydro-imidazo[2,1-b]oxazol-2-ylmethoxy)-phenyl]-piperazin-1-yl}-2-piperazin-1-yl-ethanone. The title compound is prepared as described in Example 20, step 2 for the preparation of 2-methyl-6-nitro-2-(4-piperazin-1-yl-phenoxymethyl)-2,3-dihydro-imidazo[2,1-b]oxazole. The product was used without further purification.

Step 4: 3-(2-Amino-3-[4-(2-{4-[4-(2-methyl-6-nitro-2,3-dihydro-imidazo[2,1-b]oxazol-2-ylmethoxy)-phenyl]-piperazin-1-yl}-acetyl)-piperazin-1-yl])-rifamycin S. The title compound was prepared as described for the preparation of Example 21, 3-(2-{4-[4-(2-methyl-6-nitro-2,3-dihydro-imidazo[2,1-b]oxazol-2-ylmethoxy)-phenyl]-piperazin-1-yl}) rifamycin S from 3-bromorifamycin and 1-{4-[4-(2-methyl-6-nitro-2,3-dihydro-imidazo[2,1-b]oxazol-2-ylmethoxy)-phenyl]-piperazin-1-yl}-2-piperazin-1-yl-ethanone. ESI MS m/z 1179 (M+H$^+$); $^1$H NMR (400 MHz, CDCl$_3$) δ 13.02 (s, 1H), 7.69 (s, 1H), 7.54 (s, 1H), 6.85 (d, J=8.4 Hz, 2H), 6.72 (d, J=8.4 Hz, 2H), 6.29 (d, J=10.4 Hz, 2H), 6.18-6.05 (m, 1H), 5.98 (d, J=12.8 Hz, 1H), 5.08-5.01 (m, 2H), 4.43 (d, J=10 Hz, 1H), 4.13 (d, J=10.4 Hz, 2H), 3.99-3.97 (m, 2H), 3.87-3.82 (m, 2H), 3.90-3.32 (m, 9H), 3.30-3.18 (m, 2H), 3.05-2.85 (m, 4H), 3.03 (s, 3H), 2.26 (s, 3H), 2.04 (s, 3H), 2.00 (s, 3H), 1.80-1.40 (m, 6H), 1.74 (s, 3H), 1.67 (s, 3H), 1.50-1.20 (m, 3H), 0.96 (d, J=6.8 Hz, 3H), 0.82 (d, J=7.2 Hz, 3H), 0.67 (d, J=6.4 Hz, 3H), 0.90-0.88 (m, 3H).

Example 23

4-Deoxy-3,4-[2-spiro-[1-[2-(2-nitro-6,7-dihydro-5H-imidazo[2,1-b][1,3]oxazin-6-yloxy)-acetyl]-piperidin-4-yl]]-(1H)-imidazo-(2,5-dihydro)rifamycin S

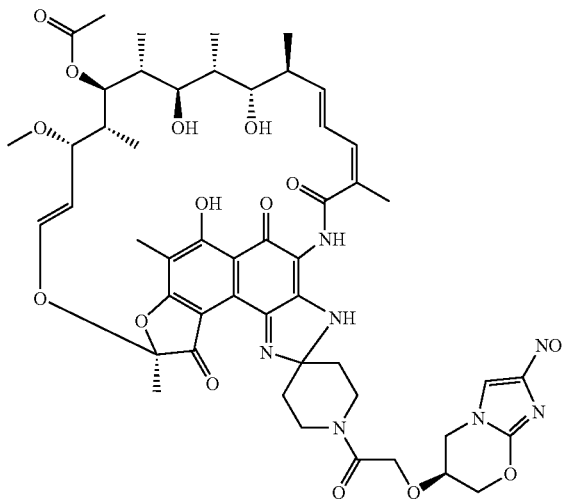

To a stirred solution of 1-[2-(6S-2-nitro-6,7-dihydro-5H-imidazo[2,1-b][1,3]oxazin-6-yloxy)-acetyl]-piperidin-4-one (84 mg, 0.26 mmol) and ammonium acetate (20 mg, 0.26 mmol) in THF (10 mL) is heated to reflux then cooled and 3-amino-4-deoxy-4-imino-rifamycin S (71 mg, 0.1 mmol) prepared by following a literature report (U.S. Pat. No. 4,017,481) is added and allowed to stir for 4 h. The mixture is diluted with ethyl acetate and washed with water and saturated brine. The organic layer is dried over anhydrous $Na_2SO_4$, filtered and evaporated. The residue is purified by silica gel column chromatography (7% MeOH in $CH_2Cl_2$) to give the title product as dark purple solid. ESI MS m/z 1016 (M+H+); $^1$H NMR (400 MHz, CDCl$_3$) δ 8.86 (d, J=8.8 Hz, 1H), 8.37 (s, 1H), 8.30 (s, 1H), 7.50 (s, 1H), 6.49-6.39 (m, 1H), 6.38-6.33 (m, 1H), 6.25-6.21 (m, 1H), 6.09-6.01 (m, 1H), 5.21-5.16 (m, 1H), 4.81-4.75 (m, 2H), 4.59-4.58 (m, 1H), 4.51-4.25 (m, 4H), 4.0-3.48 (m, 7H), 3.48-3.34 (m, 1H), 3.30-3.20 (m, 1H), 2.40 (s, 3H), 2.20-2.0 (m, 5H), 2.07 (s, 3H), 1.81-1.60 (m, 5H), 1.41-1.21 (m, 8H), 1.09 (d, J=7.2 Hz, 3H), 0.92 (d, J=6.8 Hz, 3H), 0.02 (d, J=6.4 Hz, 3H), −1.44 (d, J=7.2 Hz, 3H).

Example 24

2-[4-(2-Bromo-4-nitro-imidazol-1-ylmethyl)-4-hydroxy-piperidin-1-yl]-rifamycin S

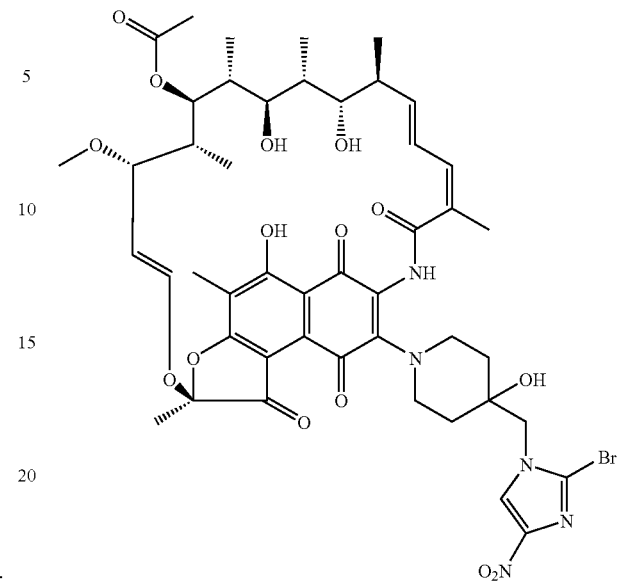

The title compound is prepared as described for example 21, 3-(2-{4-[4-(2-methyl-6-nitro-2,3-dihydro-imidazo[2,1-b]oxazol-2-ylmethoxy)-phenyl]-piperazin-1-yl}) rifamycin S from 3-bromorifamycin and 4-(2-bromo-4-nitro-imidazol-1-ylmethyl)-piperidin-4-ol and isolated as a purple solid (18 mg, 15%); ESI MS m/z 998 (M+H+); $^1$H NMR (400 MHz, CDCl$_3$) δ 7.58-7.44 (m, 1H), 7.42 (2, 1H), 7.31 (s, 1H), 7.09-6.92 (m, 1H), 6.90-6.80 (m, 1H), 5.98-5.90 (m, 1H), 4.80-4.70 (m, 1H), 4.70-4.62 (m, 1H), 4.42-4.20 (m, 6H), 4.11-4.01 (m, 1H), 3.80-3.62 (m, 4H), 3.62-3.51 (m, 4H), 3.44 (s, 3H), 3.10-2.80 (m, 4H), 2.01 (s, 3H), 1.70-1.40 (m, 17H), 1.31-1.20 (m, 6H).

Example 25

3-{4-[2-(6S-2-Nitro-6,7-dihydro-5H-imidazo[2,1-b][1,3]oxazin-6-yloxy)-acetyl]-piperazin-1-yl}-rifamycin S

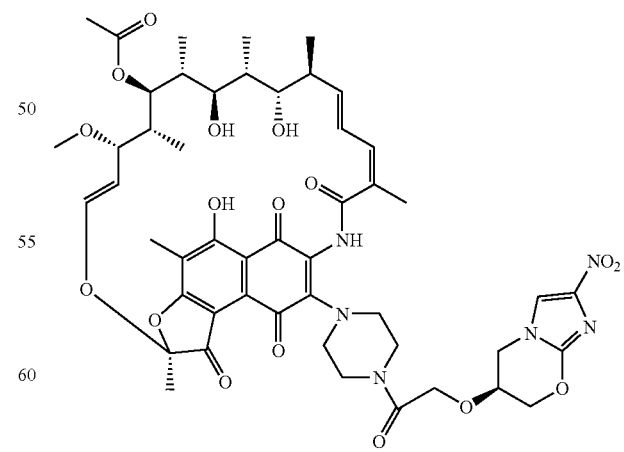

Step 1: 4-[2-(6S-2-Nitro-6,7-dihydro-5H-imidazo[2,1-b][1,3]oxazin-6-yloxy)-acetyl]-piperazine-1-carboxylic acid tert-butyl ester. A solution of 4-(2-bromo-acetyl)-piperazine- 1-carboxylic acid tert-butyl ester (0.39 g, 1.3 mmol) and 2-nitro-6,7-dihydro-5H-imidazo[2,1-b][1,3]oxazin-6S-ol (0.2 g, 1.08 mmol) in DMF (9 ml) was cooled to −60° C. and treated with sodium hydride (50 mg, 1.3 mmol) and warmed to room temperature over 2 h. The mixture was diluted with ethyl acetate, washed with water dried over sodium sulfate and concentrated. The residue is purified by silica gel chromatography (5% methanol in dichloromethane) to give 4-[2-(2-nitro-6,7-dihydro-5H-imidazo[2,1-b][1,3]oxazin-6S-yloxy)-acetyl]-piperazine-1-carboxylic acid tert-butyl ester as a yellow oil (314 mg, 77%). ESI MS m/z 434 (M+Na$^+$); $^1$H NMR (400 MHz, CDCl$_3$) δ 7.48 (s, 1H), 4.48-4.40 (m, 1H), 4.40-4.22 (m, 4H), 3.38-3.44 (s, 2H), 3.42-3.30 (m, 8H), 1.42 (s, 9H).

Step 2: 3-{4-[2-(6S-2-Nitro-6,7-dihydro-5H-imidazo[2,1-b][1,3]oxazin-6-yloxy)-acetyl]-piperazin-1-yl}-rifamycin S. The title compound was prepared as described for example 21, 3-(2-{4-[4-(2-methyl-6-nitro-2,3-dihydro-imidazo[2,1-b]oxazol-2-ylmethoxy)-phenyl]-piperazin-1-yl}) rifamycin S starting from 3-bromorifamycin and 4-[2-(2-nitro-6,7-dihydro-5H-imidazo[2,1-b][1,3]oxazin-6-yloxy)-acetyl]-piperazine-1-carboxylic acid tert-butyl ester. ESI MS m/z 1027 (M+Na$^+$); $^1$H NMR (400 MHz, CDCl$_3$) δ 13.0 (s, 1H), 7.56 (s, 1H), 7.04 (m, 1H), 6.33 (d, J=11.2 Hz, 1H), 6.15 (dd, J=6.4, 15.6 Hz, 1H), 5.98 (d, J=12.8 Hz, 1H), 5.03 (m, 2H), 4.58 (d, J=12.4 Hz, 1H), 4.33-4.15 (m, 6H), 3.86-3.84 (m, 3H), 3.55-3.23 (m, 8H), 3.03 (s, 3H), 2.98 (d, J=10 Hz, 1H), 2.22 (s, 3H), 2.10 (s, 3H), 2.06 (s, 3H), 1.92-1.40 (m, 4H), 1.72 (s, 3H), 1.18-1.08 (m, 2H), 0.98 (d, J=7.4 Hz, 3H), 0.79 (d, J=7.4 Hz, 3H), 0.64 (d, J=6.8 Hz, 3H), 0.082 (d, J=7.2 Hz, 3H).

Example 26

3-[4-(2-Methyl-6-nitro-2,3-dihydro-imidazo[2,1-b]oxazol-2-ylmethyl)-piperazin-1-yl]rifamycin S

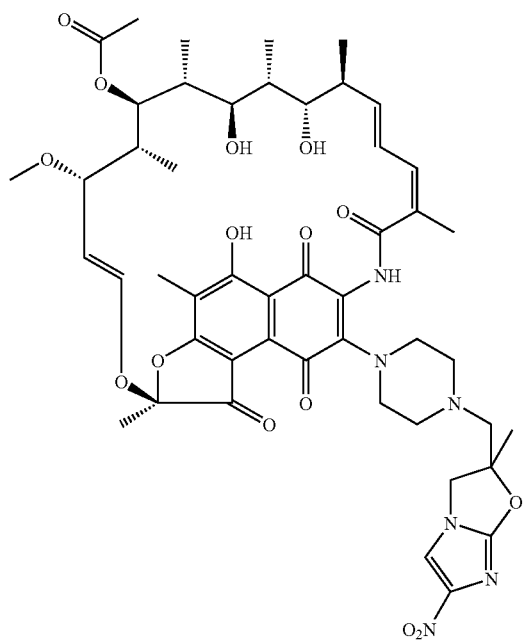

Step 1: 4-(2-Methyl-6-nitro-2,3-dihydro-imidazo[2,1-b]oxazol-2-ylmethyl)-piperazine-1-carboxylic acid tert-butyl ester. A solution of 1-(2-methyl-oxiranylmethyl)-4-nitro-1H-imidazole (1.5 g, 5.72 mmol) and piperazine-1-carboxylic acid tert-butyl ester (1.1 g, 5.72 mmol) is dissolved in IPA and heated to 60° C. for 24 h. The solution is concentrated and partitioned between water and ethyl acetate. The organic layer is dried over sodium sulfate and concentrated. The resulting solution of 4-[3-(2-bromo-4-nitro-imidazol-1-yl)-2-hydroxy-2-methyl-propyl]-piperazine-1-carboxylic acid tert-butyl ester (1.1 g, 2.46 mmol) in DMF (15 ml) was treated with sodium hydride (148 mg, 3.69 mmol) and stirred for 3 h at 60° C. The mixture was diluted with water and extracted with ethyl acetate. The organic layer is dried over sodium sulfate and concentrated. The residue is purified by silica gel chromatography to give 4-(2-methyl-6-nitro-2,3-dihydro-imidazo[2,1-b]oxazol-2-ylmethyl)-piperazine-1-carboxylic acid tert-butyl ester (453 mg, 50%) of as a light yellow oil. ESI MS m/z 367 (M+Na$^+$); $^1$H NMR (400 MHz, CDCl$_3$) δ 7.54 (s, 1H), 4.30 (d, J=10 Hz, 1H), 3.92 (d, J=10 Hz, 1H), 3.45-3.02 (m, 4H), 2.86 (d, J=14.8 Hz, 1H), 2.70-2.39 (m, 4H), 2.55 (d, J=14.8 Hz, 1H), 1.58 (s, 3H), 1.45 (s, 9H).

Step 2: 3-[4-(2-Methyl-6-nitro-2,3-dihydro-imidazo[2,1-b]oxazol-2-ylmethyl)-piperazin-1-yl]rifamycin S. 3-[4-(2-Methyl-6-nitro-2,3-dihydro-imidazo[2,1-b]oxazol-2-ylmethyl)-piperazin-1-yl]rifamycin S was prepared as described for the preparation of example 21, 3-(2-{4-[4-(2-methyl-6-nitro-2,3-dihydro-imidazo[2,1-b]oxazol-2-ylmethoxy)-phenyl]-piperazin-1-yl}) rifamycin S starting from 3-bromorifamycin and 4-(2-methyl-6-nitro-2,3-dihydro-imidazo[2,1-b]oxazol-2-ylmethyl)-piperazine-1-carboxylic acid tert-butyl ester; ESI MS m/z 983 (M+Na$^+$); $^1$H NMR (400 MHz, CDCl$_3$) δ 13.19 (s, 1H), 7.48 (s, 1H), 7.43 (d, J=17.2 Hz, 1H), 7.13-7.90 (m, 1H), 6.27 (dd, J=10.8, 11.1 Hz, 1H), 6.18-6.02 (m, 1H), 5.99 (dd, J=12.8, 4 Hz, 1H), 5.11-4.98 (m, 2H), 4.35 (d, J=9.6 Hz, 1H), 4.22 (d, J=10 Hz, 1H), 3.92-3.79 (m, 3H), 3.52-3.25 (m, 3H), 3.39-3.10 (m, 2H), 3.08-2.70 (m, 3H), 3.02 (s, 3H), 2.70-2.20 (m, 2H), 2.19 (m, 3H), 2.08 (s, 2H), 2.02 (s, 3H), 1.98 (s, 3H), 1.80-1.30 (m, 8H), 1.30-1.10 (m, 3H), 0.99 (d, J=11.6 Hz, 3H), 0.80 (d, J=6.8 Hz, 3H), 0.76 (d, J=7.2 Hz, 3H).

Example 27

Biological Activity

As shown in Table 1 below, the compounds of Examples 1, 3 and 4 demonstrated a potent antibacterial activity.

TABLE 1

Antibacterial Activity of Selected Examples

| Compound | MIC (ug/mL) | | | | |
|---|---|---|---|---|---|
| | S. aureus ATCC# 29213 | H. influenzae ATCC# 10211 | E. coli ATCC# 25922 | H. pylori ATCC# 700392 | H. pylori CB1572 (Rif-resistant) |
| rifampin | 0.008 | 0.24 | 8 | 0.12 | >32 |
| metronidazole | >64 | >64 | >64 | 2 | 2 |
| Example 1 | 0.03 | 1 | 16 | ≦0.03 | 0.5 |
| Example 3 | 0.03 | — | — | 0.5 | 2 |
| Example 4 | <0.004 | — | >8 | ≦0.03 | 1 |

Representative compounds are assayed for antimicrobial activity as follows: Minimum Inhibtory Concentrations (MICs) against *Staphylococcus aureus* ATCC 29213, *Haemophilus influenzae* ATCC 10211 and *Escherichia coli* ATCC 25922 were determined by the microbroth dilution method, against *Helicobacter pylori* ATCC 700392 and its isogenic derivative (CB1572) exhibiting rifamycin-resistance (rpoB$^{L525I, D530N}$), were determined by the agar dilution method, as per NCCLS guidelines (Reference=National Committee for Clinical Laboratory Standards. 2000. Methods for dilution antimicrobial susceptibility tests for bacteria that grow aerobically, 5th ed. M7-A5. National Committee for Clinical Laboratory Standards, Wayne, Pa.). The antimicrobial activity of the example compounds of the current invention and reference compounds, rifampin and metronidazole are shown in Table 1. The inventive compounds display excellent activity against Gram-positive species, for example, *Staphylococcus aureus* ATCC 29213; good activities against Gram-negatives, for example, *Haemophilus influenzae* ATCC 10211 and *Escherichia coli* ATCC 25922. It is to be noted that the inventive compounds exhibit good activity against *Helicobacter pylori* ATCC 700392, and retain activity against a rifamycin-resistant (rpoB$^{L525I, D530N}$) strain of *Helicobacter pylori*. Even more surprising is the activity of Example 1 against a rifamycin-resistant (rpoB$^{L525I, D530N}$) strain of *Helicobacter pylori* (CB1572), which may not be accounted for by simple additive effect of rifamycin and metronidazole, but likely due to unexpected synergistic effect of the inventive compounds.

The current inventive compounds are active against anaerobic bacteria, such as *Clostridium*, for example *C. difficile*; *Bacteroides* for example, *B. fragilis*. The activity of an example is summarized in Table 2. Compounds are potent antibacterials against *Mycobacterium tuberculosis*, Example 1, shown in Table 2 retains activity against rifampin-resistant strain of *Mycobacterium tuberculosis*. This activity against resistant strain of bacteria is not expected by simple combination of rifampin and metronidazole.

TABLE 2

Antibacterial Activity against Selected Bacterium

| Compound | MIC (ug/mL) | | | |
|---|---|---|---|---|
| | Clostridium difficile CB-1620 | Bacteroides fragilis CB-1621 | Mycobacterium tuberculosis H37Rv | Mycobacterium tuberculosis H37Rv (rif-resistant) |
| rifampin | 0.001 | 0.06 | 0.03 | >32 |
| metronidazole | 0.25 | 0.24 | >64 | >64 |
| Example 1 | 0.00025 | 0.03 | 0.016 | 5 |

The present compounds are active against both aerobic and anaerobic bacteria, and accordingly are useful as broad spectrum antibacterial agents. The present compounds are surprisingly effective against a number of human and veterinary aerobic and anaerobic Gram positive, Gram negative pathogens, including the *Staphylococci*, for example *S. aureus*; *Enterococci*, for example *E. faecalis*; *Streptococci*, for example *S. pneumoniae*; *Haemophilus*, for example *H. influenza*; *Moraxella*, for example *M. catarrhalis*; and *Escherichia* for example *E. coli*; *Mycobacteria*, for example *M. tuberculosis*; *Helicobacter*, for example *H. pylori*; *Clostridium*, for example *C. difficile*; *Bacteroides* for example, *B. fragilis*, *B. vulgates*; intercellular microbes, for example *Chlamydia* and *Rickettsiae*; and *Mycoplasma*, for example *M. pneumoniae*, amongst others. The inventive rifamycin derivatives may be used as agents effective against GI disorders including travelers' and infectious diarrhea (*E. coli*, *Salmonella* and *Shigella*), hepatic encephalopathy, Crohn's disease, ulcerative colitis, irritable bowel syndrome, pouchitis, small-bowel bacterial overgrowth, peptic ulcer disease due to *H. pylori*, and diverticular disease. The present compounds also are envisioned as cytotoxic anticancer agents, antifungal agents, and antiprotozoal agents (against, for example, *entamoeba* histolyica, and *Neglaria* sps).

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

CITED REFERENCES

The following U.S. patents, patent documents, and publications are hereby incorporated by reference.

U.S. PATENT DOCUMENTS

U.S. Pat. No. 2,610,181
U.S. Pat. No. 2,944,061
U.S. Pat. No. 3,342,810
U.S. Pat. No. 3,950,351
U.S. Pat. No. 4,219,478
U.S. Pat. No. 4,983,602
U.S. Pat. No. 6,087,358

OTHER PATENT DOCUMENTS

International Patent Application Publication No. WO 2005/042542A1

OTHER PUBLICATIONS

Chaisson, R. E. "Treatment of chronic infections with rifamycins: is resistance likely to follow?", *Antimicrob. Agents & Chemother.* 47(10): p. 3037-39 (2003).
Farr, B. M. Rifamycins, in *Principles and Practice of Infectious Diseases*; Mandell, G. L., Bennett, J. E., Dolin, R., Eds.; Churchhill Livingstone: Philadelphia; p. 348-361.
Greene, T. H. and P. G. M. Wuts, *Protective Groups in Organic Synthesis,* 2nd edition, John Wiley & Sons, New York, 1991.
*Helv. Chim. Acta.,* 1973, 56, p. 2369.

What is claimed is:
1. A compound of structural formula (I) as defined below:

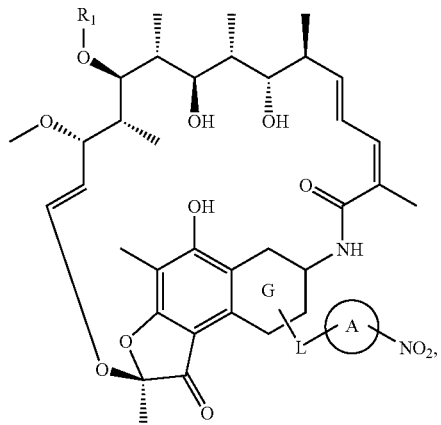

or their pharmaceutically acceptable salt thereof,
wherein $R_1$ is a hydrogen or acetyl group, G is a structure of formula II, III, IV or V:

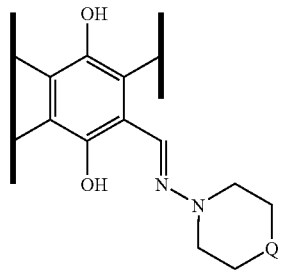

II

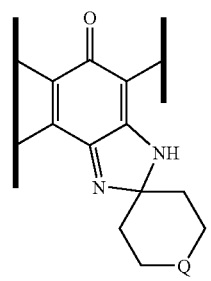

III

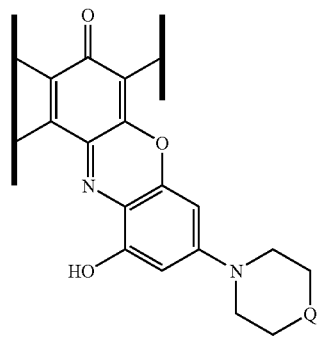

IV

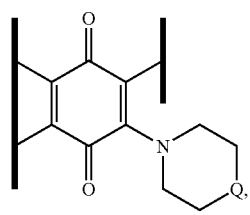

V wherein, in formula II, III, IV or V, Q is N— or $CR_2$—, which is bonded to a linkage group "L", which in turn is bonded to a structure

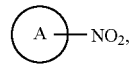

and $R_2$ is a group selected from hydrogen, $(C_1-C_6)$alkyl, aryl, heteroaryl, or heterocycloalkyl group;
L is a bond, or a linker group selected from one or a combination of two to five of the following groups:
1) $(C_1-C_6)$alkylene,
2) $(C_3-C_8)$cycloalkylene,
3) arylene,
4) heteroarylene,
5) heterocycloalkylene containing 1 to 3 heteroatoms,
6) —C(=O)—,
7) —C(=N—O—$R_3$)—, 8) —C=N—,
9) —O—,
10) —S(O)$_n$—, wherein n is number between 0 and 2,
11) —N(R$_4$)—,
wherein the carbon or nitrogen atoms of the linker group are unsubstituted or are independently substituted by 1 to 3 substituents selected from (C$_1$-C$_6$)alkyl, (C$_1$-C$_6$)alkyl, amino, (C$_1$-C$_6$)alkylamino, di(C$_1$-C$_6$)alkylamino, hydroxyl, (C$_1$-C$_6$)alkoxy or heterocycloalkyl group; R$_3$ and R$_4$ are independently a group selected from hydrogen, substituted or unsubstituted (C$_1$-C$_6$) alkyl, aryl, heteroaryl or heterocycloalkyl group; and structure

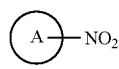

is a structural formula VI, VII, VIII or IX:

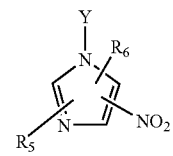
VI

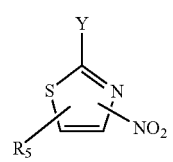
VII

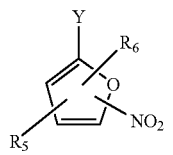
VIII

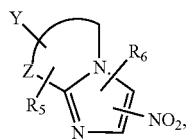
IX wherein Y is a bond which is bonded to linkage group "L", defined as above; and Z is a carbon (—CR$_7$R$_8$—), carbonyl (—C(O)—), amide (—C(O)NH—), sulfonamide (—S(O$_2$)N—), or a heteroatom selected from N, O, S, SO or SO$_2$; wherein R$_5$, R$_6$, R$_7$, and R$_8$ are independently a group selected from hydrogen, (C$_1$-C$_6$)alkyl, aryl, heteroaryl, or heterocycloalkyl group; R$_5$ and R$_6$, R$_7$ and R$_8$ can join together to form a five to seven-member ring system optionally containing one to three heteroatoms, and
wherein if R$_1$ is an acetyl group, G is II, Q is N—, and L is —C(=O)—, then

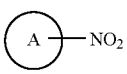

is not VIII in which R$_5$ and R$_6$ are hydrogen.

2. The compound of claim 1, wherein R$_1$ is acetyl group.

3. The compound of claim 1, wherein L is a bond or a group selected from one or a combination of two to three groups of:
1) (C$_1$-C$_6$)alkylene,
2) (C$_3$-C$_8$)cycloalkylene,
3) heterocycloalkylene containing 1 to 3 heteroatoms,
4) —C(=O)—,
5) —O—, and
6) —N(R$_4$)—,
wherein R$_4$ is selected from hydrogen, (C$_1$-C$_6$)alkyl, aryl, heteroaryl, and heterocycloalkyl groups that are all optionally substituted.

4. The compound of claim 1, wherein the structure

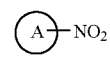

is selected from the following nitroheteroaryl groups:

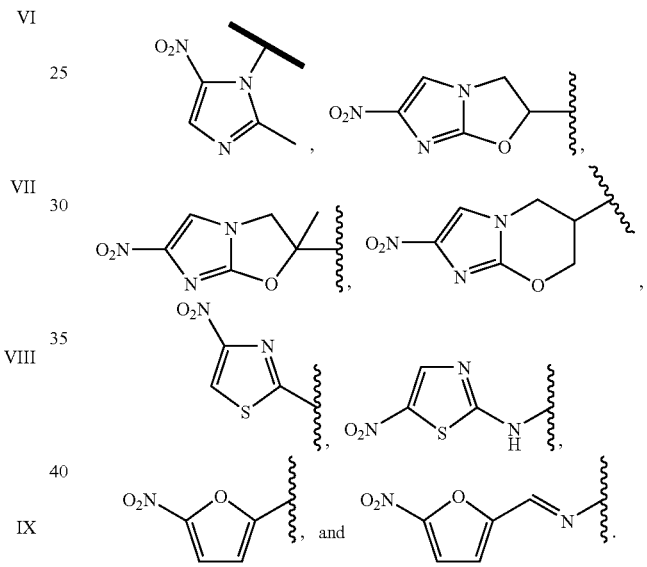

5. A compound selected from:
a. 4-Deoxy-3,4-[2-spiro-[1-[2-(2-methyl-5-nitro-imidazol-1-yl)ethyl]-piperidin-4-yl]]-(1H)-imidazo-(2,5-dihydro)rifamycin S,
b. 4-Deoxy-3,4-[2-spiro-[1-[(5-nitro-thiazol-2-ylcarbamoyl)-methyl]-piperidin-4-yl]]-(1H)-imidazo-(2,5-dihydro)rifamycin S,
c. 3'-Hydroxy-5'-[4-[2-(2-methyl-5-nitro-imidazol-1-yl)ethyl]-1-piperazinyl]benzoxazinorifamycin,
d. 3-[[[4-[2-(2-methyl-5-nitro-imidazol-1-yl)ethyl]-1-piperazinyl]imino]methyl]rifamycin SV,
e. 4-Deoxy-3,4-[2-spiro-[1-(2-methyl-6-nitro-2,3-dihydro-imidazo[2,1-b]oxazol-2-ylmethyl)-piperidin-4-yl]]-(1H)-imidazo-(2,5-dihydro)rifamycin S,
f. 3-{4-[4-(6-Nitro-2,3-dihydro-imidazo[2,1-b]oxazol-2-ylmethoxy)-benzyl]-piperazin-1-yl}rifamycin S,
g. 4-Deoxy-3,4-[2-[4-(6-nitro-2,3-dihydro-imidazo[2,1-b]oxazol-2-ylmethoxy)-phenyl]]-(1H)-imidazo-rifamycin SV,
h. 3-{4-[4-(2-Methyl-6-nitro-2,3-dihydro-imidazo[2,1-b]oxazol-2-ylmethoxy)-benzoyl]-piperazin-1-yl}rifamycin S, i. 4-Deoxy-3,4-[2-spiro-[1-[4-[6S-(2-nitro-6,7-dihydro-5H-imidazo[2,1-b][1,3]oxazin-6-yloxymethyl)]-benzyl]-piperidin-4-yl]]-(1H)-imidazo-(2,5-dihydro)rifamycin S,
j. 3-{4-[4-[(6S)-(2-Nitro-6,7-dihydro-5H-imidazo[2,1-b][1,3]oxazin-6-yloxymethyl)]-benzyl]-piperazin-1-yl}rifamycin S,
k. 3-{4-[4-(2-Methyl-6-nitro-2,3-dihydro-imidazo[2,1-b]oxazol-2-ylmethoxy)-benzyl]-piperazin-1-yl}rifamycin S,
l. 3'-Hydroxy-5'-[4-[4-(6S-2-nitro-6,7-dihydro-5H-imidazo[2,1-b][1,3]oxazin-6-yloxymethyl)-benzyl]-1-piperazinyl]benzoxazinorifamycin,
m. 4-Deoxy-3,4-[2-spiro-[1-[3-(6S-2-nitro-6,7-dihydro-5H-imidazo[2,1-b][1,3]oxazin-6-yloxymethyl)]-benzyl]-piperidin-4-yl]]-(1H)-imidazo-(2,5-dihydro)rifamycin S,
n. 3-{4-[3-(6S-(2-Nitro-6,7-dihydro-5H-imidazo[2,1-b][1,3]oxazin-6-yloxymethyl)]-benzyl]-piperazin-1-yl}rifamycin S,
o. 3'-Hydroxy-5'-[4-[3-(6S'-2-nitro-6,7-dihydro-5H-imidazo[2,1-b][1,3]oxazin-6-yloxymethyl)-benzyl]-1-piperazinyl]benzoxazinorifamycin,
p. 3-[[[4-[4-(6S-2-Nitro-6,7-dihydro-5H-imidazo[2,1-b][1,3]oxazin-6-yloxymethyl)-benzyl]-piperazin-1-yl]imino]methyl]rifamycin SV,
q. 4-Deoxy-3,4-[2-spiro-[1-[[4-(6S-2-nitro-6,7-dihydro-5H-imidazo[2,1-b][1,3]oxazin-6-yloxymethyl)-phenoxy]-acetyl]-piperidin-4-yl]-(1H)-imidazo-(2,5-dihydro)rifamycin S,
r. 3-[4-[1-[4-(6S-2-Nitro-6,7-dihydro-5H-imidazo[2,1-b][1,3]oxazin-6-yloxymethyl)-benzyl]-1H-[1,2,3]triazol-4-ylmethyl]-piperazin-1-yl]rifamycin S,
s. 3'-Hydroxy-5'-[4-[1-[4-(6S-2-nitro-6,7-dihydro-5H-imidazo[2,1-b][1,3]oxazin-6-yloxymethyl)-benzyl]-1H-[1,2,3]triazol-4-ylmethyl]-piperazin-1-yl]-benzoxazinorifamycin,
t. 3'-Hydroxy-5'-{4-[4-(2-methyl-6-nitro-2,3-dihydro-imidazo[2,1-b]oxazol-2-ylmethoxy)-phenyl]-piperazin-1-yl}-benzoxazinorifamycin,
u. 3-(2-{4-[4-(2-Methyl-6-nitro-2,3-dihydro-imidazo[2,1-b]oxazol-2-ylmethoxy)-phenyl]-piperazin-1-yl}) Rifamycin S,
v. 3-[4-(2-{4-[4-(2-methyl-6-nitro-2,3-dihydro-imidazo[2,1-b]oxazol-2-ylmethoxy)-phenyl]-piperazin-1-yl}-acetyl)-piperazin-1-yl]-rifamycin S,
w. 4-Deoxy-3,4-[2-spiro-[1-[2-(2-nitro-6,7-dihydro-5H-imidazo[2,1-b][1,3]oxazin-6-yloxy)-acetyl]-piperidin-4-yl]]-(1H)-imidazo-(2,5-dihydro)rifamycin S,
x. 2-[4-(2-Bromo-4-nitro-imidazol-1-ylmethyl)-4-hydroxy-piperidin-1-yl]-rifamycin S,
y. 3-{4-[2-(6S-2-Nitro-6,7-dihydro-5H-imidazo[2,1-b][1,3]oxazin-6-yloxy)-acetyl]-piperazin-1-yl}-rifamycin S, and
z. 3-[4-(2-Methyl-6-nitro-2,3-dihydro-imidazo[2,1-b]oxazol-2-ylmethyl)-piperazin-1-yl]rifamycin S.

6. A pharmaceutical composition, useful as a medicament for treatment of bacterial infections, comprising therapeutically effective amount of a compound in accordance with claim 1 in combination with a pharmaceutically acceptable carrier.

7. A method of treating bacterial infections in a patient in need of such treatment by administering a pharmaceutical composition as defined by claim 6.

\* \* \* \* \*